US008669106B2

(12) United States Patent
Sakthivel et al.

(10) Patent No.: US 8,669,106 B2
(45) Date of Patent: Mar. 11, 2014

(54) ERYTHROCYTES DIFFERENTIATED IN VITRO FROM NANOFIBER EXPANDED CD133+ CELLS

(75) Inventors: Ramasamy Sakthivel, Solon, OH (US); Donald J. Brown, Hopkington, MA (US); Hai-Quan Mao, Baltimore, MD (US); Luc Douay, Paris (FR); Vincent J. Pompili, Upper Arlington, OH (US); Kevin McIntosh, Brooklyn Park, MN (US); Hiranmoy Das, Upper Arlington, OH (US); Yukang Zhao, Framingham, MA (US)

(73) Assignees: Arteriocyte Inc., Cleveland, OH (US); Universite Pierre ET Marie Curie (Paris VI), Paris (FR)

( * ) Notice: Subject to any disclaimer, the term of this patent is extended or adjusted under 35 U.S.C. 154(b) by 1188 days.

(21) Appl. No.: 12/351,630

(22) Filed: Jan. 9, 2009

(65) Prior Publication Data
US 2009/0285892 A1 Nov. 19, 2009

Related U.S. Application Data

(63) Continuation-in-part of application No. 11/975,492, filed on Oct. 18, 2007, now Pat. No. 8,361,502.

(60) Provisional application No. 60/852,598, filed on Oct. 18, 2006, provisional application No. 61/010,917, filed on Jan. 10, 2008, provisional application No. 61/190,544, filed on Aug. 28, 2008.

(51) Int. Cl.
C12N 5/00 (2006.01)

(52) U.S. Cl.
USPC ........... 435/377; 435/385; 435/386; 435/387; 435/398; 435/399

(58) Field of Classification Search
None
See application file for complete search history.

(56) References Cited

U.S. PATENT DOCUMENTS

| 7,470,538 B2 | 12/2008 | Laughlin et al. |
| 2004/0258670 A1 | 12/2004 | Laughlin et al. |
| 2005/0069527 A1 | 3/2005 | Laughlin et al. |
| 2008/0153163 A1 | 6/2008 | Mao et al. |

FOREIGN PATENT DOCUMENTS

| WO | WO 2005/118780 | 12/2005 |
| WO | WO 2008/085229 | 7/2008 |

OTHER PUBLICATIONS

Giaratana et al. Ex vivo generation of fully mature human red blood cells from hematopoietic stem cells Nature Biotechnology, 2005, vol. 23, pp. 69-74.*
He et al. Differential Gene Expression Profiling of CD34 CD133 Umbilical Cord Blood Hematopoietic Stem Progenitor CellsStem Cells Devel. 2005, vol. 14, pp. 188-198.*
Kobari et al. CD133+ Cell Selection Is an Alternative to CD34+ Cell Selection for Ex Vivo Expansion of Hematopoietic Stem Cells. J Hematotherapy & Stem Cell Res., 2001, vol. 10, 273-281.*
Peichev et al. Expression of VEGFR-2 and AC133 by circulating human CD341 cells identifies a population of functional endothelial precursors. Blood, 2000, vol. 95, pp. 952-958.*
Cabrita et al. Hematopoietic stem cells:from the bone to the bioreactor. Trends in Biotechnology, 2003, vol. 21, pp. 233-240.*
Akiyama et al., Changes of telomere length in children after hematopoietic stem cell transplantation, Bone Marrow Transplant 21:167-171 (1998).
Akiyama, Shortening of telomeres in recipients of both autologous and allogeneic hematopoietic stem cell transplantation, Bone Marrow Transplantation 25:441-447 (2000).
Atthoff et al., Protein adsorption onto polyester surfaces: is there a need for surface activation? J Biomed Mater Res B Appl Biomater 80:121-130 (2007).
Bagley et al., Extended culture of multipotent hematopoietic progenitors without cytokine augmentation in a novel three-dimensional device, Exp.Hematol. 27:496-504 (1999).
Banu et al., Cytokine-augmented culture of haematopoietic progenitor cells in a novel three-dimensional cell growth matrix, Cytokine 13:349-358 (2001).
Blair et al., Ex vivo expansion of megakaryocyte progenitor cells from normal bone marrow and peripheral blood and from patients with haematological malignancies, Br J Haematol 116:912-919 (2002).
Boiron et al., Large-scale expansion and transplantation of CD34(+) hematopoietic cells: in vitro and in vivo confirmation of neutropenia abrogation related to the expansion process without impairment of the long-term engraftment capacity, Transfusion 46:1934-1942 (2006).
Braccini et al. Three-dimensional perfusion culture of human bone marrow cells and generation of osteoinductive grafts, Stem Cells 23:1066-1072 (2005).
Brugger et al., Ex vivo expansion of enriched peripheral blood CD34+ progenitor cells by stem cell factor, interleukin-1 beta (IL-1 beta), IL-6, IL-3, interferon-gamma, and erythropoietin. Blood 81:2579-2584 (1993).
Cabrita et al., Hematopoietic stem cells: from the bone to the bioreactor, Trends Biotechnol. 21:233-240 (2003).
Chiu et al., Induction of vascular endothelial phenotype and cellular proliferation from human cord blood stem cells cultured in simulated microgravity, Acta Astronaut 56:918-922 (2005).
Chivu et al., Ex vivo differentiation of umbilical cord blood progenitor cells in the presence of placental conditioned medium. J Cell Mol Med 6:609-620 (2002).
Chua et al., Functional nanofiber scaffolds with different spacers modulate adhesion and expansion of cryopreserved umbilical cord blood hematopoietic stem/progenitor cells, Exp. Hem. 35(5):771-781 (2007).

(Continued)

Primary Examiner — Deborah Crouch
(74) Attorney, Agent, or Firm — Ropes & Gray LLP

(57) ABSTRACT

The invention provides, among other things, methods and systems for expanding CD133+ cells. The invention further provides methods and systems for increasing the blood flow to an ischemic tissue in a subject in need thereof, such as to ischemic myocardium. The invention further provides methods and systems for directing differentiation of expanded CD133+ cells. The invention further provides methods and systems for treating a subject with differentiated cells in a subject in need thereof.

34 Claims, 53 Drawing Sheets

(56) References Cited

OTHER PUBLICATIONS

Chua et al., Stable immobilization of rat hepatocyte spheroids on galactosylated nanofiber scaffold, Biomaterials 26(15):2537-2547 (2005).
Chua et al., Surface-aminated electrospun nanofibers enhance adhesion and expansion of human umbilical cord blood hematopoietic stem/progenitor cells, Biomaterials 27(36):6043-6051 (2006).
Daniels, Expression of red cell surface antigens during erythropoiesis, Vox Sang. 78(2)149-153 (2000).
Das et al., Successful surface-aminated nanofiber expansion of human umbilical cord-derived CD133+ cells leads to augmentation of angiogenic functionality in vitro and in vivo, Circulation 116(16):231 (2007).
De Bruyn et al., Ex vivo expansion of megakaryocyte progenitor cells: cord blood versus mobilized peripheral blood, Stem Cells Dev 14:415-424 (2005).
Douay et al., Ex vivo production of human red blood cells from hematopoietic stem cells: what is the future in transfusion? Transfus Med Rev 21:91-100 (2007).
Douay et al., In vitro generation of mature and functional human red blood cells: a model with multidisciplinary perspectives, Bull Acad Natl Med 189:903-13; discussion 914-5 (2005).
Douay et al., The cultured red blood cell: a study tool with therapeutic perspectives, Cell Cycle 4:999-1000 (2005).
Douay, From control of hematopoiesis to cellular therapy: the perspectives for transfusion, Ann Biol Clin (Paris) 61:259-267 (2003).
Douay, Transfusional perspectives for ex vivo control of hematopoiesis, Transfus Clin Biol 10:151-155 (2003).
Ehring et al. Expansion of HPCs from cord blood in a novel 3D matrix, Cytotherapy 5:490-499 (2003).
Fibach et al., Proliferation and maturation of human erythroid progenitors in liquid culture, Blood 73:100-103 (1989).
Finney et al., Direct comparison of umbilical cord blood versus bone marrow-derived endothelial precursor cells in mediating neovascularization in response to vascular ischemia, Biol Blood Marrow Transplant 12:585-593 (2006).
Gandhi et al., A novel strategy for generating platelet-like fragments from megakaryocytic cell lines and human progenitor cells, Blood Cells Mol Dis. 35:70-73 (2005).
Gehling et al., In vitro differentiation of endothelial cells from AC133-positive progenitor cells Blood 95:3106-3112 (2000).
George et al., Expanded and genetically modified human cord blood-derived CD133+ stem cells improves cardiac function in a rat model of acute myocardial infarction, J. Inv. Med. 56(3):654-655 (2008).
Giarratana et al., Cultured red blood cells: a new step in cell engineering, Med Sci (Paris) 21:231-232 (2005).
Giarratana et al., Ex vivo generation of fully mature human red blood cells from hematopoietic stem cells, Nat Biotechnol 23:69-74 (2005).
Giarratana, Cell culture bags allow a large extent of exvivoexpansion of LTC-IC and functional mature cells which can subsequently be frozen: interest for a large-scale clinical applications, Bone Marrow Transplant. 22:707-715 (1998).
Gregory, Three stages of erythropoietic progenitor cell differentiation distinguished by a number of physical and biologic properties, Blood 51:527-537 (1978).
Hanspal, The association of erythroblasts with macrophages promotes erythroid proliferation and maturation: a 30-kD heparin-binding protein is involved in this contact, Blood 84:3494-3504 (1994).
Hartley et al., Electrostatic Properties of Polyelectrolyte Modified Surfaces Studied by Direct Force Measurement, Langmuir 14:6948-6955 (1998).
Joneckis et al., Integrin alpha 4 beta 1 and glycoprotein IV (CD36) are expressed on circulating reticulocytes in sickle cell anemia, Blood 82:3548-3555 (1993).
Kelly et al., Umbilical cord blood stem cells: application for the treatment of patients with hemoglobinopathies [see comments]. J Pediatr 130:695-703 (1997).
Kie et al., Ultrastructural and phenotypic analysis of in vitro erythropoiesis from human cord blood CD34+ cells, Ann Hematol 82:278-283 (2003).
Lichtman, The ultrastructure of the hemopoietic environment of the marrow: a review, Exp Hematol. 9:391-410 (1981).
Long et al., Human hematopoietic stem cell adherence to cytokines and matrix molecules, J. Clin. Invest. 90:251-255 (1992).
Malik et al., An in vitro model of human red blood cell production from hematopoietic progenitor cells. Blood 91:2664-2671 (1998).
Mantalaris et al., Engineering a human bone marrow model: a case study on ex vivo erythropoiesis, Biotechnol Prog. 14:126-133 (1998).
Meissner et al., Development of a fixed bed bioreactor for the expansion of human hematopoietic progenitor cells, Cytotechnology 30:227-234 (1999).
Migliaccio et al., In vitro mass production of human erythroid cells from the blood of normal donors and of thalassemic patients, Blood Cells Mol Dis. 28:169-180 (2002).
Miharada et al., Lipocalin 2 functions as a negative regulator of red blood cell production in an autocrine fashion, Faseb J 19:1881-1883 (2005).
Miharada et al., Refinement of cytokine use in the in vitro expansion of erythroid cells, Hum Cell 19:30-37 (2006).
Mohandas, Three-dimensional model of bone marrow, Blood 51:633-643 (1978).
Molla et al., Extracellular matrix receptors and the differentiation of human megakaryocytes in vitro, Leuk Lymphoma 33:15-23 (1999).
Nelson et al., Predictors of mortality in close proximity blast injuries during Operation Iraqi Freedom, J. Amer.Coll. Surg. 202:418-422 (2006).
Plett et al., Impact of modeled microgravity on migration, differentiation, and cell cycle control of primitive human hematopoietic progenitor cells, Exp Hematol 32:773-781 (2004).
Plett et al., Proliferation of human hematopoietic bone marrow cells in simulated microgravity, In Vitro Cell Dev Biol Anim 37:73-78 (2001).
Quirici et al. Differentiation and expansion of endothelial cells from human bone marrow CD133(+) cells, Br J Haematol 115:186-194 (2001).
Sawada et al., Purification of human blood burst-forming units-erythroid and demonstration of the evolution of erythropoietin receptors, J Cell Physiol 142:219-230 (1990).
Scicchitano et al., In vitro expansion of human cord blood CD36+ erythroid progenitors: temporal changes in gene and protein expression, Exp Hematol 31:760-769 (2003).
Stacey et al., The development of 'feeder' cells for the preparation of clinical grade hES cell lines: challenges and solutions, J Biotechnol 125:583-588 (2006).
Verfaillie et al., Adhesion of committed human hematopoietic progenitors to synthetic peptides from the C-terminal heparin-binding domain of fibronectin: cooperation between the integrin alpha 4 beta 1 and the CD44 adhesion receptor, Blood 84:1802-1811 (1994).
Vuillet-Gaugler et al., Loss of attachment to fibronectin with terminal human erythroid differentiation, Blood 75:865-873 (1990).
Winslow, Current status of blood substitute research: towards a new paradigm, J Intern Med 253:508-517 (2003).
Zhao et al., Perfusion bioreactor system for human mesenchymal stem cell tissue engineering: dynamic cell seeding and construct development, Biotechnol Bioeng 91:482-493 (2005).

\* cited by examiner

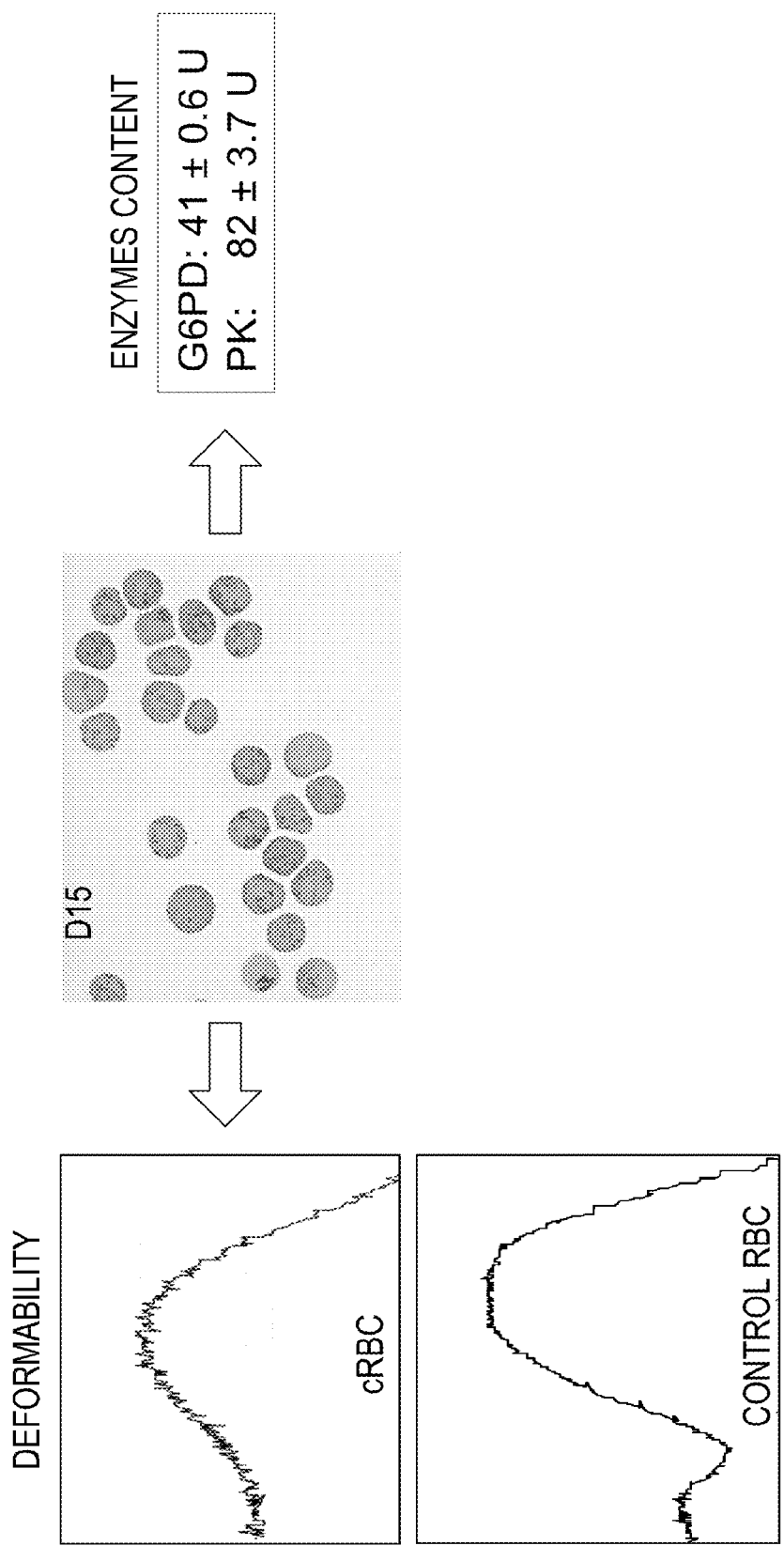
Figure 13 (part 1)

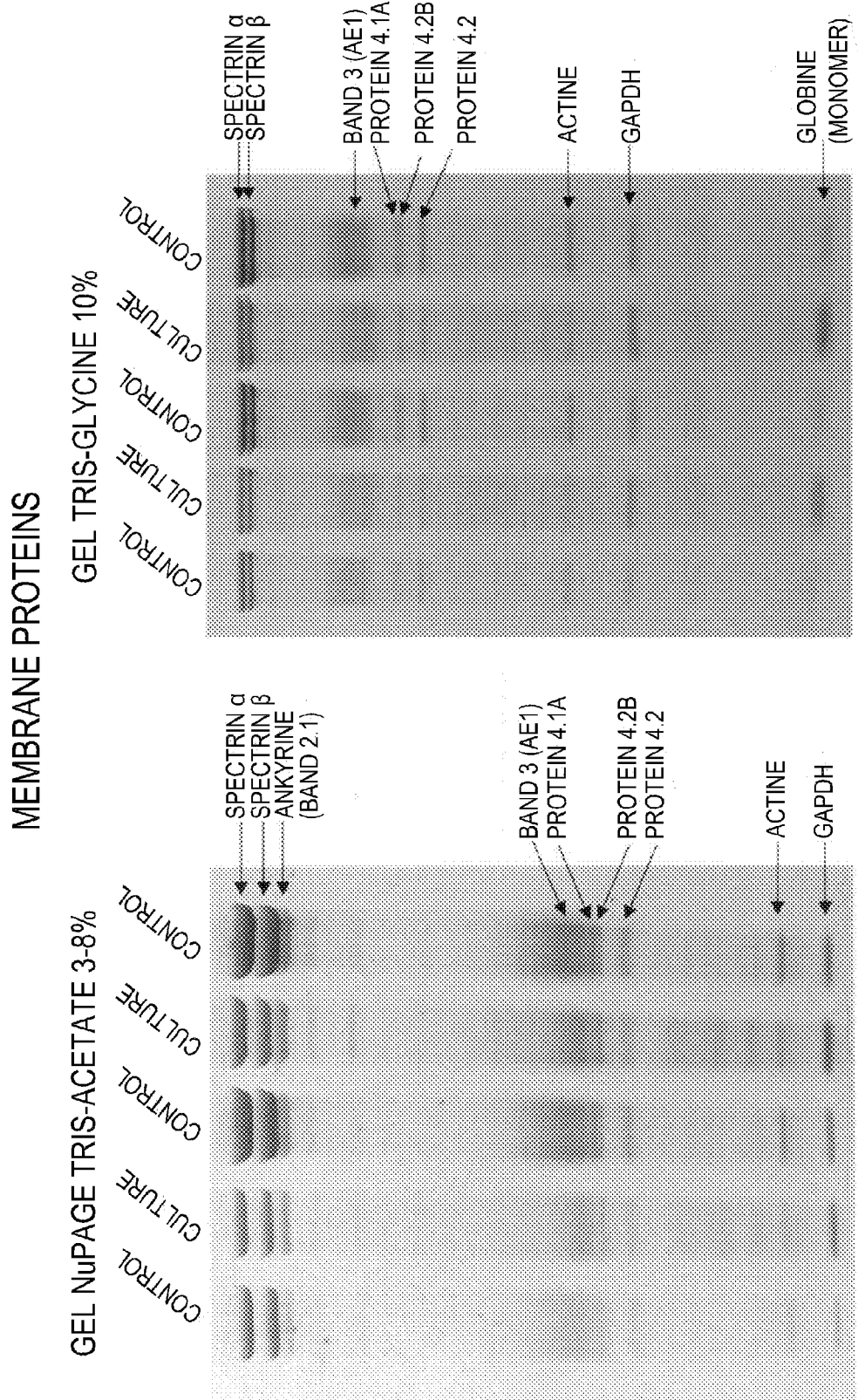
Figure 13 (part 2)

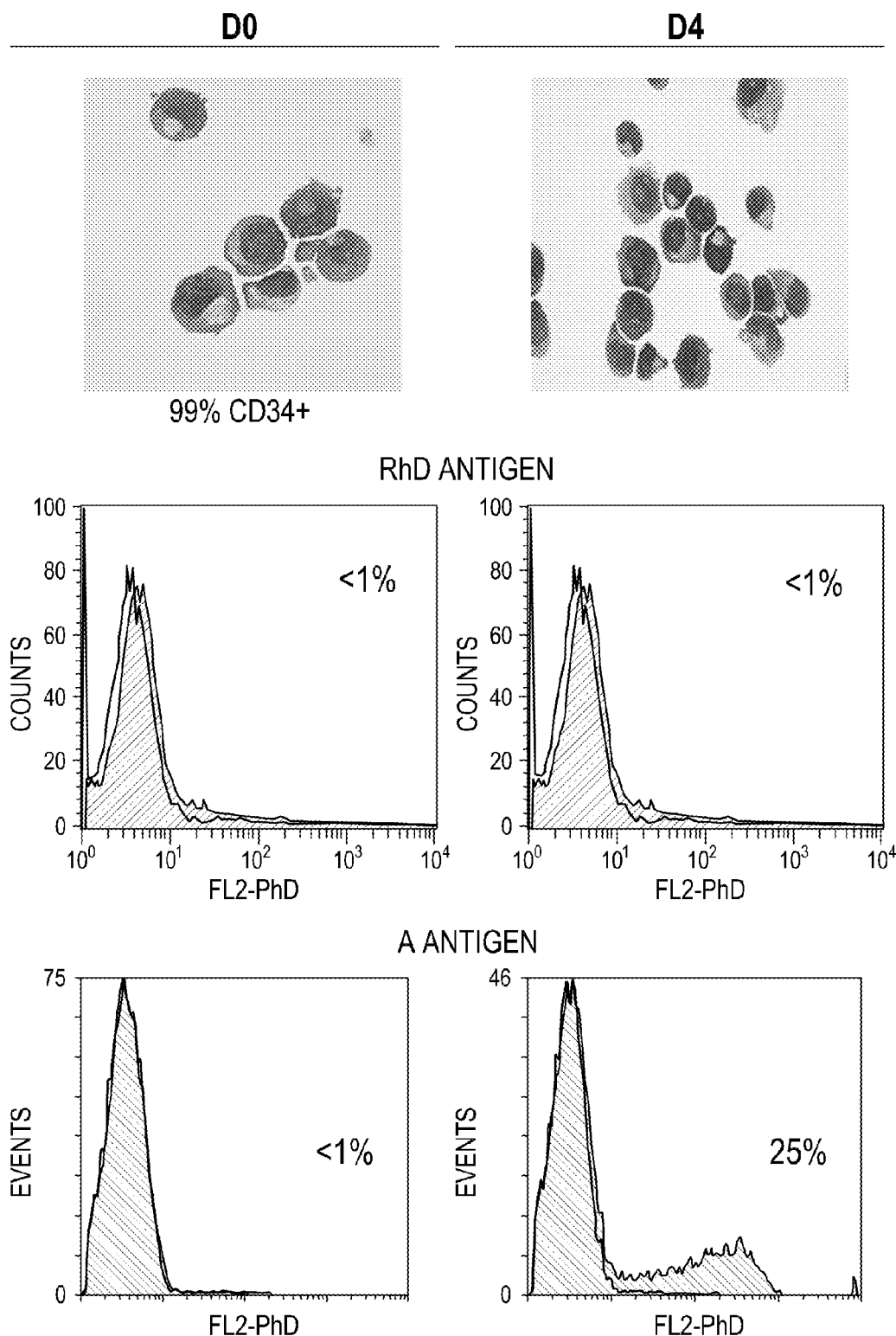
Figure 16 (part1)

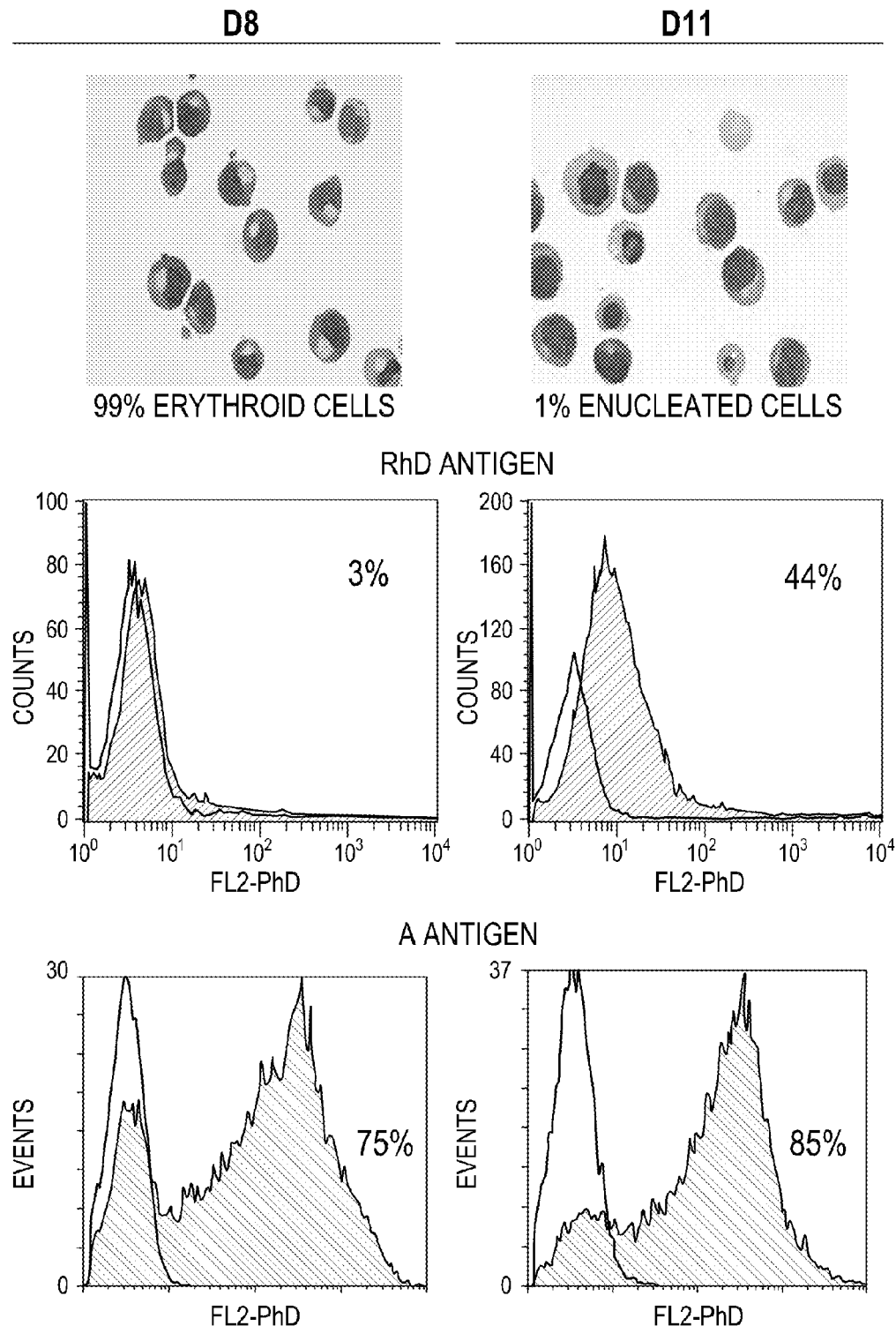
Figure 16 (part2)

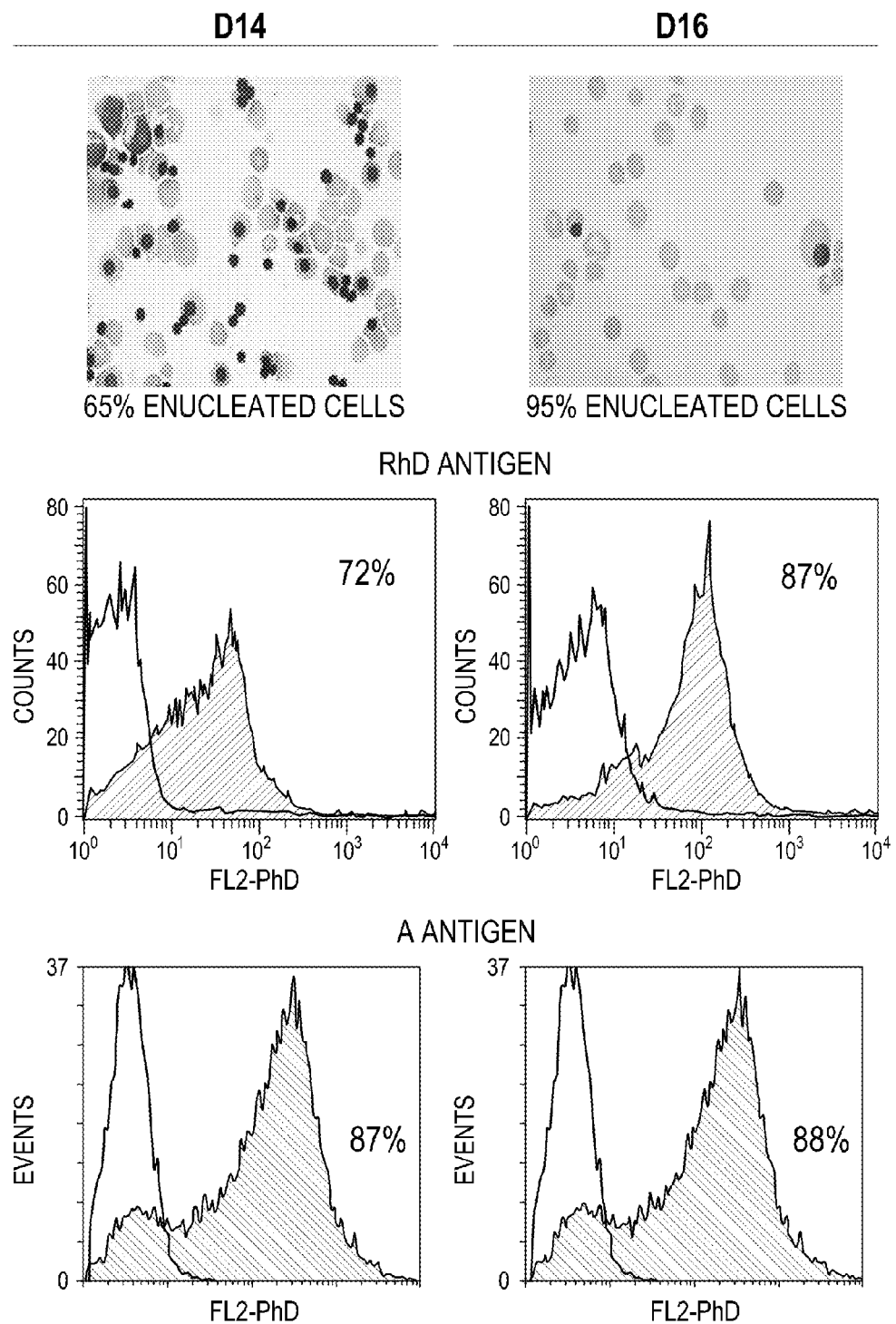
Figure 16 (part3)

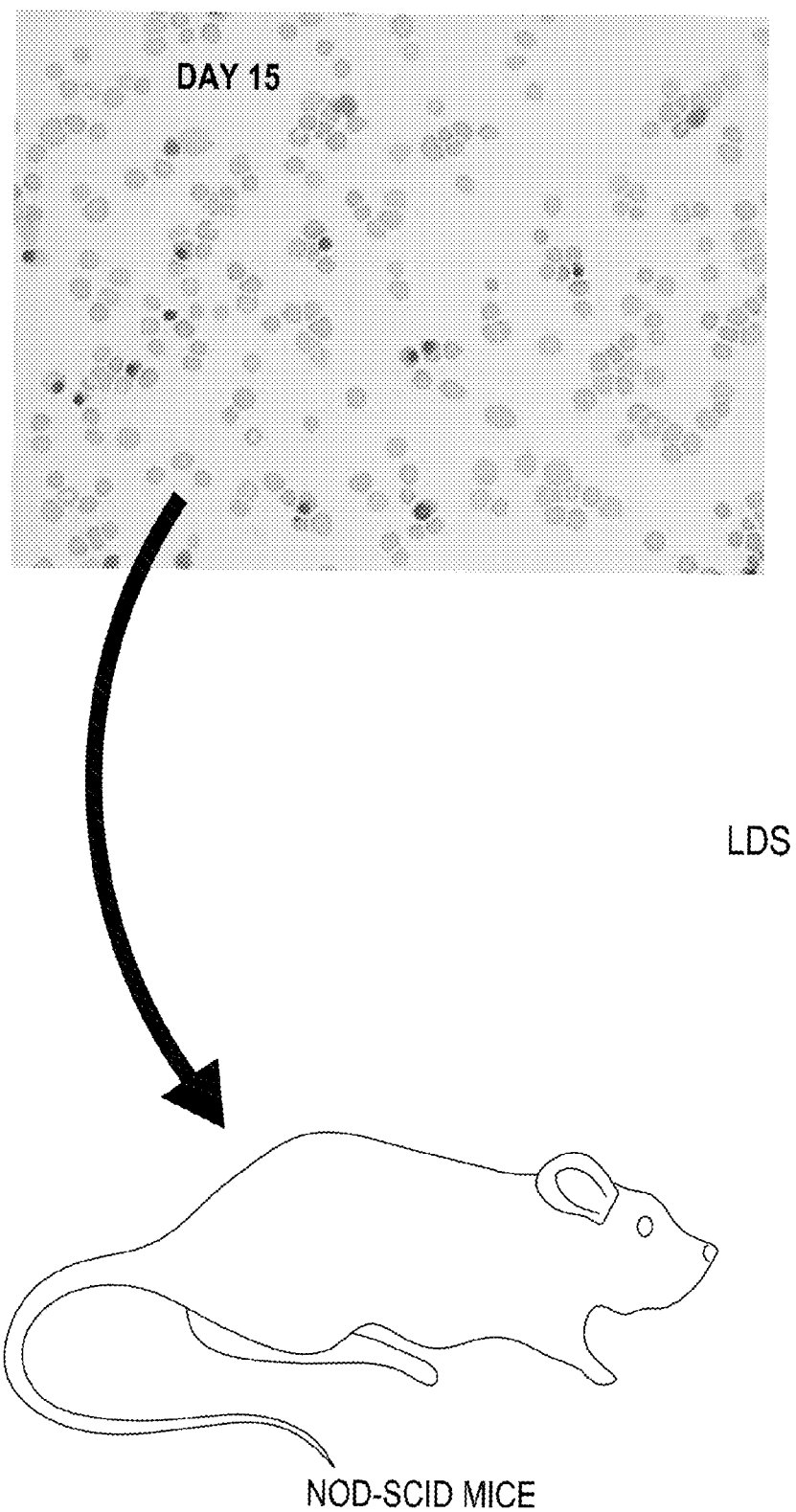
Figure 17 (part 1)

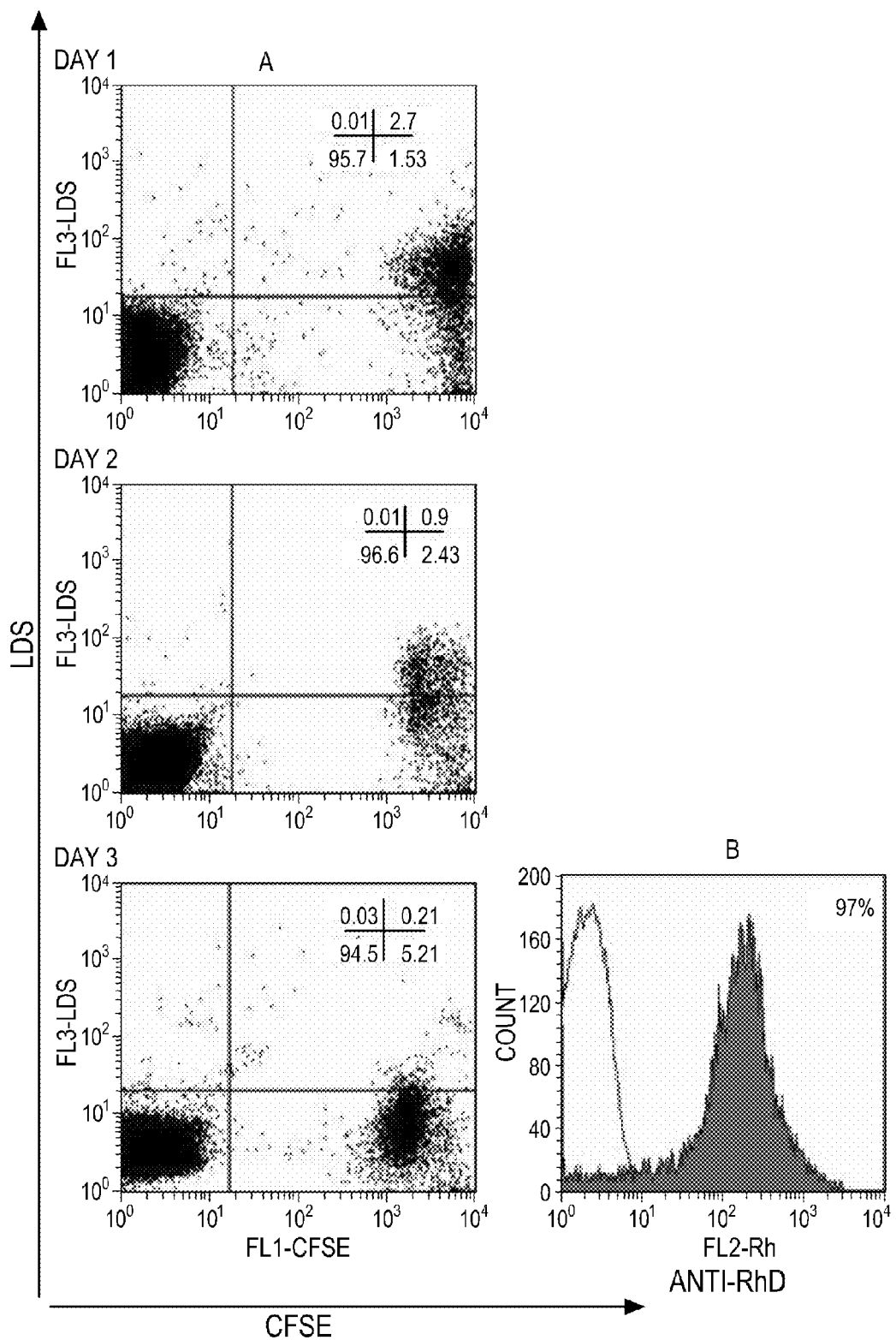
Figure 17 (part 2)

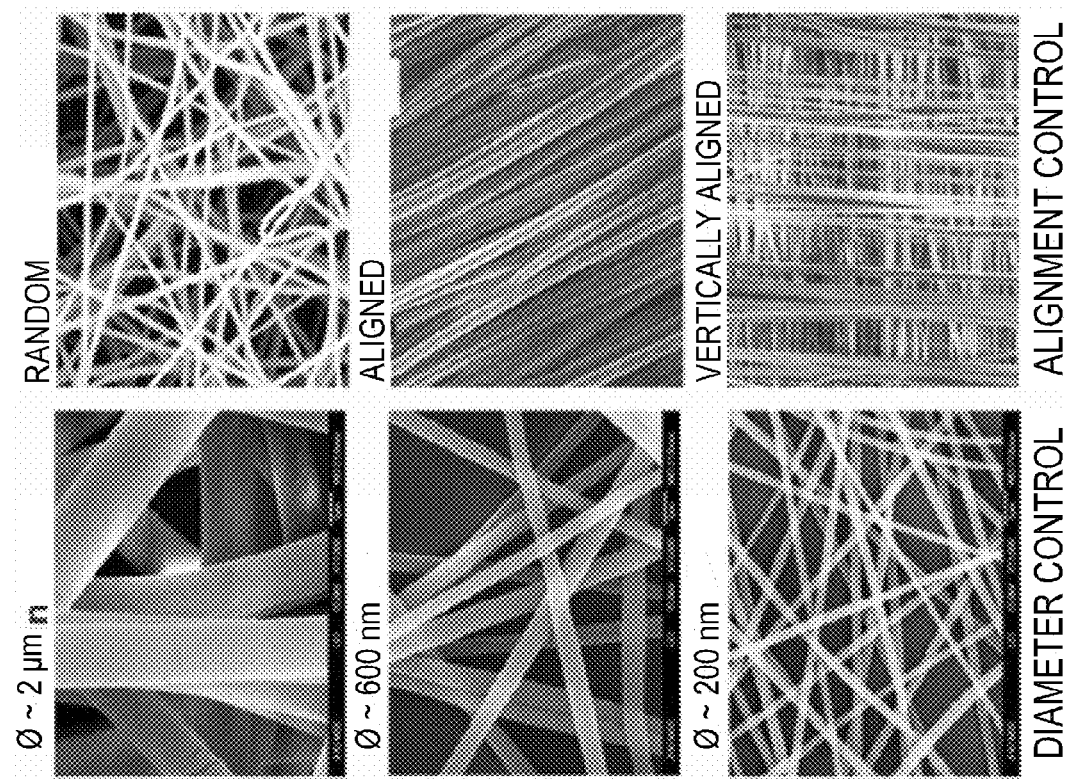
Figure 22 (part 1)

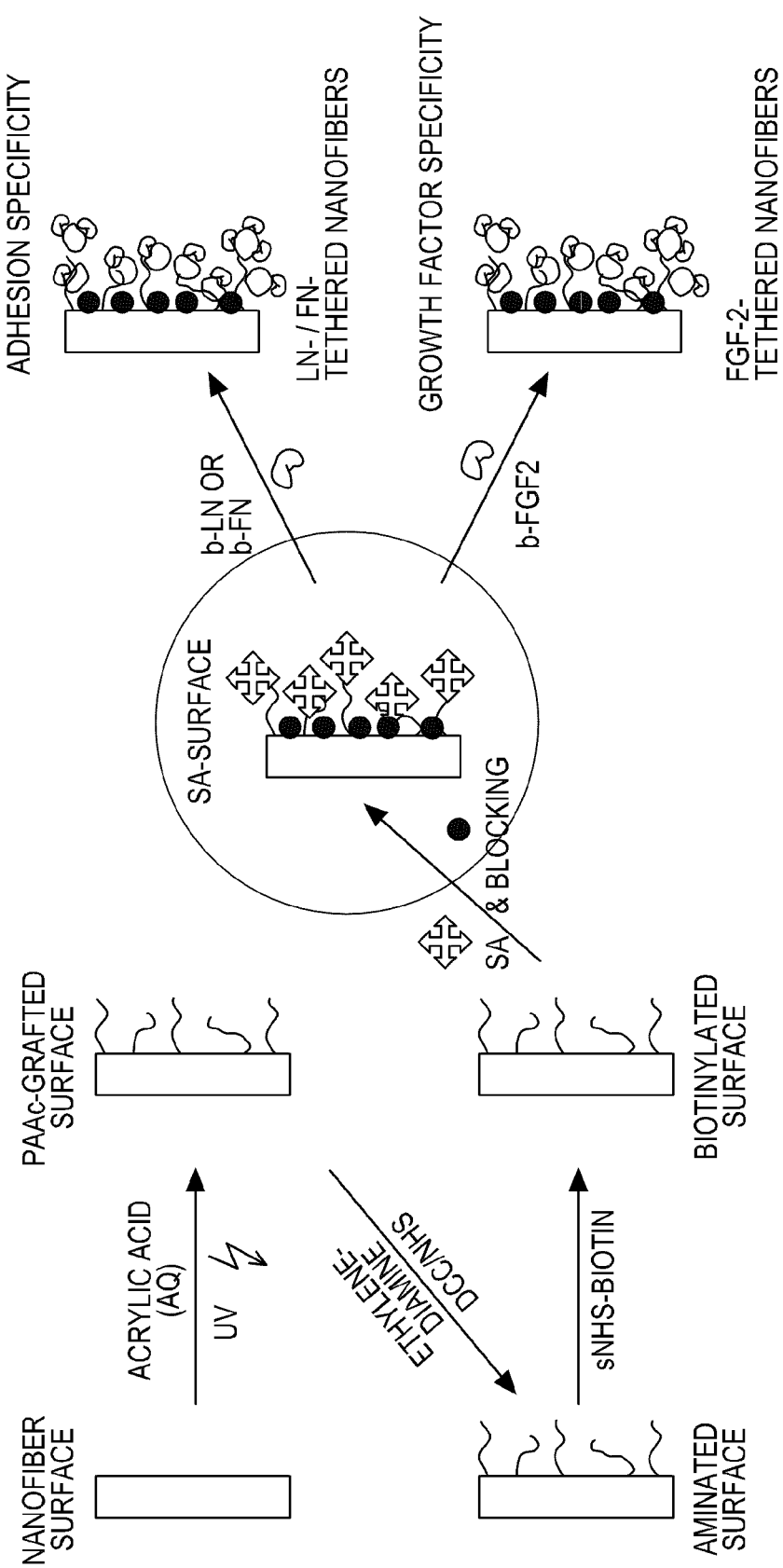
Figure 22 (part 2)

Fold Expansion
- Day 0: 1.0
- Day 10: 232.5 (reculture)
- Day 13: 438.49 (reculture)
- Day 16: 1,578.56 (reculture)
- Day 22: 24,546.67 (reculture)
- Day 27: 49,093.9

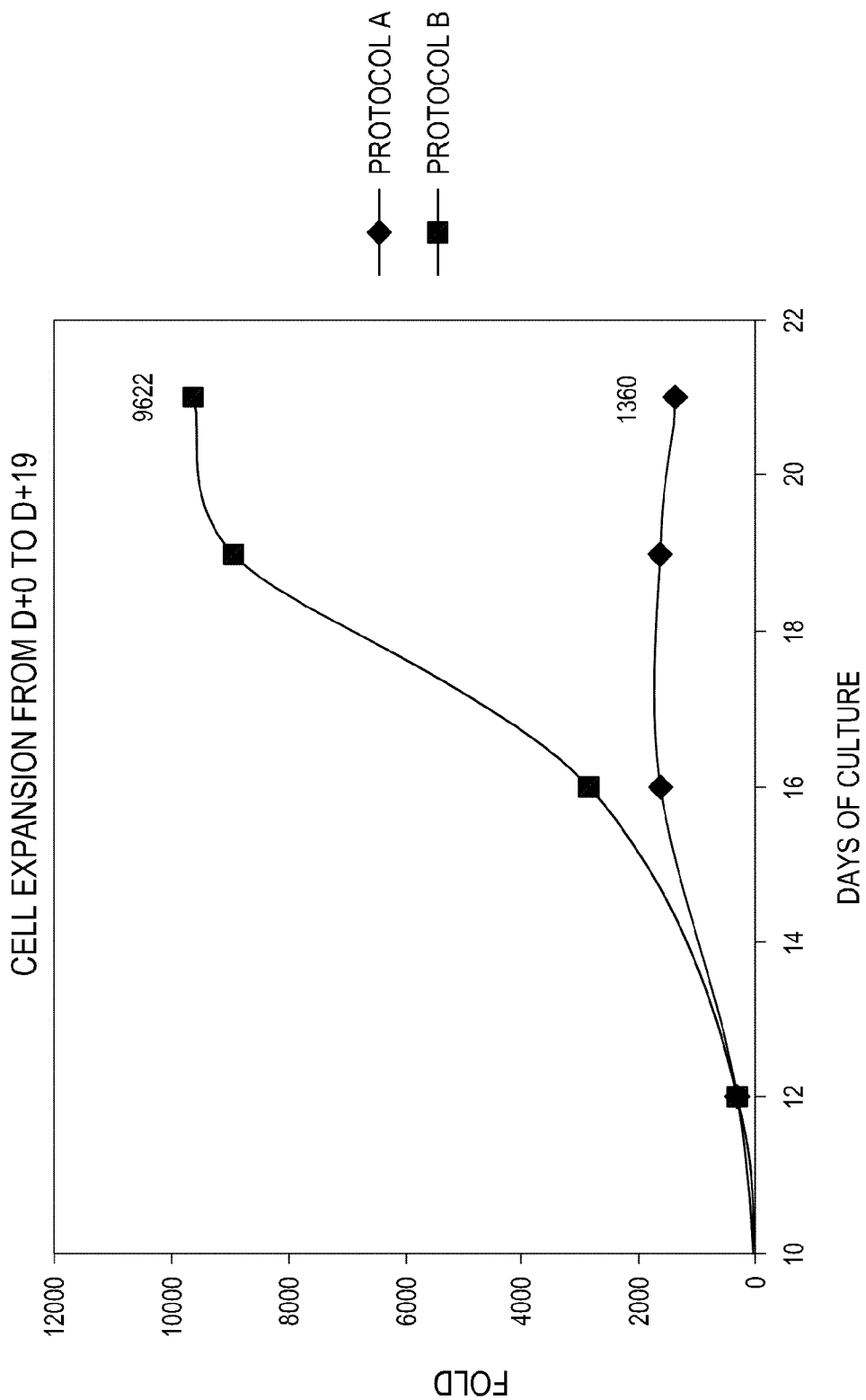
Figure 38 (part 1)

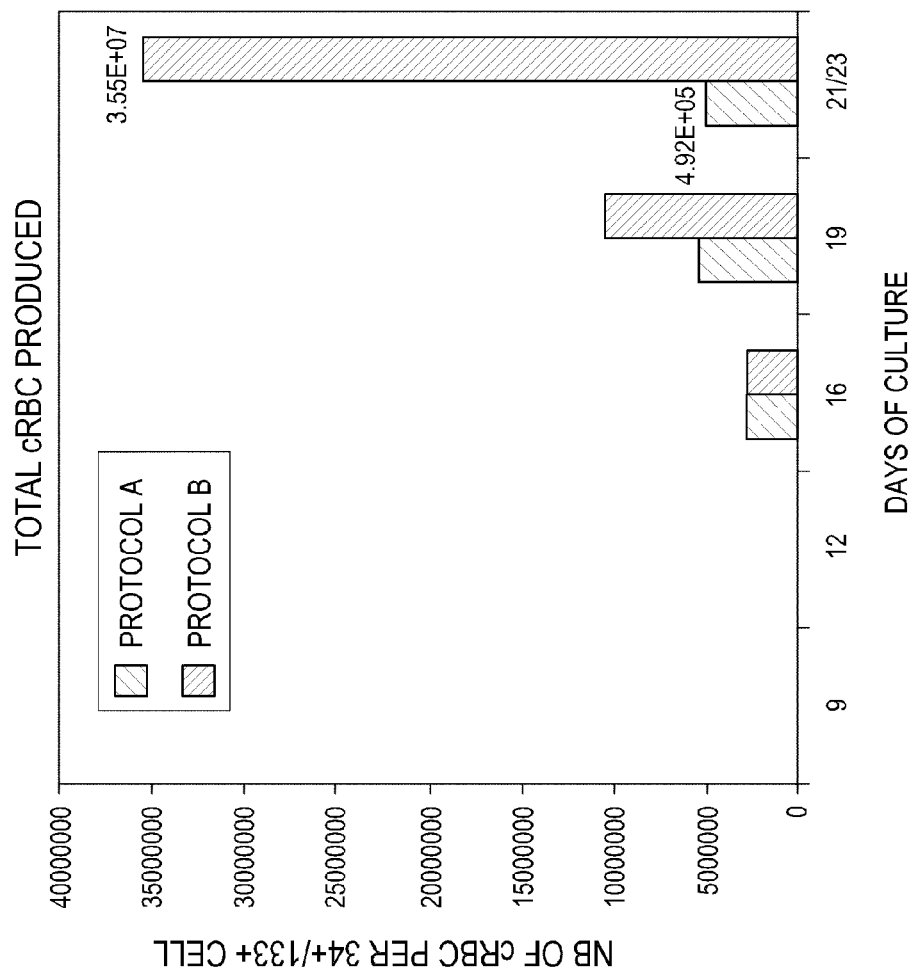
Figure 38 (part 2)

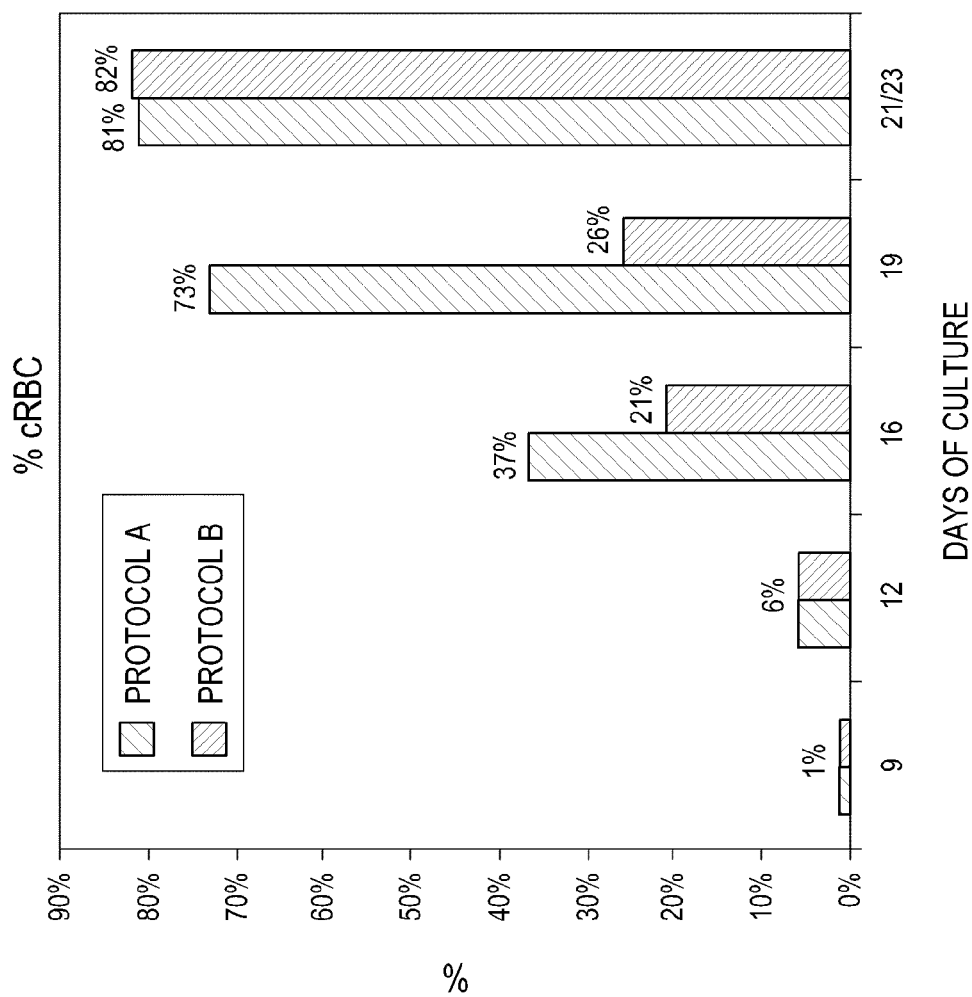
Figure 38 (part 3)

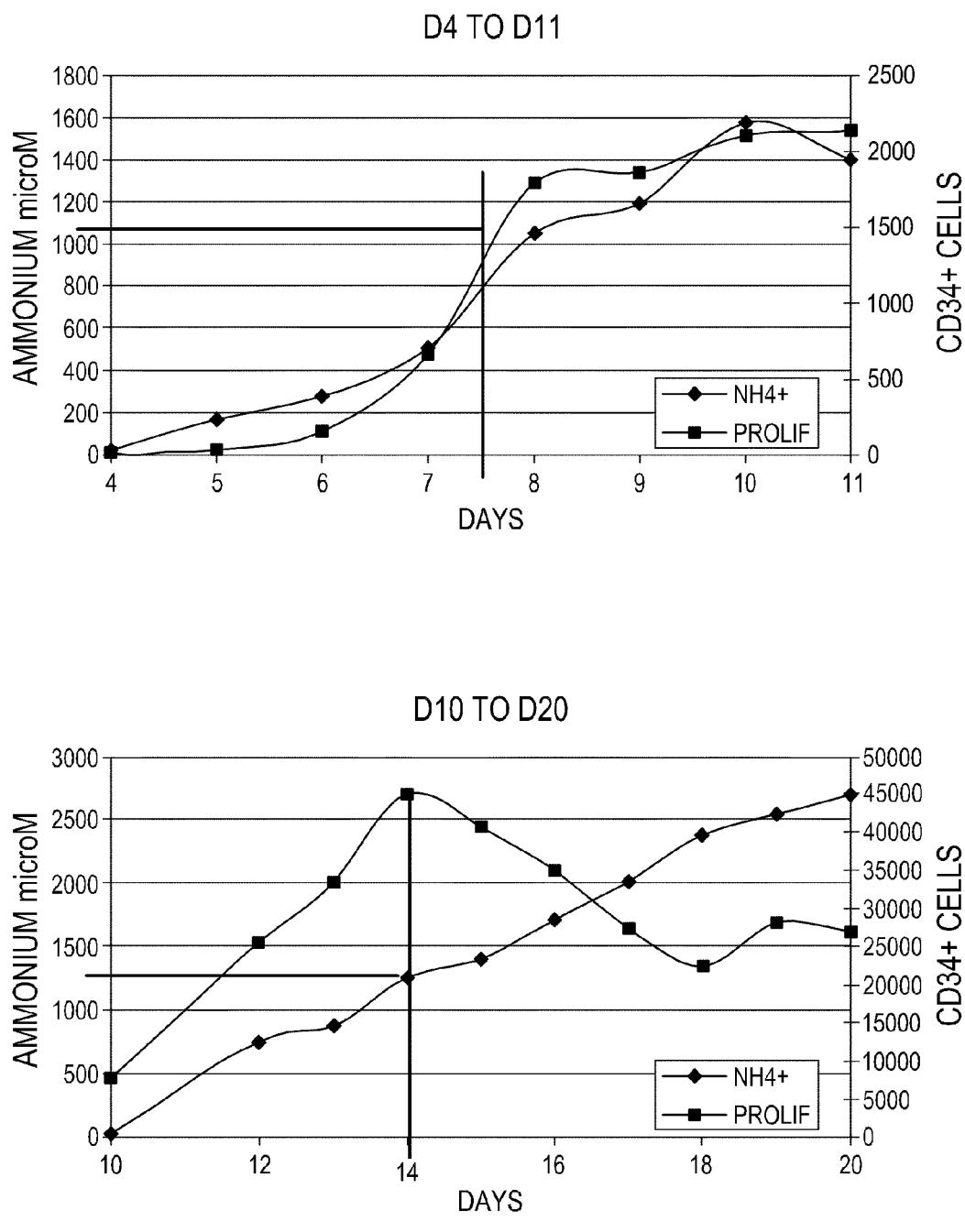
1Mm THRESHOLD
Figure 40 (part 1)

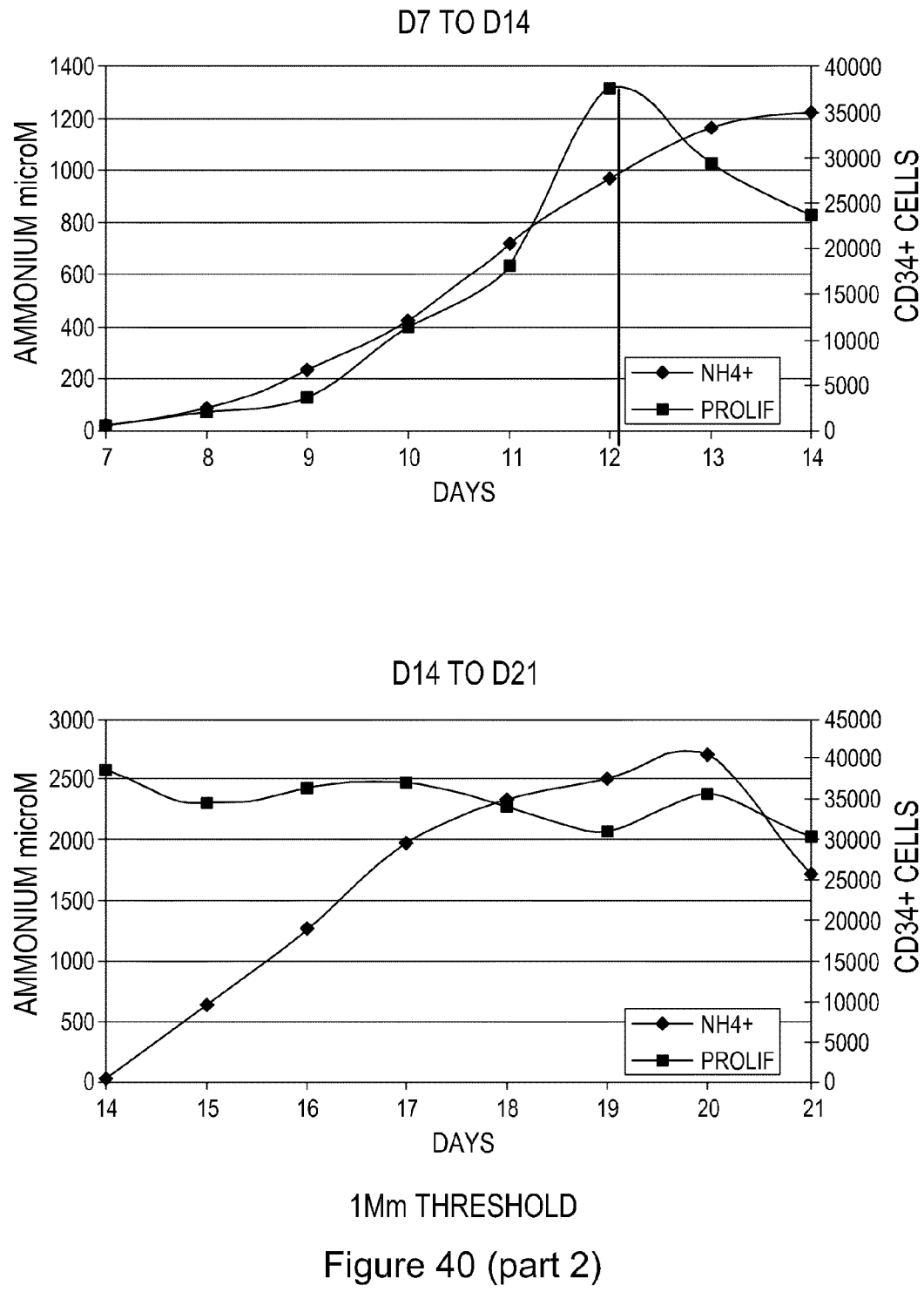
1Mm THRESHOLD
Figure 40 (part 2)

Central Points
Temp = 37 °C    DT° =      1,2 °C
$pCO_2$ = 5 %    $DCO_2$ =   2.5 %
$pO_2$ = 10.5 %  $DO_2$ =   10.5 %

$2^3$ three variables or factors

| | % CO2 | % O2 | T° |
|---|---|---|---|
| D0 ⇔ D8 | 4.8 | 7.1 | 37.5 |
| D8 ⇔ D11 | 6.8 | 16.15 | 36.9 |
| D11 ⇔ D15 | 7.5 | 16.15 | 35 |

Figure 43

ERYTHROCYTES DIFFERENTIATED IN VITRO FROM NANOFIBER EXPANDED CD133+ CELLS

RELATED APPLICATIONS

This continuation-in-part application claims the benefit of the filing date of U.S. application Ser. No. 11/975,492, filed Oct. 18, 2007, which itself claims priority to U.S. Application No. 60/852,598, filed Oct. 18, 2006, and this continuation-in-part application claims the benefit of the filing date of U.S. Provisional Patent Applications 61/010,917, filed Jan. 10, 2008 and 61/190,544, filed Aug. 28, 2008. The entire teachings of all of these application are incorporated by reference herein.

STATEMENT REGARDING FEDERALLY SPONSORED RESEARCH OR DEVELOPMENT

This invention was made with government support under R01HL083008-01 awarded by NIH/NIBIB. The government has certain rights in the invention.

BACKGROUND

Atherosclerotic cardiovascular disease is a leading cause of morbidity and mortality in the industrialized western hemisphere. Coronary artery disease, the pathologic process of arterial luminal narrowing by atherosclerotic plaque resulting in obstruction of blood flow to the heart, accounts for about half of the deaths. Although catheter-based revascularization or surgery-based treatment approaches have been successful in restoring blood flow to ischemic myocardium in the majority of cases, the treatments are inadequate for a significant number of patients who remain incompletely revascularized. The ramifications of treatment limitations may be significant in patients who have large areas of ischemic, but viable myocardium jeopardized by the impaired perfusion supplied by vessels that are poor targets for conventional revascularization techniques. Treatment alternatives, including mechanical approaches such as percutaneous transluminal myocardial revascularization, and the like, have not produced encouraging results. Gene therapy using adenoviral vectors to augment cytokine production and, therefore, promote angiogenesis has shown promise, but this therapy has limitations and has not yet emerged as the optimal treatment for these patients. Therefore, therapeutic angiogenesis has attracted many researchers attempting to discover a way to circumvent the burden of chronic myocardial ischemia.

Atherosclerosis of the extremities is a leading cause of occlusive arterial disease of the extremities in patients over age 40. Peripheral vascular occlusive disease and its complications, including ulcers and even necrosis of the affected limb, is also common. Although percutaneous transluminal angioplasty and aorto-bifemoral bypass procedures are associated with acceptable morbidity and mortality risk and are usually initially successful, these interventions have not been shown to be effective long-term.

In an effort to provide treatment for myocardial ischemia and/or peripheral vascular occlusive disease, a number of angiogenesis techniques are now in clinical trial, including gene therapy and the use of growth factors such as vascular endothelial growth factor (VEGF) or basic fibroblast growth factor (bFGF) to induce or augment collateral blood vessel production. For optimal therapeutic outcome, these techniques rely on the availability of a resident population of mobilizable and hormone responsive vascular endothelial cells in the patient's circulation. However, an age-related diminution of vascular endothelial cell number and function has been observed in adults. In particular, in older patients who are most likely to suffer from vascular problems, both central (i.e. coronary) and peripheral, the number of hormone responsive endothelial cells is reduced and the number of dysfunctional endothelial cells is increased. Moreover, administration of cytokines to mobilize sufficient patient-derived responsive cells may worsen cardiovascular pathophysiology secondary to leukocytosis and/or activation of pro-coagulant processes.

Therefore, an alternative therapy, that of supplying an exogenous source of endothelial precursor cells (EPCs), may be optimal for cellular therapeutics to enhance vasculogenesis and collateralization around blocked/narrowed vessels to relieve ischemia. Clinical use of autologous patient-derived sources of stem cells is advantageous to avoid potential adverse allogeneic immune reactivity; however, the disadvantages include the need to subject the patient to stem cell collection at a time of active vascular disease.

Therefore, there is still a need to develop treatment modalities for both myocardial ischemia and peripheral vascular disease that can promote vasculogenesis in the ischemic tissue.

Transfusion of incompatible ABO blood units is the major cause of transfusion-induced fatalities.14,15 An automated red blood cell production system where the majority of units are group O (Universal donor) could theoretically solve many complications.16

Advanced medical support requirements for military personnel have become an ever growing challenge with the advent of smaller more widespread deployments in the war on terrorism. A recurring theme in management of the advanced theater trauma patient is the pressing need to replenish the patient's circulating volume of blood with universal donor oxygen carrying erythrocytes in order to improve survival. Applicants disclosures relating to erythrocyte progenitor manufacturing technology that will result in a technologically feasible manufacturing solution to the pressing need for constant supply of universal donor red blood units in advance military operations. There is an increasing interest in alternative sources of transfusable blood products due to tighter regulations imposed that leads to increasingly stringent eligibility criteria for blood donors, Thus, there is an ongoing interest in the field to produce fully functioning red blood cells ex vivo. New blood substitutes based on cell-free hemoglobin solutions have had serious problems during clinical trials 21. Moreover, cellular hemoglobin-based blood substitutes are not suitable due to their short circulatory life span of less than 48 hours, compared to 42-120 days for human red blood cells.

It has been well documented that hematopoietic stem cells generate progenitor cells that undergo terminal differentiation, resulting in mature circulating blood cells. 22. Prior culturing techniques for expanding stem cells use a variety of approaches including co-culture with bone marrow stromal cells which rarely show more than 3-5 fold increase in cell number. Clinical grade media-only based culturing systems are inefficient due to the requirement for multiple media changes, and have demonstrated difficulty maintaining the starting populations in undifferentiated states. In addition, co-culture methods have not been shown to effectively produce clinical grade stem cells.23-27 However, the failure of erythroid development, which normally culminates in mature enucleated reticulocytes and red blood cells in vitro or ex vivo is articulated to the need for cell-cell interactions. 6-11 Recently, Giarratana et al 12 describe a promising technology that permits for the first time both the extensive expansion of CD34+ stem cells and their total conversion ex vivo into mature enucleated red blood cells. Although the work of Giarratana et al. is a significant milestone in red blood cell engineering, its practical implications are limited due to the constraints in obtaining enough erythrocyte progenitor cells using the co-culture techniques. In addition, the complex engineering needed to implement the three-step protocol would make each unit of blood produced prohibitively expensive. Thus, developing a practical method for producing red blood cells on a scale that is robust and economical would be ideal.

BRIEF SUMMARY OF THE INVENTION

In certain aspects the invention provides a method for expanding CD133+ cells, comprising providing CD133+ cells and culturing said CD133+ cells on polymeric nanofibers. In certain embodiments, said expansion comprises increasing the number of CD133+ cells by at least 300-fold. In certain embodiments, the CD133+ cells are CD133+CD34− cells, CD133+CD34+ cells, or combinations thereof. In certain embodiments, the CD133+ cells are CD133+CD34+KDR-CXCR4− cells. In certain embodiments, at least 10% of the total cells are CD133+. In certain embodiments, said expansion occurs in about 10 days. In certain embodiments, said polymeric nanofibers are random nanofiber meshes or films. In certain embodiments, said polymeric nanofibers are aligned nanofiber meshes or films. In certain embodiments, said polymeric nanofibers are polyethersulfone (PES) meshes or films. In certain embodiments, said polymeric nanofibers are surface-conjugated with functional groups. In certain embodiments, wherein said functional groups are selected from the group consisting of: hydroxyl, carboxyl, and amino groups. In certain embodiments, said polymeric nanofibers are surface-conjugated with fibronectin. In certain embodiments, said CD133+ cells are mammalian cells. In certain embodiments, said CD133+ cells are human cells. In certain embodiments, the CD133+ cells are isolated from umbilical cord blood, bone marrow or peripheral blood or combinations thereof. In certain embodiments, the CD133+ cells are enriched from umbilical cord blood, bone marrow or peripheral blood or combinations thereof. In certain embodiments, the composition comprises CD133+ enriched at least 2-fold over bone marrow mononuclear cells. In certain embodiments, the expanded CD133+ cells are recultured for further expansion.

In certain aspects the invention provides a method further comprising directing differentiation of the CD133+ cells. In certain embodiments, said CD133+ cells differentiate into smooth muscle cells. In certain embodiments, said CD133+ cells differentiate into endothelial cells. In certain embodiments, said CD133+ cells differentiate into red blood cells. In certain embodiments, the red blood cells are O Rh negative cells. In certain embodiments, said CD133+ cells differentiate into platelets. In certain embodiments, the total number of cells is increased by about 4500-fold. In certain embodiments, differentiation occurs in about 6-28 days. In certain embodiments, directing differentiation comprises sequentially exposing cells to media comprising: a) Stem Cell Growth Factor 1, Erythropoietin and Interleukin 3 and b) EPO. In certain embodiments, directing differentiation comprises sequentially exposing cells to media comprising: a) Stem Cell Growth Factor 1, Erythropoietin and Interleukin 3, b) SCF and EPO and c) EPO.

In certain embodiments, the CD133+ cells or differentiated cells express a recombinant transgene. In certain embodiments, the CD133+ cells or differentiated cells express a recombinant proangiogenic growth factor. In certain embodiments, the proangiogenic growth factor is VEGF164, PDGF-BB, or both. In certain embodiments, VEGF164 and PDGF-BB are expressed in a bicistronic co-delivery vector.

In certain aspects the invention provides a method further comprising administering a composition comprising said CD133+ cells to a subject in need thereof. In certain embodiments, said subject in need thereof is suffering from a condition selected from the group consisting of: ischemia, diabetes, a wound in need of healing, a need for tissue or organ replacement, a need for dialysis, need for blood transfusion, a blood condition, blood disease and blood loss. In certain embodiments, the CD133+ cells are autologous to said subject. In certain embodiments, the CD133+ cells are allogeneic to said subject. In certain embodiments, the CD133+ cells are administered by infusion into an artery. In certain embodiments, the composition comprises a matrix in which the CD133+ cells are embedded. In certain embodiments, the matrix comprises polyethylene glycol (PEG), collagen, fibrin, fibronectin, gelatin, poly-lysine, laminin, heparan sulfate proteoglycan, entactin, elastin, nidogen, hyaluronin, or a combination thereof. In certain embodiments, the fibrin matrix is polymerized from a solution that contains from about 50 mg/ml to about 400 mg/ml fibrinogen and from about 250 units/mL to about 2000 units/mL thrombin. In certain embodiments, the CD133+ cells are held in a solution comprising buffered saline for 6-36 hours prior to administering to the subject. In certain embodiments, the composition further comprises soluble human fibronectin, hyaluronan, type I collagen, fibrin, gelatin, poly-lysine, laminin, heparan sulfate proteoglycan, entactin, elastin, nidogen, or a combination thereof. In certain embodiments, the method further comprises administering to the subject a cytokine, chemokine or growth factor. In certain embodiments, the growth factor is PDGF or VEGF. In certain embodiments, the method further comprises pre-incubating said CD133+ cells with a cytokine, chemokine, or growth factor before administering said CD133+ cells to the subject. In certain embodiments, the growth factor is PDFG or VEGF. In certain embodiments, the method further comprising directing differentiation in any of the ways described above of said CD133+ cells before administering said CD133+ cells to the subject. In certain embodiments, the method further comprises administering to the subject an anticoagulant. In certain embodiments, at least 10% of cells in the composition are CD133+ cells. In certain embodiments, the CD133+ cells are isolated from umbilical cord blood, bone marrow or peripheral blood or combinations thereof. In certain embodiments, the CD133+ cells are enriched from umbilical cord blood, bone marrow or peripheral blood or combinations thereof. In certain embodiments, the composition comprises CD133+ enriched at least 2-fold over bone marrow mononuclear cells. In certain embodiments, the CD133+ cells are recultured for further expansion prior to administering to the subject. In certain embodiments, administering the composition to the subject consists of a single administration of the composition to the subject. In certain embodiments, administering the composition to the subject consists of multiple administrations of the composition to the subject. In certain embodiments, administering the composition reduces, delays or eliminates the need for surgical or pharmaceutical intervention. In certain embodiments, administering the composition increases by at least 25% the likelihood that the subject will survive over a one-year period following treatment.

In certain aspects the invention provides a bioreactor system comprising polymeric nanofibers and CD133+ cells. In certain embodiments, cells are contacted with one or more of: SCF, IL-3, EPO, and TPO. In certain embodiments, said cells are expanded. In certain embodiments, said system directs differentiation after expansion.

In certain aspects the invention provides a method of expanding CD133+ cells, comprising: (a) providing a population of cells including CD133+ cells, (b) purifying CD133+ cells from the population, (c) providing a bioreactor system containing polymeric nanofibers, and (d) culturing said CD133+ cells in said bioreactor. In certain embodiments, said CD133+ cells are expanded about 300-fold. In certain embodiments, said method further comprises directing differentiation of the CD133+ cells. In certain embodiments, said CD133+ cells differentiate into erythrocytes. In certain embodiments, said CD133+ cells differentiate into platelets. In certain embodiments, said CD133+ cells differentiate into smooth muscle cells. In certain embodiments, said CD133+ cells differentiate into endothelial cells. In certain embodiments, the total number of cells is increased by at least 4500-fold. In certain embodiments, said differentiation occurs in about 6-28 days. In certain embodiments, said expansion and differentiation occur in about 28 days. In certain embodiments, the method further comprises administering a composition comprising said CD133+ cells to a subject in need thereof. In certain embodiments, said subject in need thereof is suffering from a condition selected from the group consisting of: ischemia, diabetes, a wound in need of healing, a need for tissue or organ replacement, a need for dialysis, need for blood transfusion, a blood condition, blood disease and blood loss. In certain embodiments, cellular waste production is optimized during culturing. In certain embodiments, cellular waste is selected from the group consisting of ammonia and lactic acid. In certain embodiments, $CO_2$ levels, $O_2$ levels and temperature are optimized during culturing. In certain embodiments, $CO_2$ levels, $O_2$ levels and temperature are re-optimized during different phases of culturing.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13. Functionality of NANEX RBCs. Day 15 differentiated erythrocytes were examined for deformability and enzyme content.

FIG. 16. Blood Group Ag Expression. RhD and A antigen expression were examined on differentiated RBCs cultured to Day 0, 4, 8, 11, 14 and 16.

FIG. 17. In vivo Fate of cRBCs. Labeled 30×10$^6$ Day 15 differentiated RBCs were delivered via retro-orbital injection into each NOD/SCID mouse and analyzed for LDS and the label CFSE.

FIG. 22. Controlling Cues Presented by Nanofibers.

FIG. 30. day 0. FIG. 31. day 6. FIG. 32. day 9. FIG. 33. day 12. FIG. 34. day 16. FIG. 35. day 19. FIG. 36. day 21 using Protocol A. FIG. 37. day 23 using Protocol A.

FIG. 38. NANEX RBC Production. A comparison was made between total cell production and RBC production using Protocols A and B.

FIG. 40. Ammonia is a Limiting Factor for Proliferation. Analysis of ammonium levels and proliferation were analyzed.

FIG. 43. Computer Defined Optimal Values for Proliferation Phase.

DETAILED DESCRIPTION OF THE INVENTION

Overview

Figure 1:
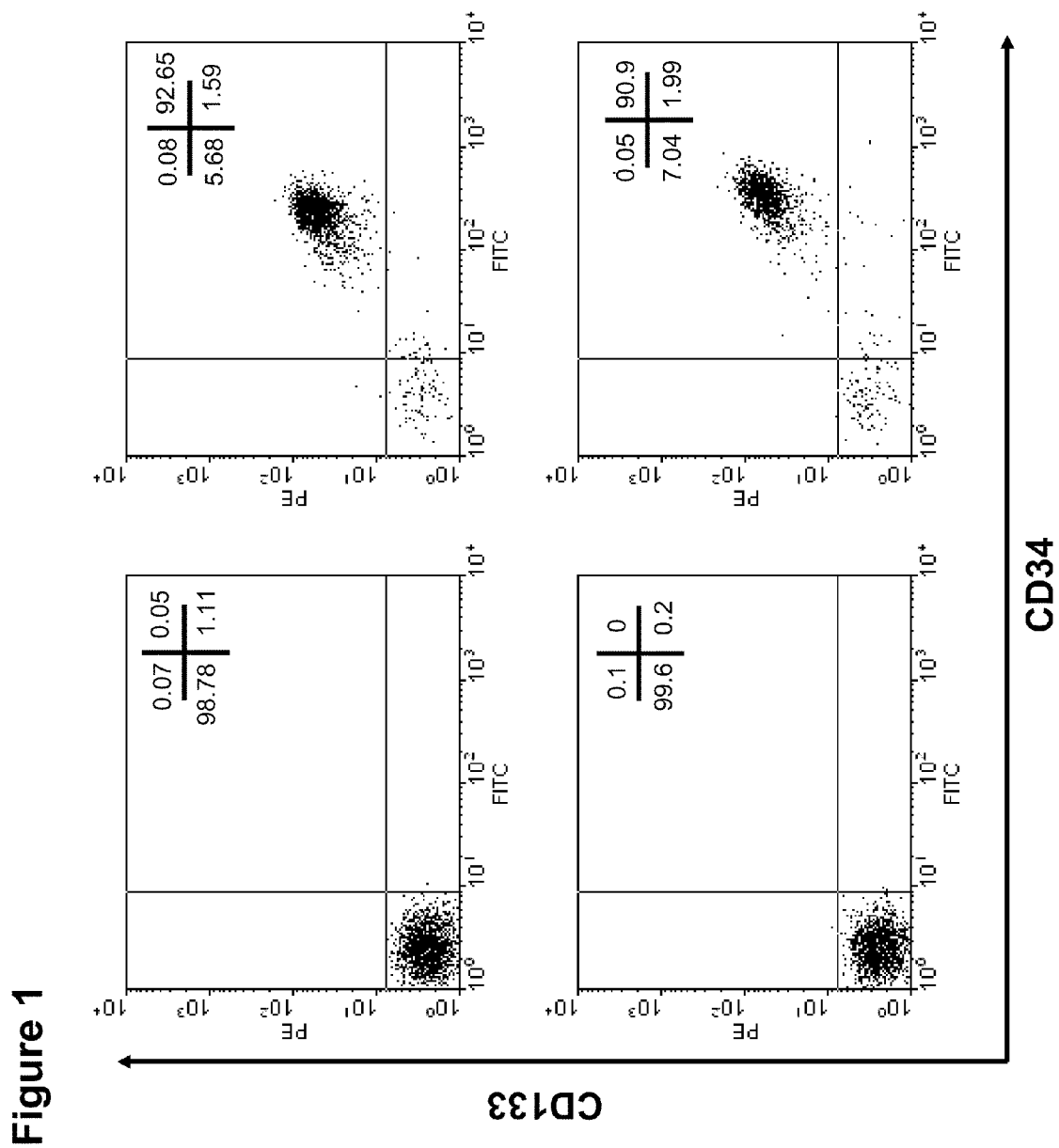
FIG. 1. Isolation of cord blood derived stem cells and ex-vivo expansion on nanofiber scaffold. CD133 positive cells were isolated from human umbilical cord blood using autoMACS machine and reagents as described in Materials and Methods. Flowcytometric analysis was performed for the evaluation of purity. Right panel indicates the purity is more than 90% and left panel is the isotype control. This is representative of at least six separate cord samples evaluated.
Figure 2:
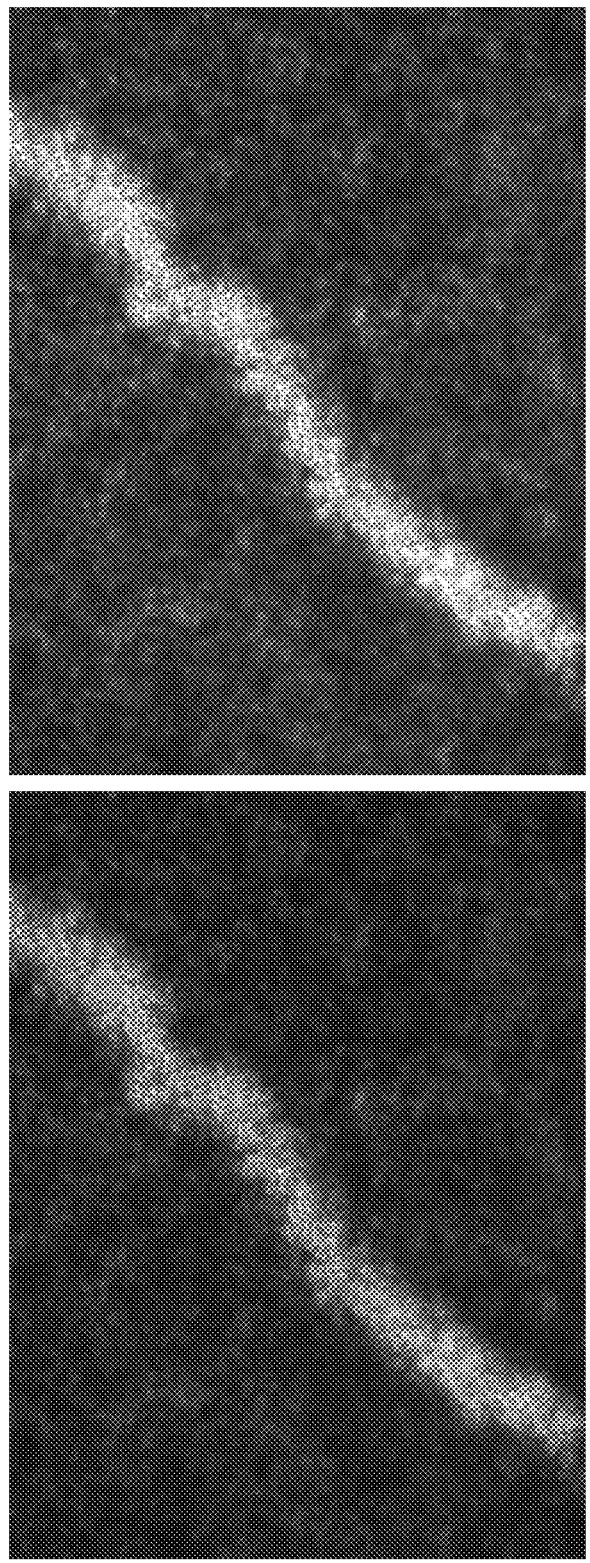
FIG. 2 depicts the appearance of AC133+ cells plated on polymeric nanofibers by light microscopy.

One major obstacle to achieving successful vasculogenesis is the sparse populations of endothelial progenitor cell (EPC) in bone marrow (BM) and peripheral circulation (1, 2), further compounded by even reduced numbers and compromised potential of EPCs in aged patients and adults in disease states (3). The self-renewal, proliferation and differentiation of HSCs are tightly regulated in vivo by an array of signals emanating from their microenvironment, termed the HSC niche (4). The extracellular matrix (ECM) components in HSC niche are an integral part of the signals. Besides regulating the local presentation of growth factors, they provide the adhesive interactions or anchorages for HSCs, which are of critical importance to the survival, homing and lodging behavior of HSCs and also facilitate their interactions with stromal cells (5, 6), (7). Human UCB CD34+ cells cultured on aminated nanofibers could be efficiently expanded after 10 days of culture in serum-free medium (8).

Two major approaches were taken to expand human stem cells, either a biological approach or a biomaterials approach (19). In the biological approach, stromal layers are very important. The stromal layer comprises a mixture of fibroblasts, macrophages, adipocytes, endothelial cells and reticular cells that can provide a large portion of the HSC niche of secreted biochemical factors. The stromal layer is not defined, and it is difficult to generate the stromal layer in a reproducible fashion, which therefore renders the expansion outcome less predictable. The use allogeneic cell sources is less desirable due to potential immunologic complications (20), (21). There is also possible complication that the stromal layer may produce negative regulators of hematopoiesis such as transforming growth factor TGF-β and chemokines (4), (19).

As an alternative, stromal-free suspension culture has been rapidly adopted for HSC expansion due to their chemically defined nature. This method involves the use of various combinations of growth factors and cytokines to substitute for the regulatory signals provided by stromal cells (22), (23), (24). Although these suspension cultures offer the obvious advantage of simplicity, the expansion outcomes are less impressive (25), (26). It has been increasingly recognized that suspension culture lacks the critical HSC-extracellular matrix (ECM) interaction (27). Therefore, the new biomaterials approach aims to provide adhesion support and topographical features of the BM microenvironment.

Vascular endothelial growth factor (VEGF) and Platelet derived growth factor (PDGF) are integral mediators of vasculogenic responses to ischemia. Several studies have demonstrated the participation of these two growth factors in the angiogenic process; with VEGF playing a key role mainly initiating the formation of new blood vessels and PDGF being involved in the maintenance of these vessels (10), (11), (12), (13), (9), (30), (31), (32), (33), (34). Recently, Hao et al. have studied the effect of phVEGF-$A_{164}$, phPDGF-BB, or a combination of the two, injected into the myocardial infarct border zone in rats 7 days after ligation of the coronary left anterior descending artery (35). The results from this study indicated that phVEGF-$A_{164}$ increased capillary density more than phPDGF-BB, and phPDGF-BB preferentially stimulated arteriolar growth. The combination increased both capillaries and arterioles but did not enhance angiogenesis any more than single plasmid treatments did. VEGF-$A_{164}$ and the combination of phVEGF-$A_{164}$ and phPDGF-BB counteracted left ventricular dilatation after 1 week but did not counteract further deterioration (35). These results indicate that direct application of PDGF or VEGF does not augment ischemic repair and more controlled release of these growth factors with stem cells transplantation may have beneficial effect on ischemic repair. Bicistronic vectors in which both the VEGF-$A_{164}$ and PDGF-BB under IRS promoter control (coupled VIP) have been transfected into myoblasts with resultant increased neovascularization in vivo attained.

Transfusion therapy has been an integral part of military medicine. As the most needed and vital component of blood, red blood cells (RBCs) are the most transfused blood product in the battlefield trauma care and more than 54,000 units of RBCs are transfused every year in military hospitals. However, donor RBC unit supplies in the military are limited in the battlefield environment due to the inherent liabilities of the donor system coupled with the global nature of U.S. military operations. The current system is donation dependent and primarily CONUS sourced, which poses significant logistic and cost challenges. In addition, several recent studies suggest that the storage lesions can have deleterious effects in recipients.

An effective development of manufacturing capabilities to grow universal donor "O-negative" red blood units would allow direct application in acute care settings of dramatic blood loss, without violating the FDA's concerns involving patient consent. This solution is both technologically attainable and desirable from a clinical and regulatory standpoint. This is be the focus of Applicants' methods to generate RBCs from hematopoietic progenitor cells using ex vivo nanofiber-based expansion.

Close proximity blast injury continues to be the most common cause of life threatening injury to military soldiers in many advanced theater operations due to the increase in terrorist attacks in conflict regions and occupied territories. Blast injuries from these strikes are devastating and can quickly overwhelm the available medical resources of both military and civilian facilities. Recently a team at Camp Pendleton looked at 18 consecutive close proximity blast injury patients who were alive when presented to a forward deployed surgical unit in Iraq. Of the three likely predictive factors of mortality, sustained hypotension (from severe blood loss) was a greater predictor of death than multiple long bone fractures, or penetrating head injury. One hundred percent of this small cohort of injured that presented with sustained hypotension died, while those without sustained hypotension survived. (29) There is clearly a need in the art for the ex vivo production of large numbers of red blood cells.

UCB stem cells are more proliferative and are immunologically more naïve than BM or PB stem cells. Clinical studies in leukemia have shown that CB needs less HLA matching for graft survival. Kelly et al found CB transplants in Leukemia demonstrated recipient conversion to donor blood type, indicating the donor unit converting to complete production of the recipient's hematopoietic system 30. The capacity of these CD133+ and CD34+ progenitor cells to differentiate down the erythrocyte progenitor lineage reinforces these cells as appropriate starting populations for Blood Pharming.31,32

Current culturing techniques for expanding stem cells use a variety of approaches including, co-culture with bone marrow stromal cells which rarely show more than 3-5 fold increase in cell number. Additionally, current clinical grade media-only based culturing systems are inefficient due to the requirement for multiple media changes, and have difficulty maintaining the starting populations in undifferentiated states (Aastorm, Viacell, and Athersys). Finally, co-culturing methods have not effectively produced clinical grade stem cells 33.

Recently, Giarratana et al (12,13) have described large-scale ex vivo production of mature human red blood cells (RBCs) from hematopoietic stem cells of diverse origins. By mimicking the marrow microenvironment through the application of cytokines and co-culture on stromal cells, they have coupled substantial amplification of CD34 (+) stem cells (up to $1.95 \times 10^{(6)}$-fold) with 100% terminal differentiation into fully mature, functional RBCs. These cells also survived and showed a functional RBC differentiation in nonobese diabetic/severe combined immunodeficient mice. Even though, this co-culture system of producing 'cultured RBCs' lends itself to a fundamental analysis of erythropoiesis and provides a simple in-vitro model for studying important human viral or parasitic infections that target erythroid cells, further development of large-scale production of cultured RBCs that could be readily transferable will have implications for gene therapy, blood transfusion and tropical medicine (12, 34-39). Giarratana et al have used an immortalized murine stromal cell line MS5 to co-culture the erythrocyte progenitors. However, our Nanex system does not need to co-culture with stromal cells reducing allo-contamination potential. In addition, Nanex cell expansion culture can be used as automatic self selection of cells toward the erythroid lineage as the differentiating cells detach from the scaffold and become suspended, facilitating an easy removal (i.e. simple transfer of the detached cells out of the scaffold containing compartment of the bioreactor, while keeping the majority of adherent cells in a self renewing system.

Previously, Cytomatrix had reported the ability to differentiate CD34+ hematopoietic progenitor cells toward the erythrocyte lineage using stem cell factor (500 pg/ml) or TPO (500 pg/ml) utilizing their CellFoam Biomatrix. They reported total cell (TC) culture expansion efficiency of 375-fold and erythrocyte expansion 555-fold after 4 weeks of culturing. (42nd annual meeting of the ASH, 2000)

DEFINITIONS

For convenience, certain terms employed in the specification, examples, and appended claims, are collected here. Unless defined otherwise, all technical and scientific terms used herein have the same meaning as commonly understood by one of ordinary skill in the art to which this invention belongs.

The articles "a" and "an" are used herein to refer to one or to more than one (i.e., to at least one) of the grammatical object of the article. By way of example, "an element" means one element or more than one element.

The term "including" is used herein to mean, and is used interchangeably with, the phrase "including but not limited" to.

The term "or" is used herein to mean, and is used interchangeably with, the term "and/or," unless context clearly indicates otherwise.

The term "such as" is used herein to mean, and is used interchangeably, with the phrase "such as but not limited to".

Nanofiber Compositions

The invention pertains to methods and compositions for the expansion and differentiation of stem cells. The instant methods rely on the isolation of stem cells from any of a number of sources and the subsequent use of the compositions and methods of the instant invention to expand and/or differentiate these stem cells. Stem cells can be isolated from any of a number of sources and techniques known to those of skill in the art. For example, U.S. Pat. No. 5,061,620 describes a substantially homogeneous human hematopoietic stem cell composition and the manner of obtaining such composition.

In certain embodiments, cells are cultured on nanofiber film. In certain embodiments, cells are cultured on nanofiber mesh. In certain embodiments, cells are cultured on film and mesh. In certain embodiments, the nanofiber film and mesh are those described in US Patent Application Publication No. 20080153163, herein incorporated by reference in its entirety. In certain embodiments, CD133+ cells are cultured on unmod., COOH and OH nanofiber meshes and films. In certain embodiments, CD133+ cells are cultured on TCPS surface.

In certain embodiments, there are surface bound hematopoietic growth factors (HGFs). In certain embodiments, the matrix bound growth factors will mimic the native presentation pattern of the cytokines in BM during early hematopoiesis, where the cytokines interact with HSCs in a membrane bound format.

In certain embodiments, HGFs are directly conjugated to the polymer fibers. In certain embodiments, multiple cytokines are conjugated to the same set of fibers. In certain embodiments, multiple cytokines are conjugated to different fibers. In certain embodiments, the fibers are arranged into defined patterns. In certain embodiments, the fibers are conjugated to fibronectin.

The electrospun nanofibers used in the methods and compositions of the invention can be natural or synthetic. In one embodiment, the electrospun nanofibers are comprised of natural polymers. Exemplary natural polymers include cellulose acetate (CA), chitin, chitosan, collagen, cotton, dextran, elastin, fibrinogen, gelatin, heparin, hyaluronic acid (HA), poly 3-hydroxybutyrate-co-3-hydroxyvalerate (PHBV), regenerated cellulose (RC), silk, and zein.

In one embodiment, the electrospun nanofibers are made of degradable or non-degradable synthetic polymer material. Exemplary degradable polymers include poly(.epsilon.-caprolactone) (PCL), poly(.epsilon.-caprolactone-co-ethyl ethylene phosphate) (PCLEEP), poly(lactic acid) (PLA), poly(lactic-co-glycolic acid) (PLGA), poly(lactic acid-co-.epsilon.-caprolactone) (PLACL), and polydioxanone (PDO). Exemplary non-degradable polymers include poly acrylamide (PAAm), poly acrylic acid (PAA), poly acrylonitrile (PAN), poly amide (Nylon) (PA, PA-4,6, PA-6,6), poly aniline (PANI), poly benzimidazole (PBI), poly bis(2,2,2-trifluoroethoxy) phosphazene, poly butadiene (PB), poly carbonate (PC), poly ether amide (PEA), poly ether imide (PEI), poly ether sulfone (PES), poly ethylene (PE), poly ethylene-co-vinyl acetate (PEVA), poly ethylene glycol (PEG), poly ethylene oxide (PEO), poly ethylene terephthalate (PET), poly ferrocenyldimethylsilane (PFDMS), poly 2-hydroxyethyl methacrylate (HEMA), poly 4-methyl-1-pentene (TpX), poly methyl methacrylate (pMMA), poly p-phenylene terephthalamide (PPTA), poly propylene (PP), poly pyrrole (PPY), poly styrene (PS), polybisphenol-A sulfone (PSF), poly sulfonated styrene (PSS), Styrene-butadiene-styrene triblock copolymer (SBS), poly urethane (PU), poly tetrafluoro ethylene (PTFE), poly vinyl alcohol (PVA), poly vinyl carbazole, poly vinyl chloride (PVC), poly vinyl phenol (PVP), poly vinyl pyrrolidone (PVP), and poly vinylidene difluoride (PVDF). A preferred synthetic polymer is polyethersulfone (PES).

The electrospun nanofiber compostions of the invention can be made of any one of polymers identified herein. The electrospun nanofiber compostions of the invention can also be made of any combination of the polymers identified herein.

Electrospun matrices can be formed of electrospun fibers of synthetic polymers that are biologically compatible. The term "biologically compatible" includes copolymers and blends, and any other combinations of the forgoing either together or with other polymers. The use of these polymers will depend on given applications and specifications required. A more detailed discussion of these polymers and types of polymers is set forth in Brannon-Peppas, Lisa, "Polymers in Controlled Drug Delivery," Medical Plastics and Biomaterials, November 1997, which is incorporated herein by reference.

The compounds to be electrospun can be present in the solution at any concentration that will allow electrospinning. In one embodiment, the compounds may be electrospun are present in the solution at concentrations between 0 and about 1.000 g/ml. In another embodiment, the compounds to be electrospun are present in the solution at total solution concentrations between 10-15 w/v % (100-150 mg/ml or 0-0.1 g/L).

The compounds can be dissolved in any solvent that allows delivery of the compound to the orifice, tip of a syringe, under conditions that the compound is electrospun. Solvents useful for dissolving or suspending a material or a substance will depend on the compound.

By varying the composition of the fibers being electrospun, it will be appreciated that fibers having different physical or chemical properties may be obtained. This can be accomplished either by spinning a liquid containing a plurality of components, each of which may contribute a desired characteristic to the finished product, or by simultaneously spinning fibers of different compositions from multiple liquid sources, that are then simultaneously deposited to form a matrix. The resulting matrix comprises layers of intermingled fibers of different compounds. This plurality of layers of different materials can convey a desired characteristic to the resulting composite matrix with each different layer providing a different property, for example one layer may contribute to elasticity while another layer contributes to the mechanical strength of the composite matrix. These methods can be used to create tissues with multiple layers such as blood vessels.

The electrospun nanofiber has an ultrastructure with a three-dimensional network that supports cell expansion, growth, proliferation, and/or differentiation. This three dimensional network is similar to the environment where many of these stem cells naturally occur, e.g., in bone marrow. The spatial distance between the fibers plays an important role in cells being able to obtain nutrients for growth as well as for allowing cell-cell interactions to occur. Thus, in various embodiments of the invention, the distance between the fibers may be about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 10 microns, 10 microns, 50 microns, about 100 microns, about 150 microns, about 200 microns, about 250 microns, about 300 microns, about 350 microns, about 400 microns, about 450 microns, or about 500 microns. In various embodiments the distance between the fibers may be less than 50 nanometers or greater than 500 microns and any length between the quoted ranges as well as integers.

Additionally, in various embodiments of the invention, the fibers can have a diameter of about 50 nanometers, about 100 nanometers, about 150 nanometers, about 200 nanometers, about 250 nanometers, about 300 nanometers, about 350 nanometers, about 600 nanometers, about 750 nanometers, about 800 nanometers, about 850 nanometers, about 900 nanometers, about 950 nanometers, about 1000 nanometers (1 micron), 50 microns, about 100 microns, about 150 microns, about 200 microns, about 250 microns, about 300 microns, about 350 microns, about 400 microns, about 450 microns, or about 500 microns, or the diameter may be less than 50 nanometers or greater than 500 microns and any diameter between the quoted ranges as well as integers. A preferred fiber diameter is between 100-700 nm.

The pore size in an electrospun matrix can also be controlled through manipulation of the composition of the material and the parameters of electrospinning. In some embodiments, the electrospun matrix has a pore size that is small enough to be impermeable to one or more types of cells. In one embodiment, the average pore diameter is about 500 nanometers or less. In another embodiment, the average pore diameter is about 1 micron or less. In another embodiment, the average pore diameter is about 2 microns or less. In another embodiment, the average pore diameter is about 5 microns or less. In another embodiment, the average pore diameter is about 8 microns or less. Some embodiments have pore sizes that do not impede cell infiltration. In another embodiment, the matrix has a pore size between about 0.1 and about 100 .mu.m.sup.2. In another embodiment, the matrix has a pore size between about 0.1 and about 50 .mu.m.sup.2. In another embodiment, the matrix has a pore size between about 1.0 .mu.m and about 25 .mu.m. In another embodiment, the matrix has a pore size between about 1.0 .mu.m and about 5 .mu.m.

The mechanical properties of the matrix or core will depend on the polymer molecular weight and polymer type/mixture. It will also depend on orientation of the fibers (preferential orientation can be obtained by changing speed of a rotating or translating surface during the fiber collection process), fiber diameter and entanglement. The cross-linking of the polymer will also effect its mechanical strength after the fabrication process. The electrospun nanofiber core can be comprised of parallel or randomly oriented fibers.

In certain embodiments of the invention, a polymer is grafted onto the electrospun nanofiber core. Exemplary polymers that can be grafted onto the electrospun core include, but are not limited to, polymers having functional groups which can be initiated by free radicals, e.g., free radicals formed on the surface of the electrospun core. Exemplary grafted polymers include poly(acrylic acid) and derivatives and copolymers thereof, e.g., polymethacrylic acid and poly(acrylic acid-co-hydroxyethylmethacrylic acid), polyallylamine and derivatives and copolymers thereof.

In further embodiments of the invention the polymers grafted on the electrospun nanofiber core are derivatized. In general, the polymers are derivatized so that cells, e.g., stem cells, are better able to interact with the compositions of the invention. In one embodiment, the polymers are derivatized to have a positive charge. In another embodiment, the polymers are derivatized to have a negative charge. Exemplary derivatives include carboxylic, hydroxyl and amino moieties.

In other embodiments, the polymers are derivatized with a biological agent, e.g., a nucleic acid, peptide or polypeptide. In exemplary embodiments, the peptide or polypeptide is a cell adhesion peptide or heparin.

In yet further embodiments, the compositions of the invention comprise a spacer molecule between the electrospun nanofiber and the derivatized moiety. The spacer molecule can allow for improved functionality of the compositions of the invention. In exemplary embodiments, the spacer is a ethylene, propylene, butylenes, hexylene moiety.

Expansion of CD133+ Cells

In certain embodiments, there is about a 300 fold expansion of CD133+ cells. In certain embodiments, there is about a 250 fold expansion of CD133+ cells in about a 10-day expansion.

In certain embodiments, a self-renewing progenitor cell nano fiber based culturing system that expands CD133+ progenitor cells about 300 fold in about 10 days.

In certain embodiments, the disclosed methods produce about 4500 fold expansion of total cells. In certain embodiments, the self-renewing progenitor cell nano fiber based culturing system yields about 4500 fold expansion in about 20 days.

In certain embodiments, there is a 5,000 fold expansion of CD133+ cells in about a 20-day expansion. In certain embodiments, at least $10^4$-fold expansion of starting CD133+ progenitor cell population in about 2 weeks are achieved. In certain embodiments, there is a 10,000 fold expansion in about 14 days. In certain embodiments, there is a 10,000 fold expansion of CD133+ cells on the above functionalized nanofibers in about 14-20 days. In certain embodiments, 1 expanded CD133+ cell differentiated to 35 million cells.

In certain embodiments, expansion occurs in less than 10 days of culture. In certain embodiments, expansion occurs after 10 days of culture. In certain embodiments, expansion occurs in about 10 days of culture. In certain embodiments, expansion occurs in about 12, 16, 18 20, 22, 24, 26 or 28 days of culture. In certain embodiments, expansion occurs between 1 to 10 days of culturing. In certain embodiments, expansion occurs between 2 to 10 days, 3 to 10 days, 4 to 10 days, 5 to 10 days, 6 to 10 days, 7 to 10 days, 8 to 10 days, or 9 to 10 of culturing. In certain embodiments, expansion occurs between 10-28 days of culturing. In certain embodiments, expansion occurs between 10-28 days, 10-12 days, 10-14 days, 10-16 days, 10-18 days, 10-20 days, 10-22 days, 10-24 days, or 10-26 days of culturing. In certain embodiments, expansion occurs on a scaffold. In certain embodiments, expansion occurs in culture on nanofiber mesh and/or film. In certain embodiments, expansion occurs in a bioreactor.

Differentiation of CD133+ Cells

In certain embodiments, the present invention discloses methods and a processes to obtain whole blood through the ex vivo expansion and differentiation of stem cells.

One embodiment of the invention is to isolate stem cells from a biologic source such as peripheral blood, umbilical cord blood, bone marrow, and embryonic fluid. A further embodiment of the invention is to spray a nanofiber, incorporated herein, onto a hollow fiber substrate to function as a component in cell culturing. Said stem cells are applied to said nanofiber and are allowed to expand for a period of time. In certain embodiments, cell differentiation media is filtered into said hollow fiber as a delivery method to culture said expanded stem cells, differentiating said stem cells into erythrocytes.

In certain embodiments, cultured cells according to the methods of the application have a significant differentiation commitment towards the myeloblast/monoblast lineage. In certain embodiments, cultured cells according to the methods of the application have a significant differentiation commitment towards the erythrocyte lineage. In certain embodiments, cultured cells according to the methods of the application have a significant differentiation commitment towards platelets. In certain embodiments, 80% or more of nanofiber expanded cells are differentiated to erythrocyte phenotype in about 26 days in liquid culture. In certain embodiments, 80% or more, 90% or more, or 95% or more of nanofiber expanded cells are differentiated to erythrocyte phenotype in about 10, 12, 14, 16, 18, 20, 22, 24 or 28 days in liquid culture. In certain embodiments, expanded cells successfully reconstitute hematopoiesis in at efficiency rates higher than current culturing methods. In certain embodiments, clinical products are generated from a 60 cc initial harvest.

In certain embodiments, 1 PBSC CD133+ cell generates 1-2×$10^5$ cRBC. In certain embodiments, 1 PBSC CD34+ cell generates 1-2×10⁶ cRBC. In certain embodiments, 1 expanded cell generates 0.2-1×10⁷ cRBC. In certain embodiments, 1 expanded cell generates 3.5×10⁷ cRBC. In certain embodiments, 1 CB CD34+ cell generates 2-10×10⁶ cRBC. In certain embodiments, 1 leukapheresis or 1 cord blood can generate in vitro the equivalent of 4 to 10 standard units of packed RBC. In certain embodiments, total cells are expanded about 50,000 fold over about 27 days.

In certain embodiments, CD133+ cells are differentiated in defined medium for RBC production according to UPMC protocol comprising IL3, SCF and EPO. In certain embodiments, IL3 continues until Day 8. In certain embodiments, IL3 continues until Day 9. In certain embodiments, IL3 continues up to about Day 2, 3, 4, 5, 6, 7, 8, 9, 10, 11, 12, 13, 14, 15, 16, 17, 18, 19, 20, 21, 22, 23, 24, 25, 26, 27 or 28. In certain embodiments, SCF is maintained up to Day 11. In certain embodiments, SCF is maintained up to Day 12. In certain embodiments, SCF is maintained up to Day 16. In certain embodiments, SCF is maintained up to about Day 2, 3, 4, 5, 6, 7, 8, 9, 10, 11, 12, 13, 14, 15, 16, 17, 18, 19, 20, 21, 22, 23, 24, 25, 26, 27 or 28. In certain embodiments, EPO is maintained up to about Day 15. In certain embodiments, EPO is maintained up to about Day 16. In certain embodiments, EPO is maintained up to about Day 2, 3, 4, 5, 6, 7, 8, 9, 10, 11, 12, 13, 14, 15, 16, 17, 18, 19, 20, 21, 22, 23, 24, 25, 26, 27 or 28.

In certain embodiments, CD133+ cells are differentiated using feeder systems according to published methods such as those described in, Koury et al. In vitro maturation of nascent reticulocytes to erythrocytes. Blood. 2005 Mar. 1; 105(5): 2168-74. Epub 2004 Nov. 4; Fujimi et al. Ex vivo large-scale generation of human red blood cells from cord blood CD34+ cells by co-culturing with macrophages. Int J. Hematol. 2008 May; 87(4):339-50; Neildez-Nguyen et al. Human erythroid cells produced ex vivo at large scale differentiate into red blood cells in vivo. Nat. Biotechnol. 2002 May; 20(5):467-72; or Giarratana et al. Ex vivo generation of fully mature human red blood cells from hematopoietic stem cells. Nat. Biotechnol. 2005 January; 23(1):69-74. Epub 2004 Dec. 26, all of which are herein incorporated by reference in their entirety.

Strategies to Control RBC Antigen Presentation

Applicants disclose a portable, automated system that produces universal donor O Rh− red blood units that may, for example, be used for advanced theater battlefield trauma care using a renewable source of progenitor cells from O Rh negative donors, eliminating RBC antigen presentation issues associated with prior studies. It is possible that other RBC antigens will be expressed during the culture period, based on the work of others, 16. This may be verified using standard blood bank hemagglutination assays or flow cytometry.

Increasing evidence from human and murine studies suggests that BM and peripheral blood derived CD133+ cells, as well as UCB derived CD133+ cells could readily differentiate to endothelial lineage and contribute to endothelium and other cell types.17,18. It is expected that NANEX expanded CD133+/CD34+ cells will preserve this functional ability and differentiate into enucleated RBC upon stimulation. In addition, the mechanism of erythroblast enucleation has been widely demonstrated. Recent studies have clearly articulated that the cell-cell interaction (via co-culturing) can be eliminated by providing appropriate growth factors and cytokine cocktail in the culture 19,20. As the O Rh(−) Genotype/Phenotype (Universal Donor) should be maintained through the culture and differentiation procedure, one would not anticipate any antigenic change during expansion or differentiation using the NANEX nanofiber culture. It is desirable to achieve a total expansion efficiency of 2×10⁶ fold using 1×10⁶ CD133+/CD34+ starting population. An alternative approach would be to use a higher starting progenitor cell population by resetting T0 to T+10 days to have enough starting cell population.

It may prove beneficial to use routine experimentation to modify additional procedures in order to optimize the method for differentiating nanofiber expanded CD133+/CD34+ progenitor cell into fully mature RBCs. One may make appropriate adjustments to our culture media conditions by including SCF, EPO, IL-3, vascular endothelial growth factor (VEGF) and insulin-like growth factor-II (IGF-II) to obtain fully mature RBCs from expanded cells as described by Miharada et al (19).

Finally, even though the previously reported low levels of HbF (4%) expression after in vivo injection of differentiated cells have clinical benefit, we anticipate that the blood units for military purpose has to have low levels of HbF in starting population of RBC to have a even oxygen uptake. In the case of CB-derived erythrocytes, the % fetal hemoglobin will not be greater than 60%, which would be essentially "trait"-like and should not prove to be a problem physiologically with respect to oxygen transport.

Human UCB CD133+ and CD34+ cells may be cultured on novel aminated nanofibers. These cells can be efficiently expanded by 100- to 200-fold after 10 days of culture in serum-free medium, and the expanded CD34+ cells successfully reconstitute hematopoiesis in NOD/SCID mice at efficiencies higher than that of standard suspension culture on tissue culture plates.1,28 Applicants' evaluation of this novel animated nanofiber system has confirmed that currently >20% of expanded UCB CD133+/CD34+ cells express RBC phenotype. The approach of using nanofiber based ex vivo stem cell expansion technology to generate functional RBC; and potential to make an automated system for production and keeping the self renewing stem cell population in the system is very innovative.

Bioreactors

In certain embodiments, the CD133+ cells are placed in a device to optimize the cell culture parameters allowing cell expansion and maturation. Said device can allow for optimization of oxygen levels, carbon dioxide levels, temperature, pH levels, and the level of cell waste including ammonia or other ammonia related waste products referred to as ammoniac. In certain embodiments, said device allows disposable, elongated, components to be inserted within said device. In certain embodiments, the inserted components are lined with a hollow fiber structure to allow for interlumen access for cell media gas exchange allowing optimization of gaseous levels within the device. In certain embodiments, the nanofiber complex disclosed in Ser. No. 11/975,492 is applied to the fiber structure to create an environment to allow for the expansion and differentiation of hemopoietic and/or precursor stem cells. In certain embodiments, the device creates an environment to allow for media exchange necessary to allow the stem cells to expand and differentiate in an automated system, while maintaining an environment optimal for cell expansion and differentiation as disclosed herein. In certain embodiments, said device allows for continual flow of media necessary for differentiation. Said device contains a mechanism to flush and collect expanded and differentiated cells.

In certain embodiments, the process occurs within a bioreactor specifically designed to allow the exchange or combination of cell media, nanofiber, and hollow fiber environments. Said hollow fiber functions as a scaffold for said nanofiber to provide interlumen access for cell media gas exchange etc. In certain embodiments, CellExpand scaffold is used.

Another embodiment of the invention includes expansion and terminal differentiation of said isolated stem cells within the same bioreactor. In certain embodiments, a bioreactor may be readily used with Nanex system for RBC differentiation of Nanex expanded CD133+/CD34+ hemopoietic progenitor stem cells.

Another embodiment of the invention includes expansion in one bioreactor and terminal differentiation of said isolated stem cells within a separate unconnected bioreactor system.

Another embodiment of the invention includes expansion within one bioreactor system connected to a separate bioreactor system to perform terminal differentiation of said isolated stem cells.

In certain embodiments, there is at least $10^4$-fold expansion of starting CD133+ progenitor cell population in about 2 weeks with at least 5 cycles of self-renewal. In certain embodiments, there is at least $10^5$, $10^6$ or $10^7$-fold expansion of starting CD133+ progenitor cell population in about 2 weeks, 3 weeks or 4 weeks.

In certain embodiments, there is an efficiency rate of at least 85% for the bioreactor-supported differentiation of CFU-E (mid-development red blood cell) to mature enucleated red blood cells. In certain embodiments, there is an efficiency rate of at least 90%, 95%, 96%, 97%, 98%, 99% or 100% for the bioreactor-supported differentiation of CFU-E (mid-development red blood cell) to mature enucleated red blood cells.

In certain embodiments, a portable Bioreactor based automated culture system produces universal donor O-negative red blood units using a renewable source of progenitor cells. In certain embodiments, the Bioreactor Process Flow comprises one or more of the following steps not necessarily in the order listed. In certain embodiments, insert expansion and differentiation chamber containing nanofiber culture surface. In certain embodiments, infuse with expansion medium. In certain embodiments, stabilize temperature and with continuous, sterile gas exchange to the interior culture environment per optimized environmental values. In certain embodiments, infuse with CD133+ cells. In certain embodiments, maintain environment, periodically flushing to collect differentiated cells. In certain embodiments, flush every day. In certain embodiments, after sufficient expansion, flush expansion medium. In certain embodiments, infuse cells with detachment treatment (such as enzyme solution, etc.) to remove remaining cells. In certain embodiments, flush 70-90% suspension volume into differentiation chamber, and re-suspend remaining 10% in expansion chamber with expansion medium. In certain embodiments, flush about 70, 80 or 90% suspension volume into differentiation chamber, and re-suspend the remaining portion in expansion chamber with expansion medium. In certain embodiments, suspend in differentiation medium. In certain embodiments, maintain differentiation chamber until sufficient cells are produced. In certain embodiments, flush and collect media containing detached, differentiated cells. In certain embodiments, the differentiated cells are RBCs.

In certain embodiments, the process is repeated 5 times. In certain embodiments, the process is repeated 5-12 times. In certain embodiments, the process is repeated 12 times. In certain embodiments, the process is repeated 6, 7, 8, 9, 10, or 11 times. In certain embodiments, the process is repeated indefinitely.

In certain embodiments the bioreactor is a staged bioreactor system. In certain embodiments, the combination of liquid suspension culture and 3D perfusion bioreactor modules enables construction of a system that is automated and packaged for use in the field. In certain embodiments, the system uses selective adherence that makes use of the surface properties of hematopoietic cells at various stages of differentiation. In certain embodiments, the entire system is scalable, in that suspension cultures can be adjusted in size for cell concentration and type, and the bioreactor modules can both be used in parallel, effecting unlimited capacity at a given stage, and also can be scaled up in size.

Methods of Administration

Therapeutic methods of administration and uses for CD133+ cells are known to one of skill in the art and may be found, for example, in U.S. Pat. No. 7,470,538, US Published Application No. US-2004-0258670, and PCT No. WO 2008/085229, all of which are incorporated by reference herein. In the methods described herein, the therapeutically effective amount of expanded CD133+ cells can range from the maximum number of cells that is safely received by the subject to the minimum number of cells necessary for either induction of new blood vessel formation in the ischemic tissue or for increasing blood flow to the ischemic tissue or for relieving blood loss. Generally, the therapeutically effective amount of CD133+ cells is at least $1 \times 10^4$ per kg of body weight of the subject and, most generally, need be no more than $7 \times 10^5$ of each type of cell per kg. CD133+ cells may be administered with hMSCs or other cells. The ratio of CD133+ cells and hMSCs can vary from about 5:1 to about 1:5. A ratio of about 1:1 is preferable. Although it is preferable that the hMSCs are autologous or HLA-compatible with the subject, the hMSCs can be isolated from other individuals or species or from genetically-engineered inbred donor strains, or from in vitro cell cultures.

The therapeutically effective amount of differentiated cells will vary by cell type and amount of loss suffered by those in need of administration. For example, enough RBCs should be administered to relieve the amount of blood loss in a patient suffering from an ailment resulting in lost blood. The administration of blood cells are known to those of skill in the art.

The therapeutically effective amount of the cells of the disclosure can be suspended in a pharmaceutically acceptable carrier or excipient. Such a carrier includes but is not limited to basal culture medium plus 1% serum albumin, saline, buffered saline, dextrose, water, and combinations thereof. The formulation should suit the mode of administration. Accordingly, the invention provides a use of cells of the disclosure, such as CD133+ cells, for the manufacture of a medicament to treat a subject in need thereof. In some embodiments, the medicament further comprises recombinant polypeptides, such as growth factors, chemokines or cytokines. In further embodiments, the medicaments comprise hMSCs or other cells. The cells used to manufacture the medicaments may be isolated, expanded, derived, or enriched using any of the variations provided for the methods described herein.

In a preferred embodiment, the cell preparation or composition of the disclosure is formulated in accordance with routine procedures as a pharmaceutical composition adapted for intravenous administration to human beings. Typically, compositions for intravenous, intra-arterial or intracardiac administration are solutions in sterile isotonic aqueous buffer. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. When the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

A variety of means for administering cells to subjects will, in view of this specification, be apparent to those of skill in the art. Such methods include injection of the cells into a target site in a subject. Cells may be inserted into a delivery device which facilitates introduction by injection or implantation into the subjects. Such delivery devices may include tubes, e.g., catheters, for injecting cells and fluids into the body of a recipient subject. In a preferred embodiment, the tubes additionally have a needle, e.g., a syringe, through which the cells of the invention can be introduced into the subject at a desired location. In a preferred embodiment, cells are formulated for administration into a blood vessel via a catheter (where the term "catheter" is intended to include any of the various tube-like systems for delivery of substances to a blood vessel). The cells may be prepared for delivery in a variety of different forms. For example, the cells may be suspended in a solution or gel. Cells may be mixed with a pharmaceutically acceptable carrier or diluent in which the cells of the invention remain viable. Pharmaceutically acceptable carriers and diluents include saline, aqueous buffer solutions, solvents and/or dispersion media. The use of such carriers and diluents is well known in the art. The solution is preferably sterile and fluid, and will often be isotonic. Preferably, the solution is stable under the conditions of manufacture and storage and preserved against the contaminating action of microorganisms such as bacteria and fungi through the use of, for example, parabens, chlorobutanol, phenol, ascorbic acid, thimerosal, and the like.

Modes of administration of the cells of the disclosure include but are not limited to systemic intracardiac, intracoronary, intravenous or intra-arterial injection and injection directly into the tissue at the intended site of activity. The preparation can be administered by any convenient route, for example by infusion or bolus injection and can be administered together with other biologically active agents. Administration may be systemic. The site of administration may be close to or nearest the intended site of activity. In cases when a subject suffers from global ischemia, a systemic administration, such as intravenous administration, is preferred. Without intending to be bound by mechanism, endothelial generating cells such as CD133+ cells and the hMSCs will, when administered, migrate or home to the ischemic tissue in response to chemotactic factors produced due to the injury.

In one embodiment, the expanded CD133+ cells are co-administered simultaneously with the hMSCs. In another embodiment the hMSCs are administered before or after the injection of the endothelial generating cells. Administration of the mesenchymal stem cells/stromal cells may be carried out using the same mode or different modes of administration. For example, CD133+ cells can be administered by intracoronary injection, while stromal cells might be administered intravenously.

Ischemic tissue that can be treated by the methods of the invention include, but are not limited to, limb ischemia, myocardial ischemia (especially chronic myocardial ischemia), ischemic cardiomyopathy, cerebrovascular ischemia, renal ischemia, pulmonary ischemia, intestinal ischemia, and the like.

In one embodiment of the methods described herein, a recombinant polypeptide or a drug is administered to the subject in combination with the administration of cells. The polypeptide or drug may be administered to the subject before, concurrently, or after the administration of the cells. In one preferred embodiment, the recombinant polypeptide or drug promotes angiogenesis, vasculogenesis, or both. In another embodiment, the recombinant polypeptide or drug promotes the proliferation or differentiation of the CD133+ cells, of the mesenchymal stem cells, or of both. In one embodiment, the recombinant polypeptide is VEGF, BFGF, SDF, CXCR-4 or CXCR-5, or a fragment thereof which retains a therapeutic activity to the ischemic tissue.

In certain embodiments, the invention methods are useful for therapeutic vasculogenesis. Administration of cells of the disclosure according to invention methods can be used as a sole treatment or as an adjunct to surgical and/or medical treatment modalities. For example, the methods described herein for treatment of myocardial ischemia can be used in conjunction with coronary artery bypass grafting or percutaneous coronary interventions. The methods described herein are particularly useful for subjects that have incomplete revascularization of the ischemic area after surgical treatments and, therefore, have areas of ischemic but viable myocardium. Subjects that can significantly benefit from the therapeutic vasculogenesis according to the methods of the invention are those who have large areas of viable myocardium jeopardized by the impaired perfusion supplied by vessels that are poor targets for revascularization techniques. Other subjects that can benefit from the therapeutic vasculogenesis methods are those having vessels of small caliber, severe diffuse atherosclerotic disease, and prior revascularization, in particular bypass grafting. Therefore, the therapeutic vasculogenesis according to the methods of the invention can particularly benefit subjects with chronic myocardial ischemia.

In certain embodiments, the cells of the disclosure are infused into a coronary artery, preferably a coronary artery supplying the area of myocardial ischemia. Where the subject has a totally occluded vessel that would normally supply the area of the ischemic myocardium, the selected coronary artery for infusion is preferably an epicardial vessel that provides collateral flow to the ischemic myocardium in the distribution of the totally occluded vessel.

The therapeutically effective amount of the cells of the disclosure is a maximum number of cells that is safely received by the subject. In certain embodiments, the injection route is intracoronary, and hMSCs in culture become larger than those originally isolated, the maximum dose should take into consideration the size of the vessels into which the cells are infused, so that the vessels do not become congested or plugged. The minimum number of cells necessary for induction of new blood vessel formation in the ischemic myocardium can be determined empirically, without undue experimentation, by dose escalation studies. For example, such a dose escalation could begin with approximately $10^4$/kg body weight of CD133+ cells alone, or in combination with approximately $10^4$/kg hMSCs. Effective amounts of cells of the disclosure sufficient to cause the desired neovascularization can be done based on animal data using routine computational methods. In one embodiment the effective amount is about $1.5 \times 10^5$ CD133+ cells per kg body mass to about $3 \times 10^5$ per kg body mass. In another embodiment the effective amount is about $3 \times 10^5$ per kg body mass to about $4.5 \times 10^5$ CD133+ cells per kg body mass. In another embodiment the effective amount is about $4.5 \times 10^5$ per kg body mass to about $5.5 \times 10^5$ CD133+ cells per kg body mass. In another embodiment the effective amount is about $5.5 \times 10^5$ per kg body mass to about $7 \times 10^5$ CD133+ cells per kg body mass. In another embodiment the effective amount is about $7 \times 10^5$ per kg body mass to about 1×10⁶ CD133+ cells per kg body mass. In another embodiment the effective amount is about 1×10⁶ per kg body mass to about 1.5×10⁶ CD133+ cells per kg body mass. In one embodiment the effective amount of human CD133+ cells is between about 1.5×10⁶ and 4.5×10⁶ CD133+ cells per kg of the subject's body mass and In a preferred embodiment the effective amount is about 5×10⁵ CD133+ cells per kg of the subject's body mass.

In some embodiments of the methods described herein, the composition comprising the CD133+ cells is introduced into a vessel of the subject without substantially altering the arterial pressure. In other embodiments, the composition is introduced into a vessel by blocking arterial flow for an amount of time, such as from 5 seconds to two minutes, such that the injected cells can pool and adhere to the vessel. In one embodiment, a balloon catheter is used to allow pressure driven administration.

One aspect of the invention further provides a pharmaceutical formulation, comprising: (a) CD133+ cells enriched from umbilical cord blood and expanded; (b) optionally mesenchymal stem cells containing surface antigens identified by monoclonal antibodies SH2, SH3 or SH4 enriched from bone marrow; and (c) a pharmaceutically acceptable carrier. In some embodiments, the formulation comprises from $10^4$ to $10^9$ CD133+ cells. In another embodiment, the composition comprises from $10^4$ to $10^9$ mesenchymal stem cells. In a further embodiment, the formulation is prepared for administration by a catheter. In certain embodiments, the CD133+ cells are CD133+/CD34+.

EXEMPLIFICATION

The invention now being generally described, it will be more readily understood by reference to the following examples, which are included merely for purposes of illustration of certain aspects and embodiments of the present invention, and are not intended to limit the invention, as one skilled in the art would recognize from the teachings hereinabove and the following examples, that other stem cell sources and selection methods, other culture media and culture methods, other dosage and treatment schedules, and other animals and/or humans, all without limitation, can be employed, without departing from the scope of the invention as claimed.

Example 1

Using biofunctional nanofiber scaffold that can at least partially mimic the bone marrow (BM) stem cell niche for efficient expansion of human umbilical cord blood (UCB) derived hemangioblasts, we transfected expanded (~225 fold) stem cell population with pro-angiogenic growth factors, and evaluated the neovascularization potential. Flow cytometric analysis revealed that expanded cells retained their progenitor stem cell characteristics. These expanded cells express higher levels of CXCR4 and LFA-1 molecules, are directly linked to cellular homing and adhesion as compared to freshly selected UCB selected cells. Functional analysis revealed that these cells can uptake efficiently AcLDL, migrate in a transwell membrane plate, and can differentiate into endothelial or smooth muscle phenotype. To evaluate neovascularization potential in vivo, hind limb ischemic model was generated and tested with modified stem cell therapy. Expanded cells transfected with angiogenic factors efficiently augmented blood flow and neovascularization than that of expanded cells or freshly isolated cells or media only treated animals. These expanded stem cells are expected to become a major adjuvant for cell-based therapy.

To expand human hematopoietic stem/progenitor cells (HSCs) using functional nanofiber scaffold and genetically modify the stem cells to increase neovascularization potential to treat myocardial ischemia and other peripheral vascular diseases, we have isolated umbilical cord blood (UCB) derived CD133+ (AC133+) cells. We used biofunctional nanofiber scaffold that can at least partially mimic the bone marrow (BM) stem cell niche for efficient cell expansion. Transfection of expanded stem cell population with proangiogenic growth factors was performed and evaluated the neovascularization potential of the cells both in vitro and in vivo hind limb ischemic mouse model.

Materials and Methods

CD133+ Cell Isolation

Fresh human cord blood was obtained from Case Western Reserve University Hospital after IRB approval and written consent from the donor. Cord blood was processed following the similar protocol published earlier (Das H Immunity and Blood). The heparinized cord blood was diluted with PBS and carefully layered over 10 ml of Ficoll. After 30 min centrifugation in a swinging bucket rotor at 14000 rpm, the upper layer was aspirated and the mononuclear cell layer was collected. Following labeling with magnetic bead conjugated anti-CD133 (CD133) monoclonal antibody (Miltenyi Biotech GmbH, Bergisch Gladbach, Germany); two cell separation cycles were run using the AUTO-MACS cell sorter (Miltenyi Biotec) according to the manufacturer's protocol and reagents. After the separation, the purity of the cell product was determined by flow cytometry.

Electro Spinning of PES Nanofiber Mesh

All chemicals were purchased from Sigma-Aldrich (USA) unless otherwise stated. PES granules (Mw: 55,000) was purchased from Goodfellow Cambridge Limited (UK). PES pellets were dissolved in DMSO at 20% wt concentration and placed in a plastic syringe fitted with a 27G needle. A syringe pump (KD Scientific, USA) was used to feed the polymer solution into the needle tip. The feed rate of the syringe pump was fixed at 0.3 mL/h. The PES nanofiber meshes were fabricated by electro spinning at 13 kV using a high voltage power supply (Gamma High Voltage Research, USA). Nanofibers were collected directly onto grounded 15 mm diameter glass cover slips (Paul Marienfeld, Germany) located at a fixed distance of 160 mm from the needle tip, over a collection time of 25 min. PES films were fabricated by dip-coating glass in 10 wt % PES in DMSO. The deposited nanofiber and film samples were washed thoroughly in distilled water and then in ethanol to remove any residue DMSO, and subsequently dried and stored in a desiccators.

Surface Grafting of PES Nanofiber Mesh with Poly (Acrylic Acid) (PAAc)

Acrylic acid (AAc) (Merck, Germany) was distilled and stored at −20° C. prior to use. PAAc was grafted onto the PES nanofiber mesh surface by photo-polymerization, as described previously with slight modification on the grafting conditions [18]. Briefly, samples were immersed in aqueous solution containing 3% AAc solution and 0.5 mm NaIO4 in a flat-bottom glass container. The temperature of the solution was maintained at 8° C. by cooling the container in a cold-water bath. The samples were then exposed to UV from a 400 W mercury lamp (5000-EC, Dymax, Germany) for 2 min at a distance of 25 cm. The PAAc-grafted meshes were then thoroughly washed with deionised water at 37° C. for over 36 h to remove any ungrafted PAAc from the surface of the scaffold and dried in storage desiccators.

Amination of PAAc-Grafted PES Nanofiber Mesh and Films

The PAAc-grafted PES nanofiber mesh and films were further conjugated with ethylene diamine (EtDA) using a 2-step carbodiimide cross-linking method. Briefly, each scaffold was first gently shaken in 2 mL acetonitrile containing 50 mm N-hydroxysuccinimide (NHS) and 50 mm dicyclohexylcarbodiimide (DCC). After 6 h, the reaction solution was carefully aspirated and each scaffold was immediately immersed into 2 mL acetonitrile containing 0.03 mmol EtDA. After 12 h, the reaction solution was carefully aspirated and each scaffold was thoroughly washed in absolute ethanol to remove any dicyclohexyl urea (DCU), which is a by-product of the conjugation reaction. As a control, several PAAc-grafted PES nanofiber meshes were hydroxylated instead, by conjugation with ethanolamine using the same modification protocol as described above. All substrates were subsequently sterilized in 70% ethanol, then loaded into 24-well tissue culture plates (Nunc) and stored in sterile PBS until use.

Surface Analysis of Modified PES Nanofiber Mesh and Films

Surface amine density was quantified according to the method described by Kakabakos et al. [23]. Briefly, primary amino groups on the substrates were first converted to sulfhydryl groups through reaction with excess 2-iminothiolane (Pierce, USA). The surface sulfhydryl groups were then determined using a BCA assay kit (Pierce) using 1-cysteine to generate a standard curve. Surface wettability of the various substrates was characterized by measuring the water contact angle at room temperature using a video contact angle goniometer (Advanced Surface Technology, USA). Samples of unmodified and aminated PES nanofiber meshes were also imaged using a field emission scanning electron microscope (FESEM, FEI Company, USA) for detection of any morphology changes caused by the entire amination process. Fiber diameters were measured by analyzing representative scanning electron microscopy (SEM) mages of nanofibers using NIH ImageJ software (rsb.info.nih.gov/ij/). At least 250 measurements were recorded for each analysis.

Ex-Vivo Hematopietic Expansion Cultures

Human umbilical cord blood CD133+ sorted cells were isolated from fresh cord obtained from CWRU Hospital as mentioned earlier. Purified recombinant human stem cell factor (SCF), Flt-3 ligand (Flt3), TPO and IL-3 were purchased from Peprotech Inc. (Rocky Hill, N.J., USA). The StemSpan SFEM medium was purchased from StemCell Technologies (Vancouver, BC, Canada). Different substrates were secured at the bottoms of wells of a 24-well aminated tissue culture plate. Eight hundred CD133+ cells were seeded onto each scaffold in 0.6 mL StemSpan™ serum-free expansion medium, which consists of 1% BSA, 0.01 mg/mL recombinant human insulin, 0.2 mg/mL human transferrin, 0.1 mm 2-mercaptoethanol and 2 mm 1-glutamine in Iscove's MDM, supplemented with 0.04 mg/mL low-density lipoprotein (Athens Research and Technology Inc., USA), 100 ng/mL SCF, 100 ng/mL Flt3, 50 ng/mL TPO and 20 ng/mL IL-3. Cells were cultured at 37° C. in an atmosphere containing 5% $CO_2$ for 10 days without medium change. Similar cultures were also performed on tissue culture polystyrene surface (TCPS), which serve as a positive control in this study. Cells were harvested after 10 days of expansion. All substrates were washed once with non-trypsin cell dissociation solution and twice with 2% FBS Hanks' buffer at 5-10 min intervals between each wash. The cell suspensions collected were then concentrated through centrifugation at 500 g for 10 min. Aliquots of the concentrated cells were then used for cell counting by a hematocytometer, flow cytometry analysis, as well as for further studies.

Flow Cytometry

For flow cytometric analysis cell surface markers were blocked with FCR Blocking Reagent (1:5; Miltenyi Biotec) and incubated for 20 min at 4° C. with the following antibodies: anti-CD34-PE, and anti-CD133/2 FITC (all from Miltenyi Biotec). CD117 labeling was performed using anti-CD117 antibody (clone YB5.B8; 1:100; BD Parmingen, BD Bioscience, San Diego, Calif., USA). Isotype controls were purchased from BD Pharmingen. After incubation cells were washed with MACS sorting buffer and analyzed using a FACS Calibur flow cytometer (Becton Dickinson, Heidelberg, Germany). Dead cells were excluded via propidium iodide staining. Data analysis was performed with BD CELLQuest software Fluorescently labeled antibodies for CD34 and other cell surface markers (CD13, CD15, CD19, CD38, CD45 and GlyA) were purchased from BD Biosciences (USA). Fluorescently labeled antibodies for CD41 were purchased from Dako (USA). The cell samples were incubated at 4° C. for >30 min in 2% FBS Hanks' buffer in the presence of various antibody combinations. After antibody staining, the cells were washed twice using Hanks' buffer and fixed in 1% paraformaldehyde. Cells were analyzed by triple-color flow cytometry on a FACSCalibur analyzer (BD Biosciences). Relevant isotype controls were also included to confirm specificity and for compensation setting. At least 20,000 events were acquired. The Milan-Mulhouse gating method was used for cell enumeration [24], where a double gating (CD34+CD45+) strategy was used to identify the primitive hematopoietic progenitor cell population in the ex vivo expansion cultures. The CD34 marker is generally expressed by primitive hematopoietic progenitor cells, while CD45 marker is expressed on all cells of hematopoietic origin with the exception of red blood cells and their immediate precursors.

Genetic Manipulation of Stem Cells

Freshly isolated human CD133+ MACS sorted cells or nano-fiber expanded cells were transfected with either GFP containing vector (pmaxGFP) or VIP vectors (VEGF IRIS and PDGF in pAMFG vector, Generous gift from Dr. Blau, Stanford University, CA) using Amaxa Inc., human CD34 cell nucleofactor kit, following manufacturer's protocol. In brief, $1-3\times10^6$ cells were transfected with 2-4 ug of plasmid DNA in 100 ul of CD34 cell nucleofactor solution and using programs: U-008/U-001. After transfection cells were either cultured with DMEM, EBM-2 or SMBM complete media for further studies.

ELISA

One million cells were transfected with VIP vector or empty vector and collected cell culture supernatant at 24 h or 48 h time point. For quantification of PDGF secretion, ELISA assay was performed by using Quantikine human PDGF-BB ELISA kit from R&D Systems, Minneapolis, Minn., following manufacturer's protocol.

Dil-Ac-LDL Uptake Assay

Dil-Ac-LDL uptake was performed following standard protocol. In brief, after expansion of CD133+ cells on nanofiber for 10 days cells were plated in glass bottom chamber slides for another 10 days with RPMI 1640 complete media with changes of media in every $3^{rd}$ day. Aspirated culture media and washed cells with PBS. Added serum free RPMI 1640 containing 10 ug/ml Dil-Ac-LDL and incubated for 4 h at 37° C. Aspirated media and washed cells twice with PBS to remove free Dil-Ac-LDL. Fixed cells with 3% formalin in PBS for 10 min followed by washing with PBS. Slides were mounted with Vectashield includes DAPI. Visualized under fluorescent microscope and digital photographs were taken.

Generation of Hind Limb Ischemic Mice and Delivery of Cells

All animal experiments were performed in accordance with the guidelines published in the "Guide for the Care and Use of Laboratory Animals" (NIH publication), and under the protocols approved by the Institutional Animal Care and Use Committee at Case Western Reserve University. Male SCID/NOD mice (7 weeks old) were purchased from Jackson laboratory (Barharbor Me.). Mice were anesthetized with an intra-peritoneal injection of sodium pentobarbital, the proximal left femoral artery was ligated at 2 points 3 mm apart, and the artery between the ligatures was excised. Three groups of mice were made, and each group (6-9 mice) was injected with either media alone or $5 \times 10^5$ freshly isolated CD133+ cells or 10-day nano-fiber-expanded cells via intra-ventricular delivery in 300 ul volume. At various time points, such as days 1, 7, 14 and 28, mice were assessed for functional recovery and blood flow. At the end of the study at day 28, mice were sacrificed and both gastrocnemius muscles were excised.

Laser Doppler Perfusion Imaging

Blood flow was measured with a laser Doppler perfusion image analyzer (Moor Instruments Co Ltd, Devon, UK) at various time points (day 1, 7, 14 and 28) mice were assessed for functional recovery and blood flow of the study.

Capillary Staining and Counting

To determine the capillary density in the border zone of the hind limb ischemia, tissue was dissected and formalin fixed. Fixed tissues were paraffin embedded and sections were stained using monoclonal anti-mouse CD31 antibody (Chemicon) and incubated with biotinylated secondary antibody. For quantification of positively stained vessels, 4 sections from within the necrosis border zone of each animal were analyzed by an investigator who was blinded with respect to the cell treatment. Capillaries were counted in 12 randomly chosen high-power fields (HPFs) in 4 sections per tissue and 5 animals per group. The results were expressed as capillaries per high power field.

Scanning Electron Microscopy

Selected cultures samples were gently rinsed with PBS, fixed with 3% glutaraldehyde for 30 min at 20° C., and post-fixed with 1% osmium tetraoxide for another 15 min at 20° C. Samples were then dehydrated using a graded series of ethanol (25%, 50%, 70%, 90%, 95%, 100%) followed by HMDS drying. The samples were mounted onto aluminum stubs and gold sputter-coated before viewing under FESEM.

Statistical Analysis

All values are presented as mean±standard deviation of the mean. One-way ANOVA with Scheffe's post hoc test for unequal sample sizes was used to compare numeric data between the four experimental groups. Datasets consisting of two groups only were compared by unpaired Student's t-test. A level of $p<0.05$ was considered as significant difference.

In Vitro Differentiation Assays, Immunostaining and Confocal Microscopy

To assess the angiogenesis-relevant differentiation potential of cord blood-derived CD133 cells, which were expanded on nano-fiber for 10 days, separate series of cell products (n=4, each) were cultivated and induced to adopt an endothelial or smooth muscle phenotype. Ten-day expanded cells were either cultured with EGM2 medium (Cambrex) or SMBM medium for another 14 days to a chamber slide (Labtek, Nunc International Inc) changing media in every $3^{rd}$ days. All cultures were performed in quadruplicate, incubated at 37° C. in 5% $CO_2$ and 95% humidity, and scored after 14 days of culture by light microscopy. Immunostaining for Rhodamin conjugated Phalloidin (Invitrogen), F-actin von Willebrand factor (vWF) was performed (monoclonal anti-vWF antibody followed by FITC-conjugated secondary goat anti-mouse IgG). After several washing steps, samples were viewed by confocal microscopy (Leica). Cultured human umbilical vein endothelial cells (HUVEC) and NIH3T3 cells served as positive and negative controls, respectively.

Immunostaining

For immunohistologic detection of human cells, paraffin embedded tissue sections were incubated with monoclonal mouse anti-human nuclear antigen antibody (MAB 1281; 1:50; Chemicon) or monoclonal mouse anti-HLA-class I antibody W6/32 (Dako M0736). For measurement of capillary density, sections were stained with anti-mouse CD31 antibody (Chemicon). After blocking in Envision blocking buffer (DAKO), sections were placed in primary antibody overnight at 4° C. On the following day, the sections were rinsed and then incubated with secondary antibody (FITC/PE-conjugated secondary goat anti-mouse IgG.).

Example 2

Isolation of Fresh Umbilical Cord Blood Derived Stem Cells and Ex Vivo Expansion In general, via regular processing of human umbilical cord blood samples (60-80 ml sample volume) we are able to isolate $5 \times 10^5$ to $1 \times 10^6$ CD133+ cells using a magnetic bead-conjugated immunopurification system (AutoMACS, Miltenyi Biotec Inc.) Representative flow cytometric analysis revealed that UCB-derived CD133+ cells isolated by this method were above 90% pure (FIG. 1). However, it would be preferable to obtain a larger number of cells than this purification method yields, especially for applications such as ex vivo characterization. Applicants describe herein a way to significantly expand these cells ex vivo without major changes in their phenotype. We demonstrate here our ability to successfully expand an initial population of 20,000 cells to a quantity of at least 4.5 million (225-fold amplification) cells over 10 days of culture using a 24-well nanofiber coated plate. Even at day 5, a 20 to 25-fold expansion was observed.

Example 3

Phenotypic Characteristics of the Expanded Stem Cells

Figure 3:
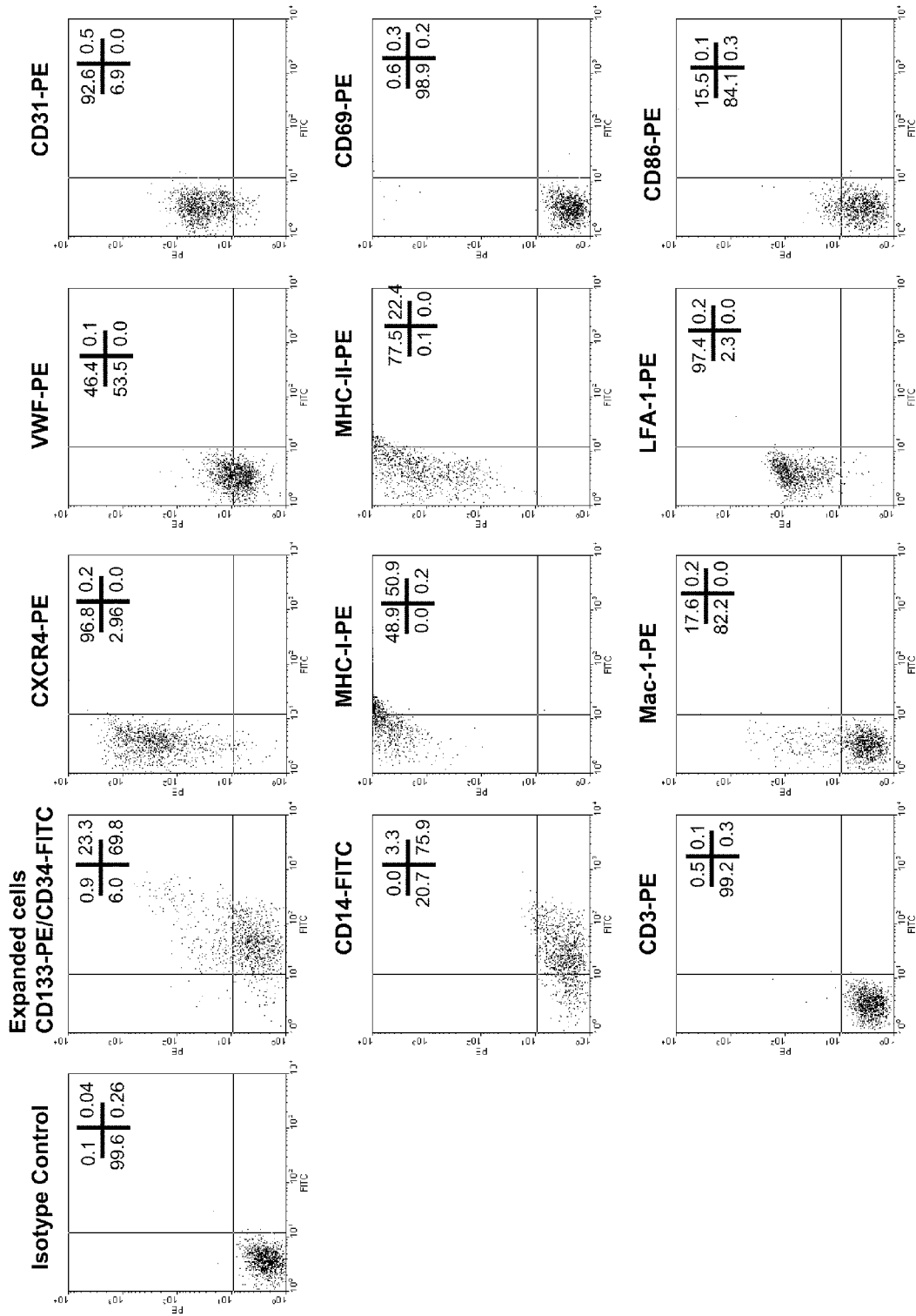
FIG. 3. Characterization of nanofiber scaffold expanded cells. Flowcytometric analysis was performed for the characterization of nanofiber scaffold expanded cells at day 10 using various conjugated antibodies as stated in one or two color staining. This is a representative of the three independent analyses of the expanded cells.
Figure 23:
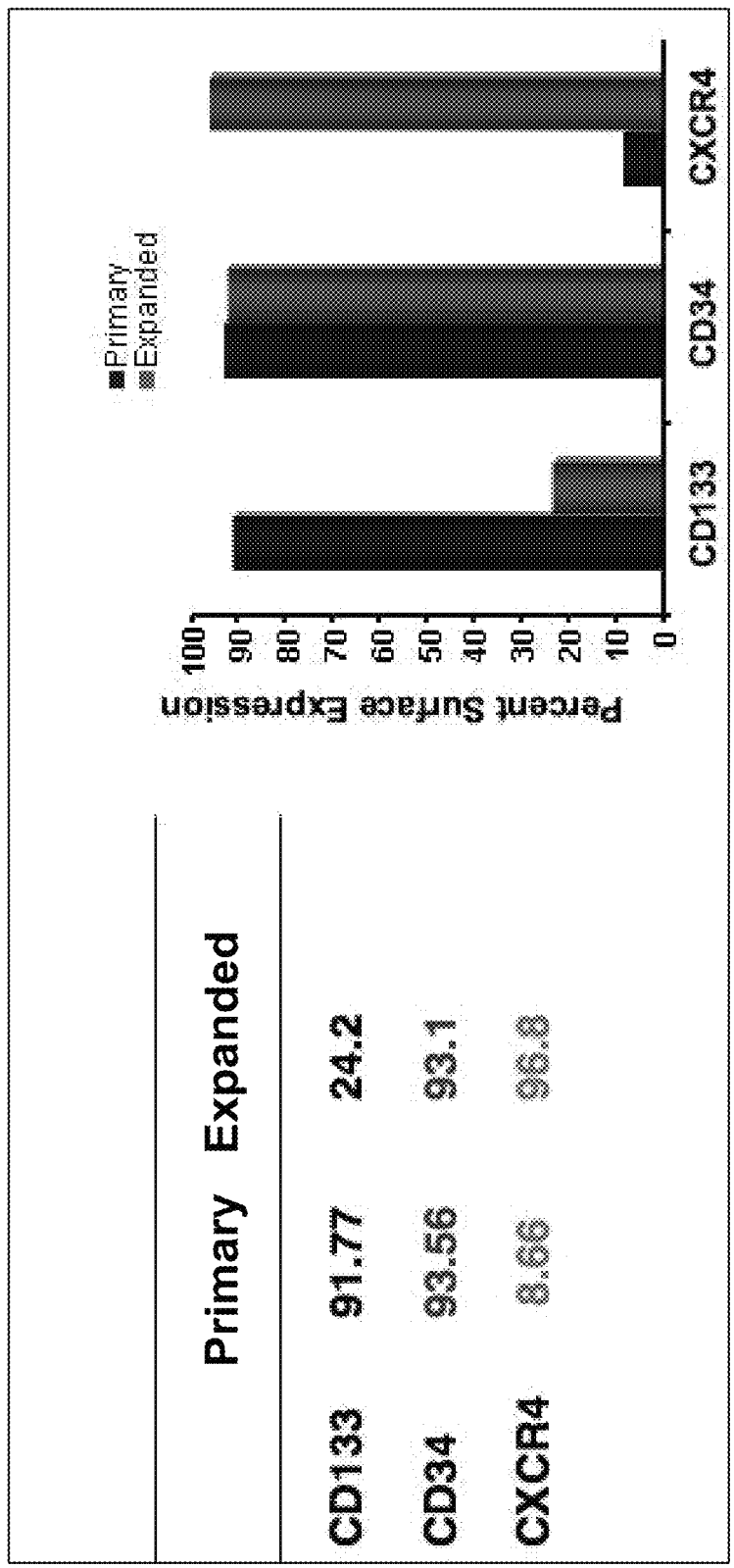
FIG. 23. MACS Sorted CD133 Surface Phenotype in Primary and Expanded Cells. Expression of CD133, CD34 and CXCR4 were compared between primary and expanded cells.
Figure 25:
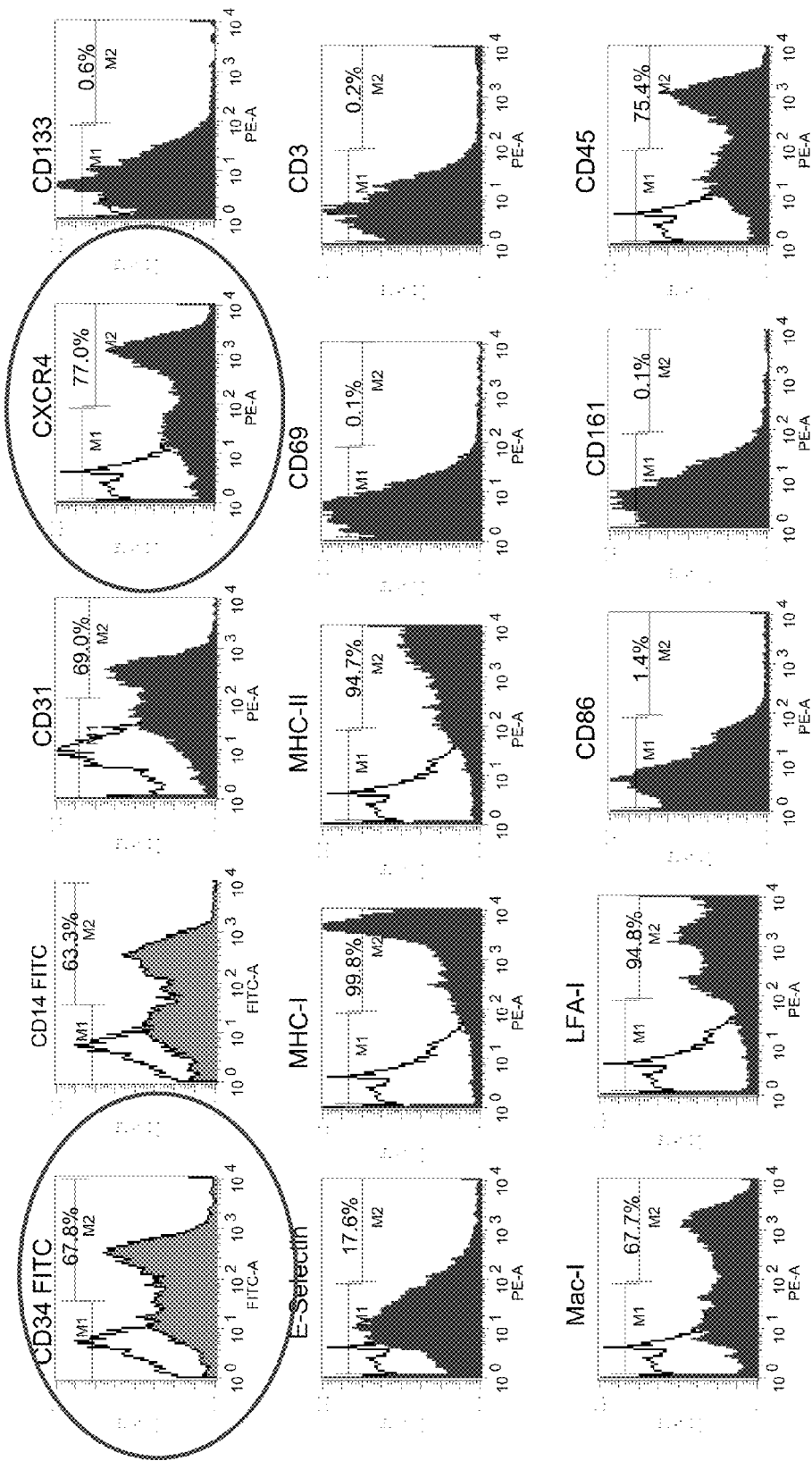
FIG. 25. Phenotype of Expanded Cells. Various markers were analyzed in expanded CD133+ cells.
Figure 26:
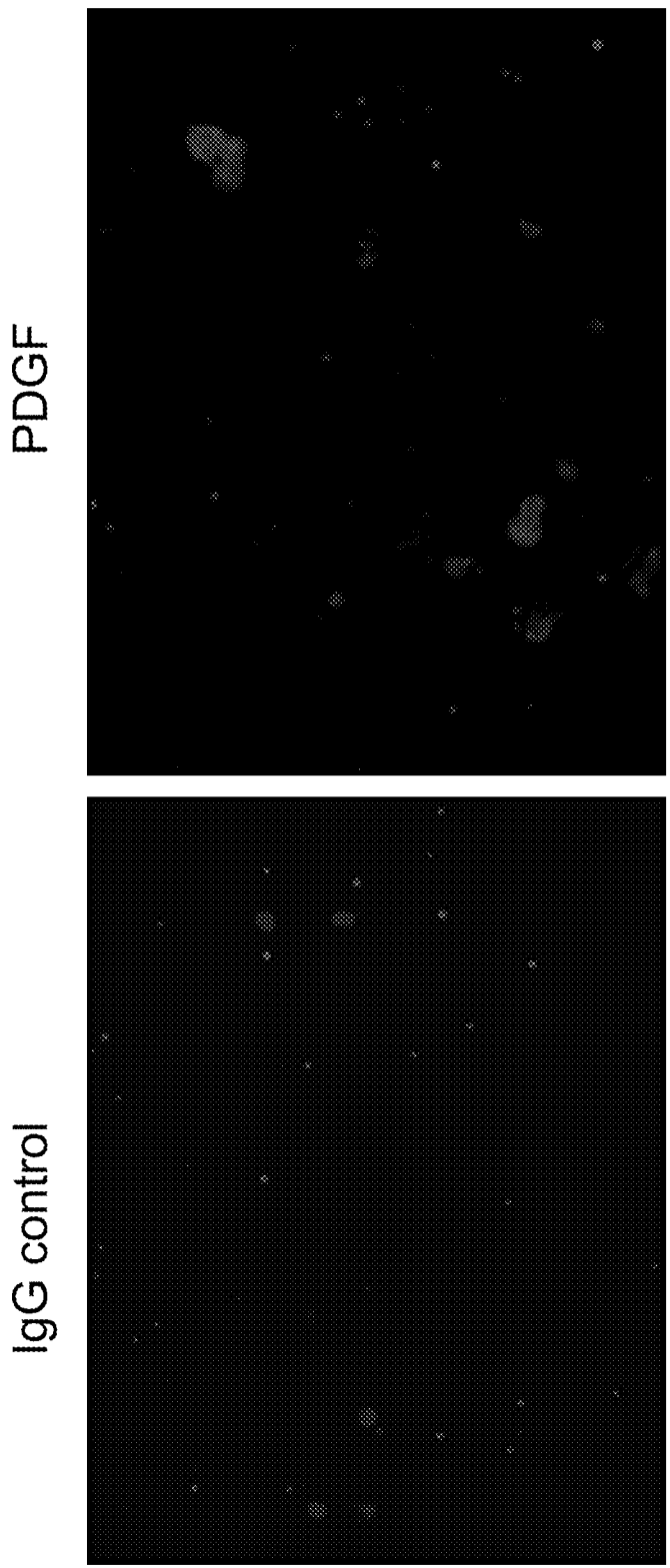
FIG. 26. Transfection of VIP Vector in CD133+ expanded cells. PDGF was detected in VIP transfected cells.

To examine phenotype of these expanded cells, flow cytometric analysis was performed using several relevant antibodies (FIGS. 3, 23 and 25). Almost 24% of the total cells retain their CD133 positivity and 93% of the cells retain their CD34 positivity. A remarkable increase in expression of two important pro-migratory and pro-adhesive molecules (CXCR4 and LFA-1, respectively) was observed in this analysis. Mild to moderate expression of other myeloid markers were observed such as CD14, CD86, vWF, CD31 or Mac-1. These expanded cells do not express any activation markers (CD69) or pan T cell markers (CD3) molecules on their surface, indicating that these expanded cells retain their stem cell characteristics. However, these cells highly express MHC class-I or Class-II molecules on their surface.

Example 4

In Vitro Characterization of the Expanded Stem Cells i) AcLDL Uptake Assays—

Figure 5:
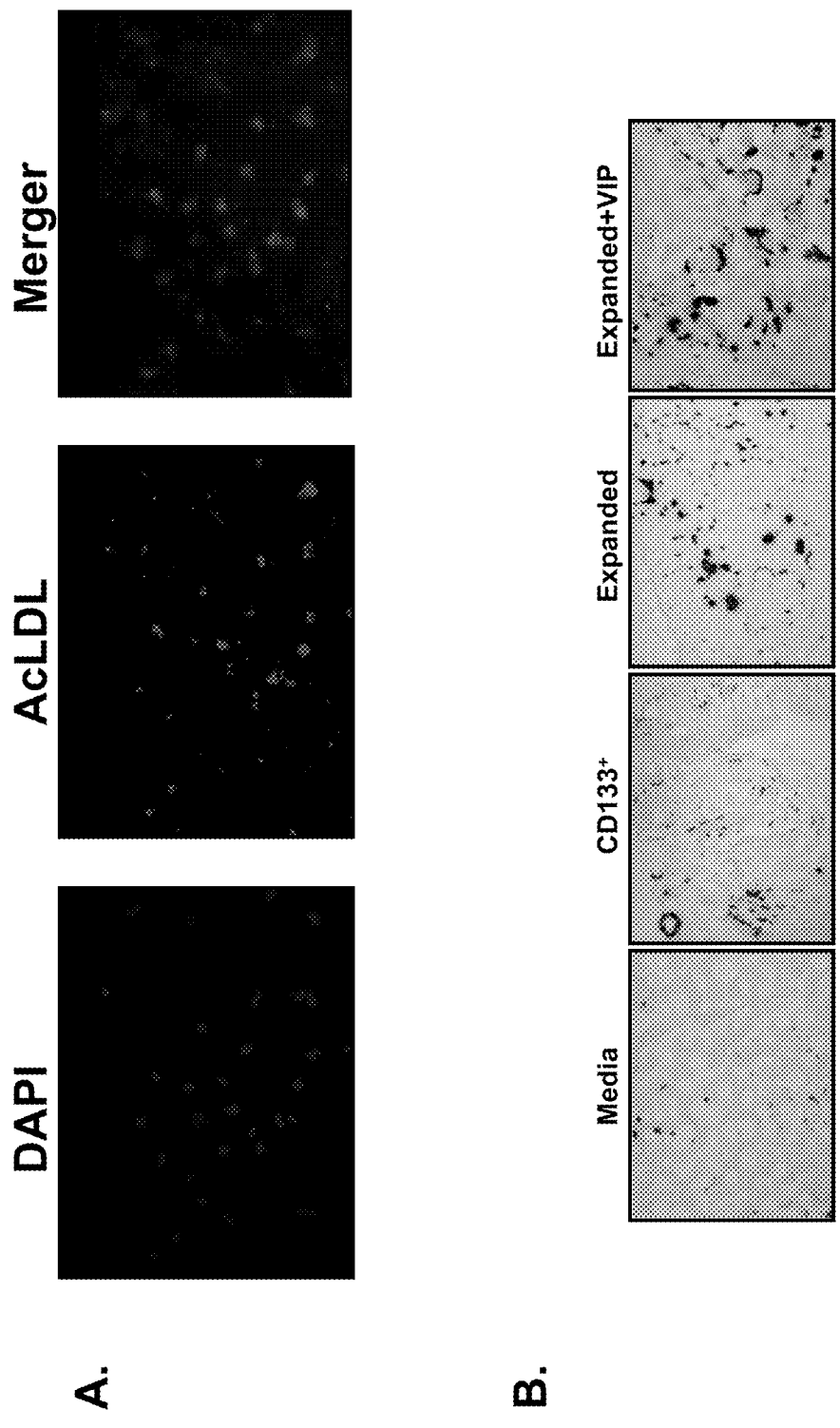
FIG. 5. In vitro functional evaluation of the expanded cells. A. The 10-day nanofiber expanded cells were re-cultured on a chamber slide using regular complete DMEM plus 10% FBS and PSG for 7 days. Dil-AcLDL was added to the culture and incubated for 4 h at 37 C. cells were washed, fixed and mounted with DAPI. Nucleus stained with DAPI (blue) and uptaken Dil-AcLDL (red in color). B. Detection of stem cell migration. Five hundred thousand GFP vector or empty vector transfected nanofiber expanded stem cells were injected into each of the hind limb ischemic mice via intra-myocardial delivery. After 36 h of injection mice were sacrificed and organs were harvested. Immunohistochemical detection was performed with the fixed and paraffin embedded tissue sections using anti-GFP Ab. Appropriate controls were also evaluated.

To verify retention of their basic stem cell characteristics, we have analyzed the potential of these expanded cells to uptake AcLDL (a functional property of differentiated stem cells). These 10-day nanofiber expanded cells were re-cultured on a chamber slide using regular complete DMEM plus 10% FBS and supplements for 7 days. AcLDL uptake assay was performed as described previously (39). Here we demonstrate that all differentiated cells can uptake AcLDL efficiently (FIG. 5A).

ii) Transwell Migration Assays—

Figure 27:
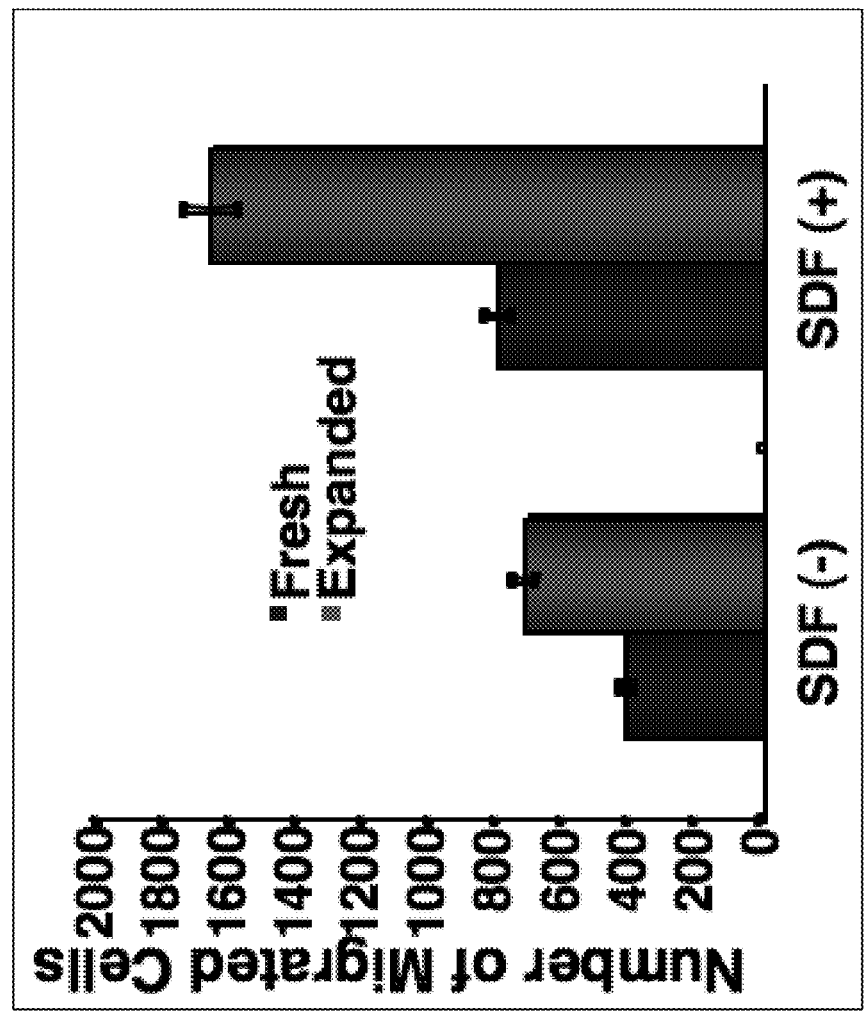
FIG. 27. Transwell migration of stem cells. Migration was compared between fresh and expanded cells with and without SDF.

To assess the potential of the expanded cells to migrate towards a chemo attractant, 30,000 nanofiber-expanded versus freshly isolated CD133+ cells were plated on a transwell to verify migratory capacity in the presence or absence of stromal derived factor-1 (SDF) after four hours of incubation. Migrated cells were stained with Giemsa and counted under a light microscope. A significant (~2-fold) increase in migration was observed for the nanofiber expanded cells compared to the freshly isolated cells in the presence or absence of SDF-1 (FIG. 27). Thirty thousands either freshly isolated CD133+ cells or nanofiber expanded cells were plated on the transwell and assessed migratory capacity in the presence or absence of stromal derived factor (SDF) after four hours of incubation. Migrated cells were stained with Giemsa and counted under microscope. A statistically ($P<0.001$) significant (almost two-fold) increase in migration was observed for the nanofiber expanded cells compare to the freshly isolated cells in the presence or absence of SDF.

Five hundred thousand GFP vector or empty vector transfected nanofiber expanded stem cells were injected into each of the hind limb ischemic mice via intra-myocardial delivery. After 36 h of injection mice were sacrificed and organs were harvested. Immunohistochemical detection was performed with the fixed and paraffin embedded tissue sections using anti-GFP Ab. Appropriate controls were also evaluated.

Example 5

In Vitro Differentiation of the Expanded Stem Cells

Figure 6:
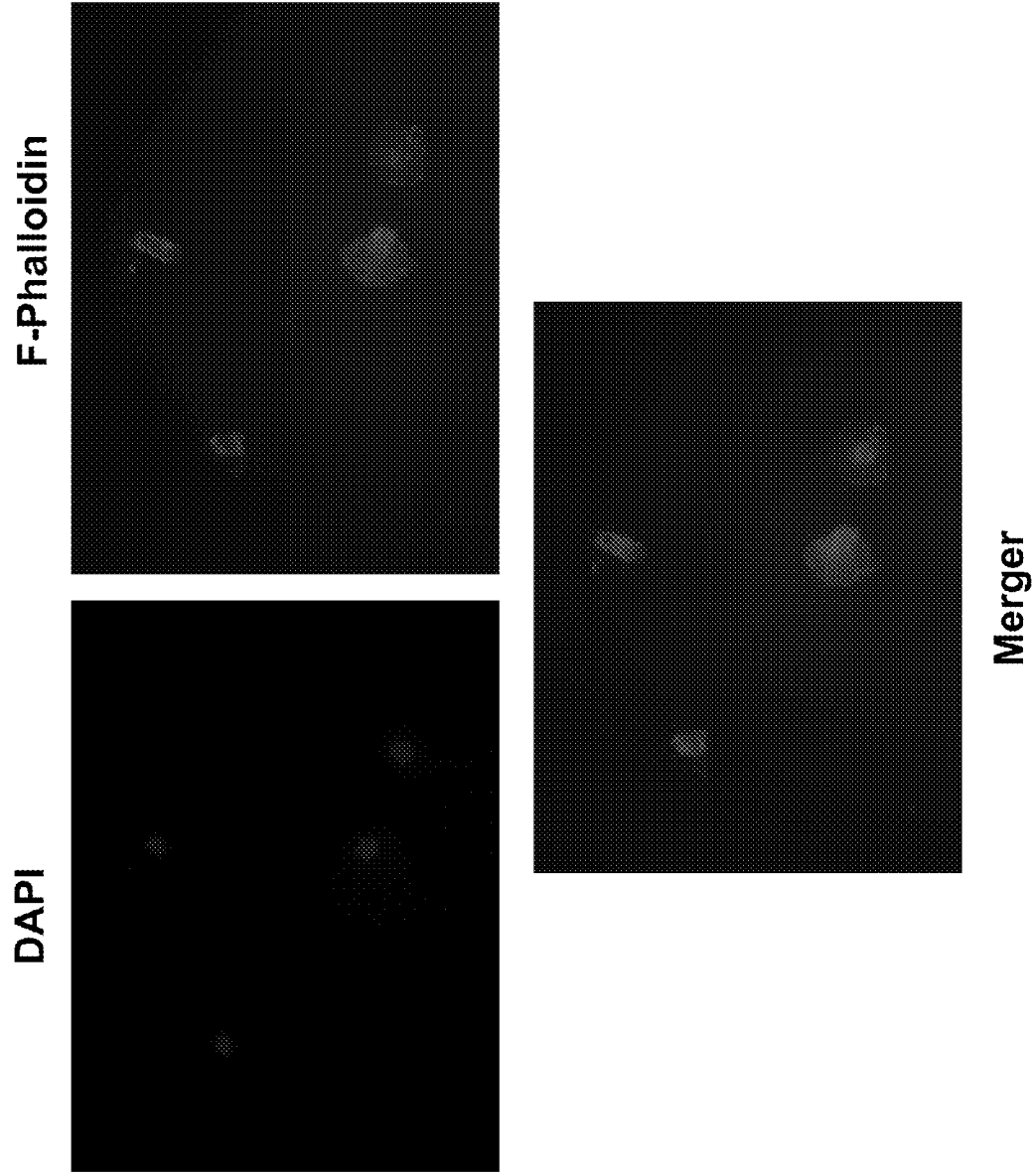
FIGS. 6, 7, and 8. In vitro differentiation of expanded stem cells to smooth muscle cells. Expanded cells were also cultured with SMBM complete media for another 14 days. Indeed, early smooth muscle differentiated marker such as F-Phalloidin, smooth muscle myosin heavy chain (SM-MHC) and smooth muscle α-actin staining indicated that they are positive for all markers. Respective isotype controls were evaluated for representative studies.
Figure 7:
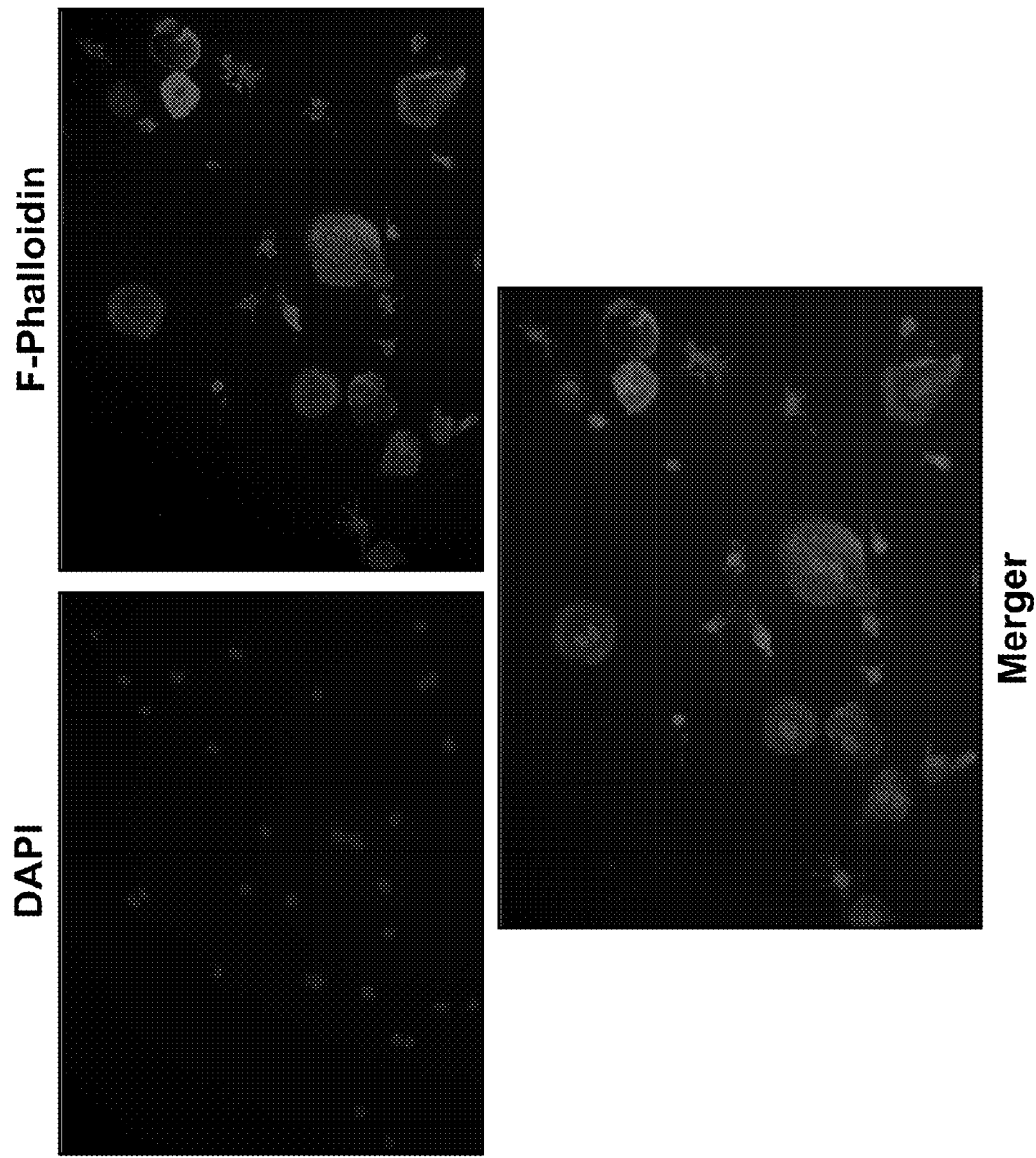
Figure 8:
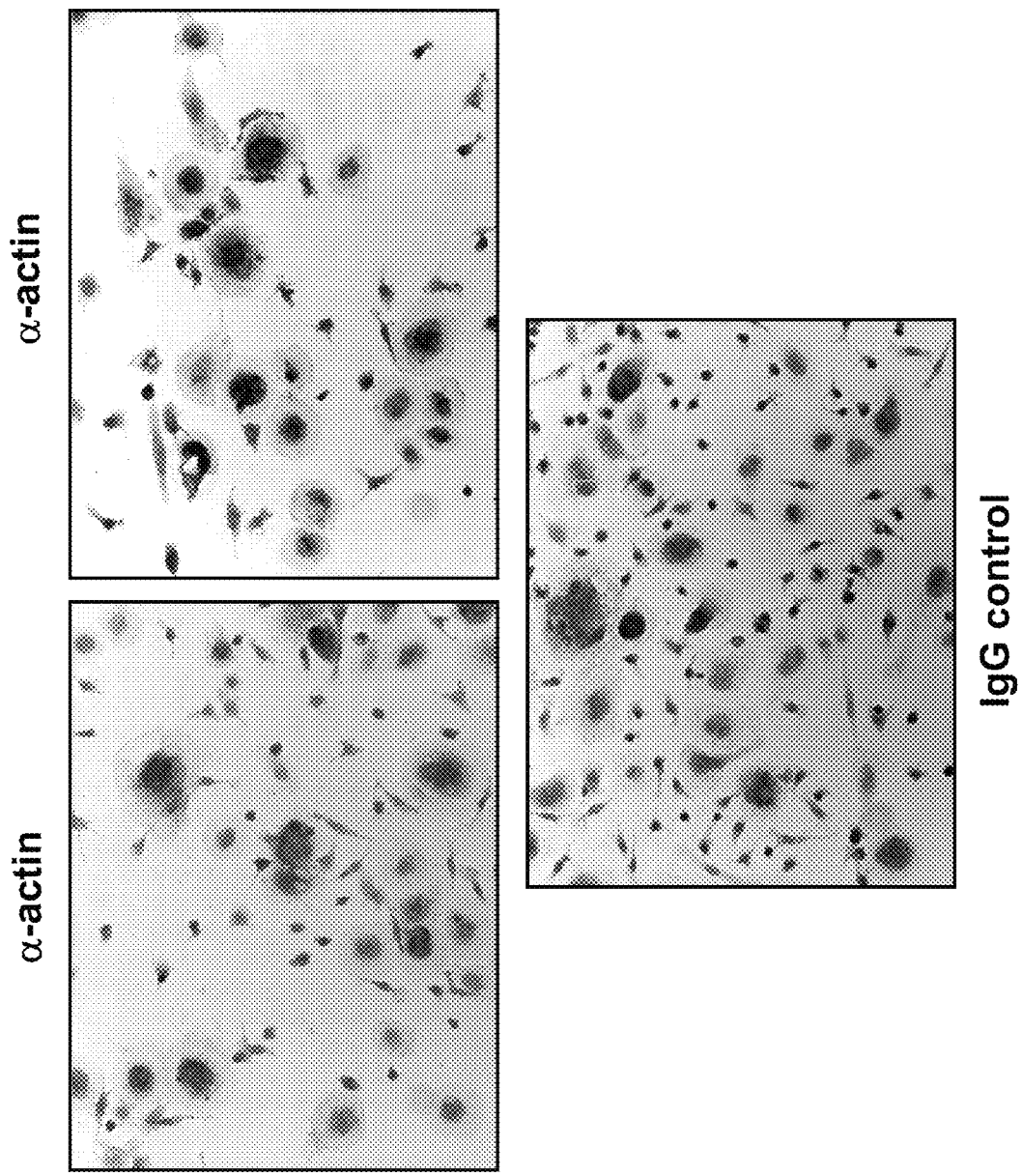
Figure 9:
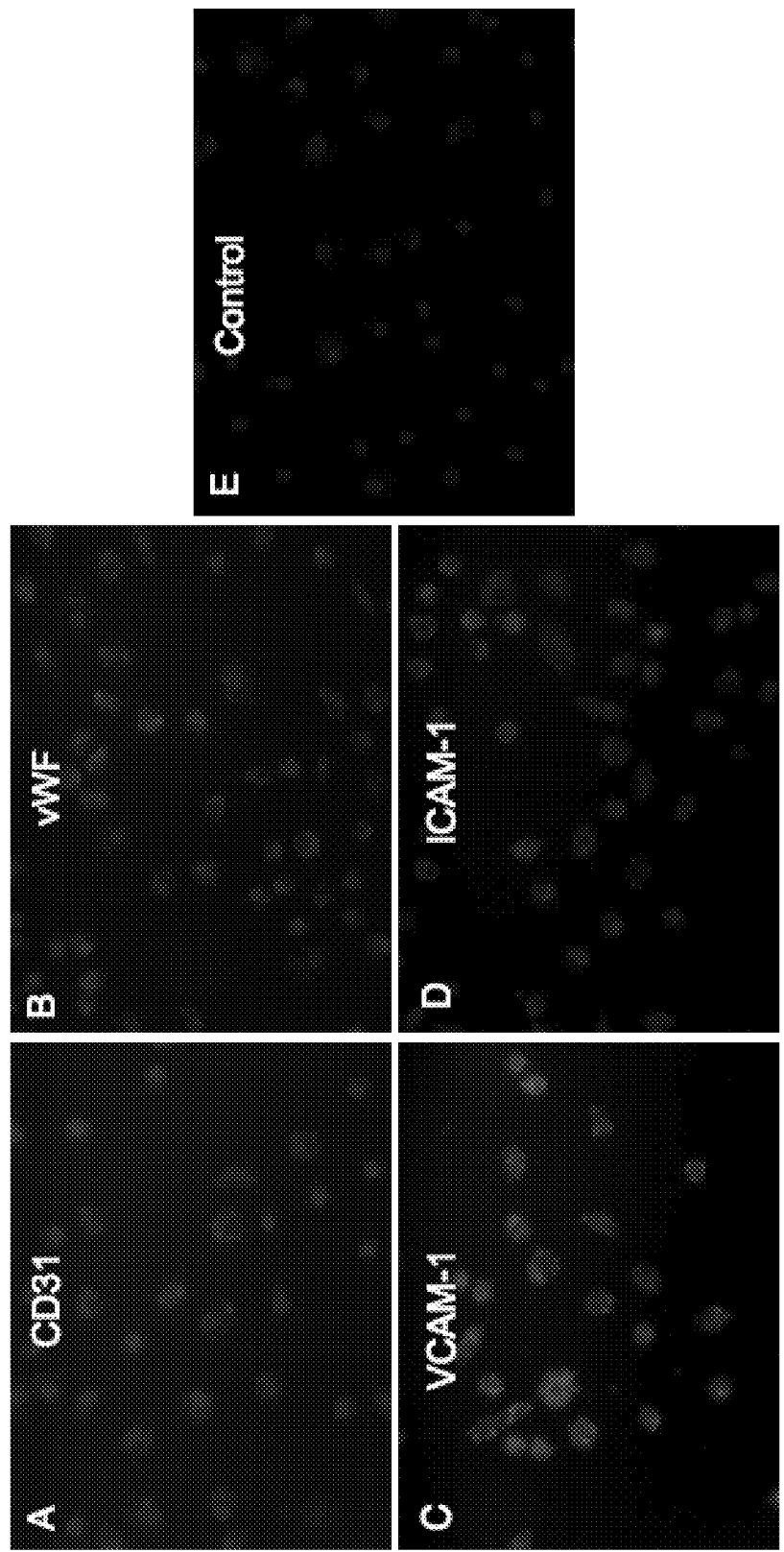
FIG. 9. In vitro differentiation of expanded stem cells to endothelial lineage. The 10-day nanofiber expanded cells were re-cultured for another 14 days on chamber slides with EGM2 media. Immunofluorescence studies were performed using endothelial specific markers to the differentiated cells. Early endothelial markers, such as CD31, vWF and ICAM-1 and VCAM-1 were studied, isotype-matched IgG were also used for control staining. Indeed, these cells were positive for the early endothelial markers. Isotype control was evaluated for the representative experiment.

Progenitor stem cells have capacity for pluripotent differentiation. It is important to verify that our expanded cells retain pluripotency similar to freshly isolated UCB-derived AC133+ cells. In this assay, we assessed the ability of 10-day expanded cells to differentiate to the smooth muscle or endothelial lineage via sub culturing with "differentiation-media" for an additional 14 days on chamber slides. Differentiated cells could be identified by their morphology on light microscopy with readily discernible differences between the endothelial and smooth-muscle lineages. Cells cultured with smooth muscle differentiation media were visibly more spread out on the plate than that of endothelial media cultured cells, which were more elongated in shape. Expressions of endothelial specific markers (CD31, vWF, ICAM-1, VCAM-1) were assessed after additional 14 days incubation in EGM2 media. Indeed, these cells were positive for these early endothelial markers (FIG. 9). Isotype control was evaluated for the respective experiments. Cells were also cultured with SMBM complete media for another 14 days for differentiation towards the smooth muscle lineage. Under these conditions, early smooth muscle differentiated markers such as F-Phalloidin, smooth muscle myosin heavy chain (SM-MHC) and smooth muscle a-actin were positive (FIGS. 6, 7, and 8). Respective isotype controls were evaluated for representative studies. Taken together, these data demonstrate that our ex vivo expanded cells maintain potency to differentiate into endothelial or smooth-muscle lineages under specific culture conditions.

Example 6

Genetic Modification of Expanded Stem Cells

Figure 10:
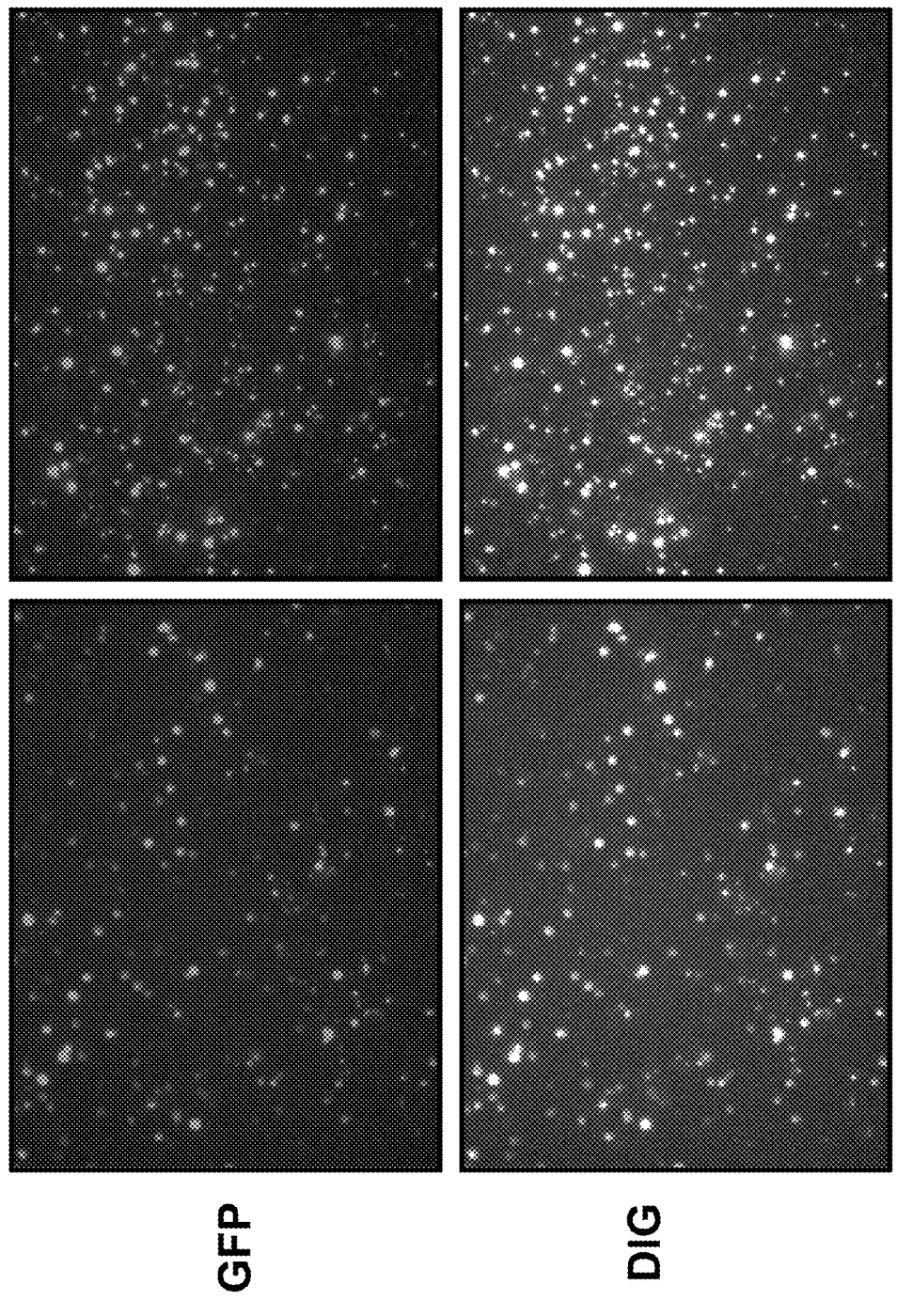
FIGS. 10 and 11. Genetic manipulation of expanded stem cells. Expanded cells were transfected pmaxGFP vector using Nucleofactor technology and human CD34 cell nucleofactor kit (Amaxa Inc. program U-008) following manufacturer's protocol. At 24-h post transfection cells were visualized under fluorescent microscope for green fluorescence protein (GFP) expression and under normal light for cellular morphology. Almost all cells were expressing GFP indicates an efficient transfection. We subsequently cultured these cells with regular complete DMEM media for another 14 days to evaluate cellular differentiation and viability. These cells look elongated in shape and endothelial like appearance (FIG. 11).
Figure 11:
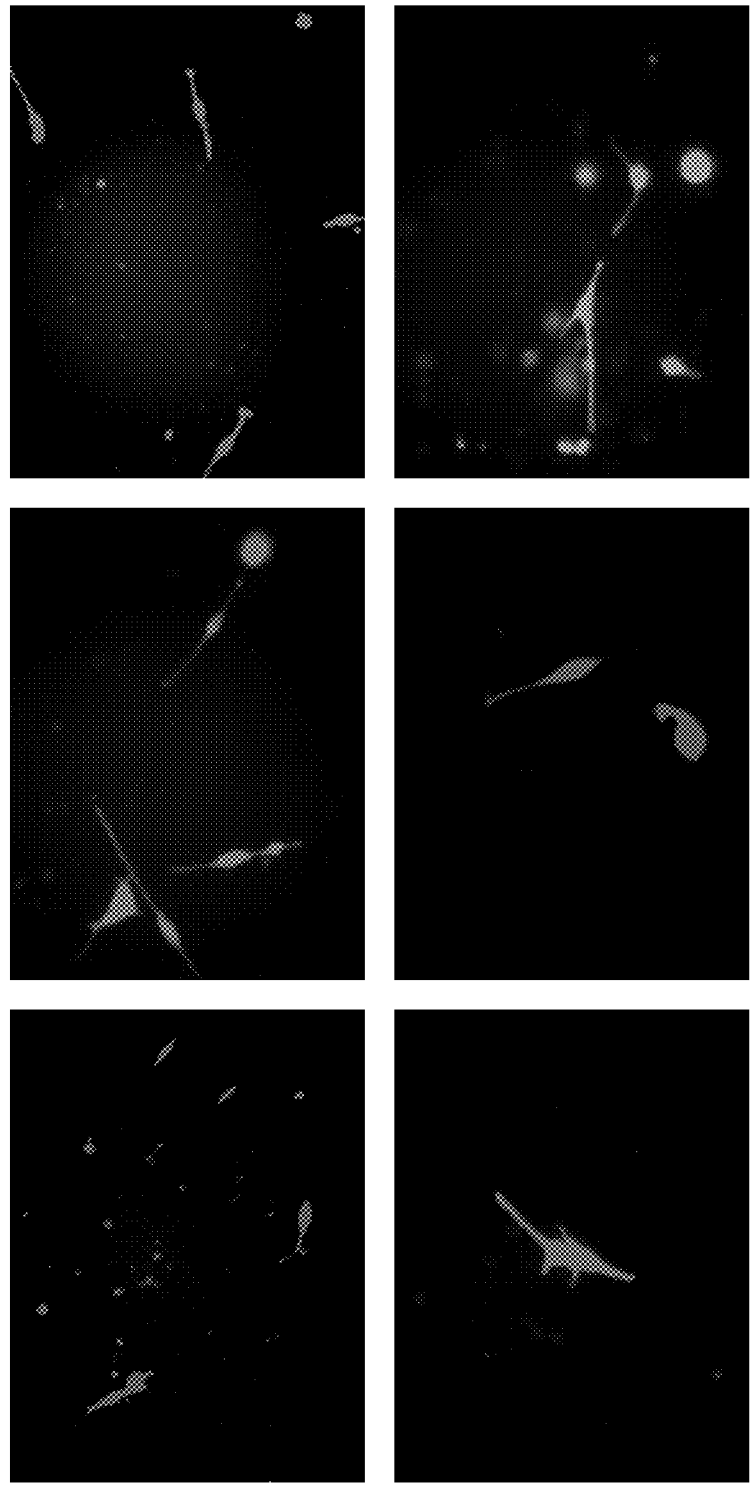
Figure 12:
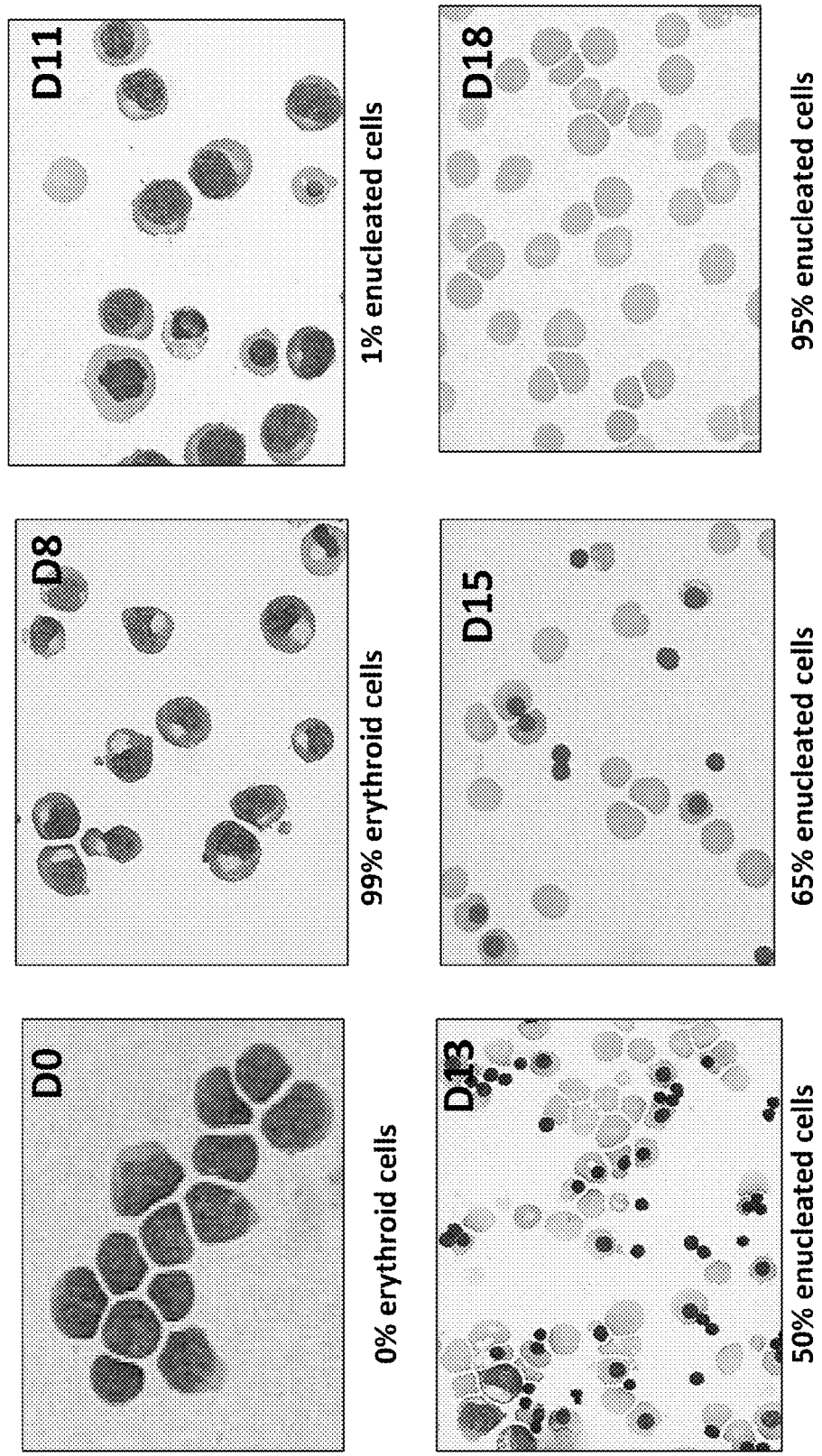
FIG. 12. Erythroid differentiation. Cytology of differentiated cells were examined after 0, 8, 11, 13, 15 and 18 days of culture.
Figure 14:
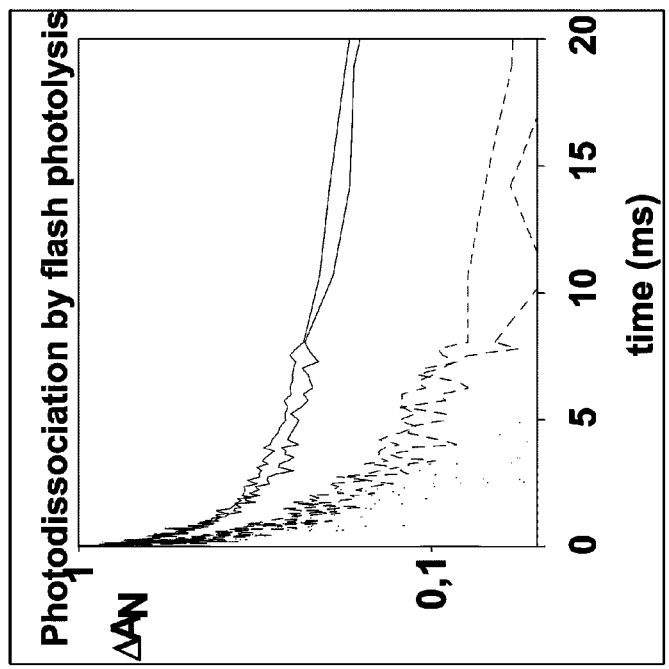
FIG. 14. Functional NANEX RBCs vs. Natural RBC Oxygen Transportation and Release Comparison. Control RBCs and expanded RBCs were compared for photodissociation and oxygen binding.
Figure 15:
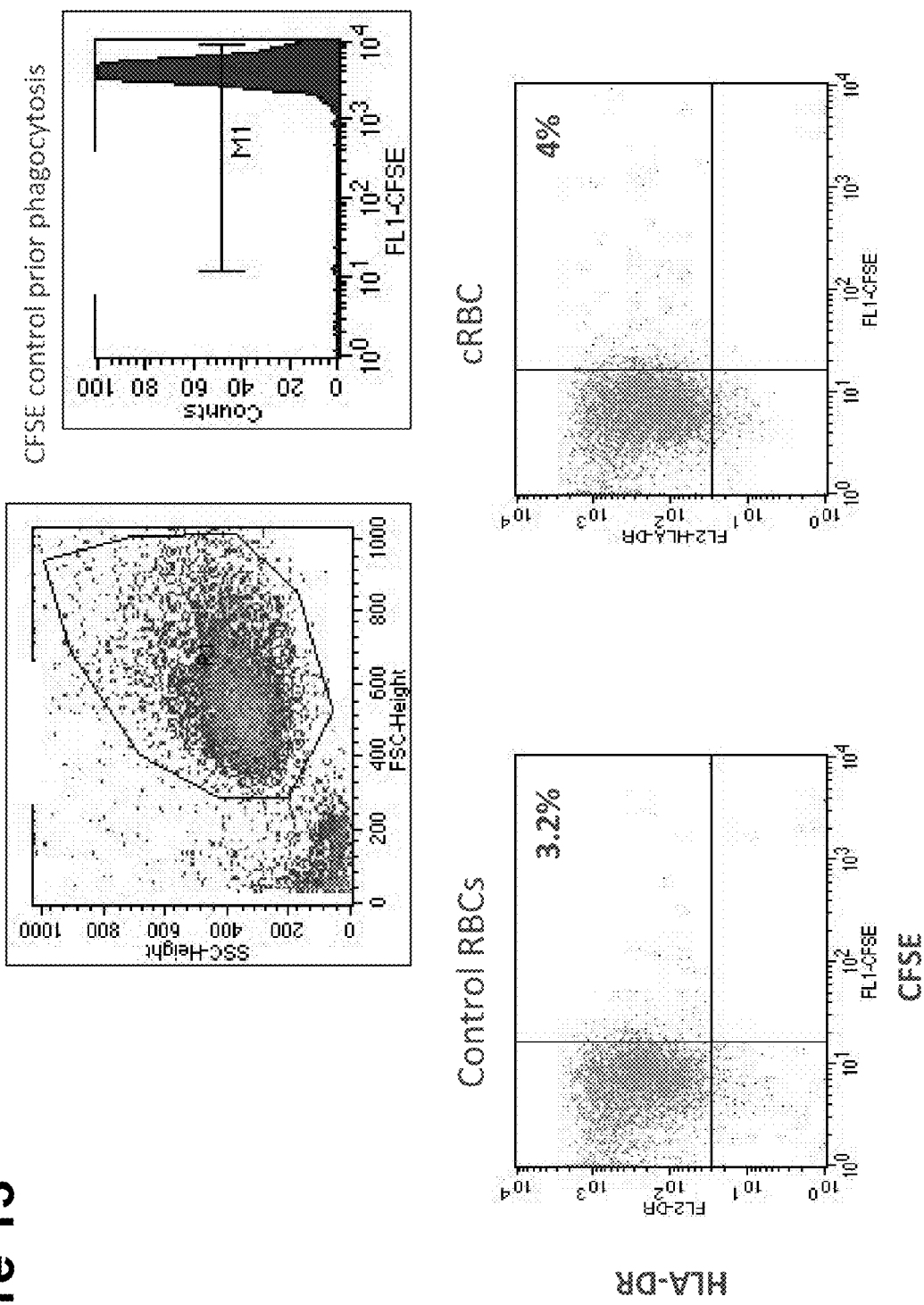
FIG. 15. Erythrophagocytosis by hu Macrophages. Control RBCs and expanded RBCs were compared for erythrophagocytosis.
Figure 18:
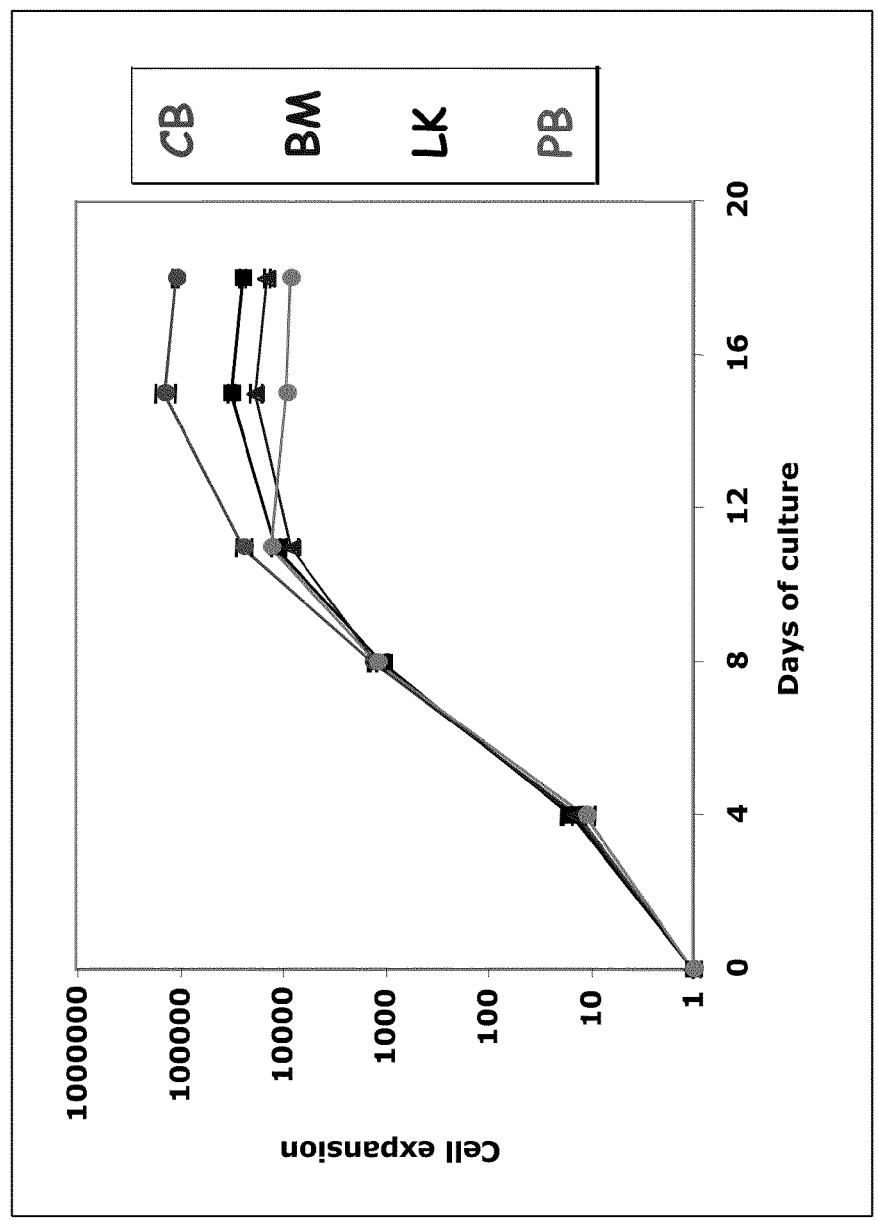
FIG. 18. Cell Expansion. The expansion of cells from various sources were examined over a number of days. CB=Cord Blood, LK=Leukocyte, BM=Bone Marrow, PB=Peripheral Blood.
Figure 19:
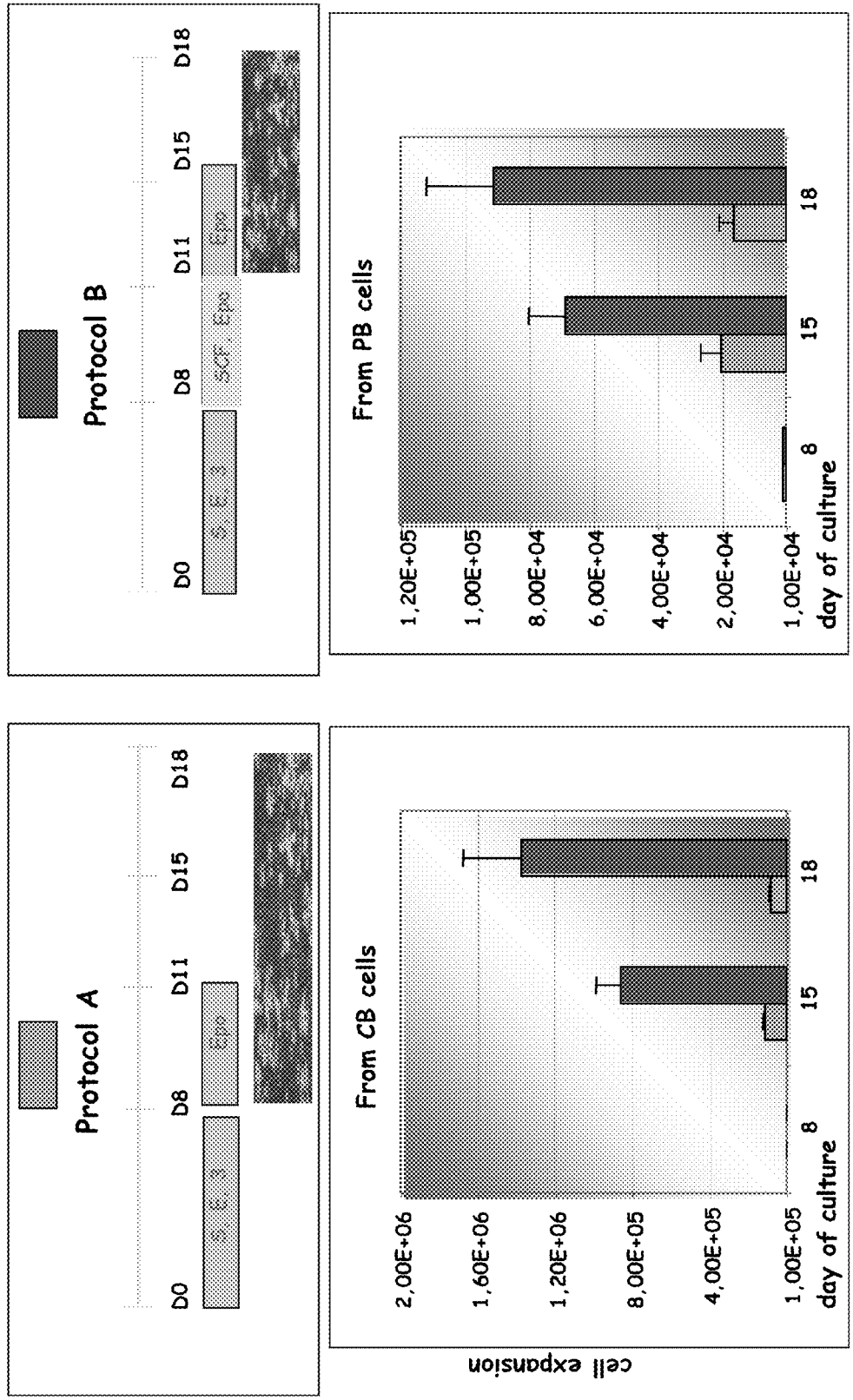
FIG. 19. Production of RBC from CD 34 Hemopoietic Stem Cells. A comparison of expansion of CB and PB cells using Protocols A and B was performed. CB=Cord Blood, PB=Peripheral Blood.
Figure 20:
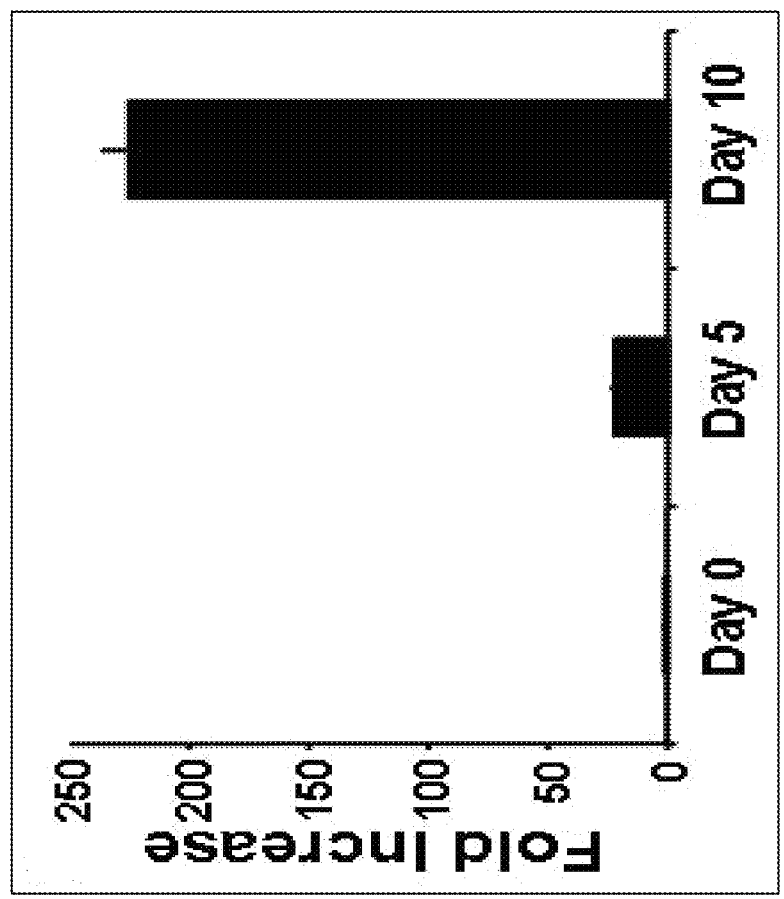
FIG. 20. Cell Expansion Results. Expansion of cells was examined at Day 5 and 10.
Figure 21:
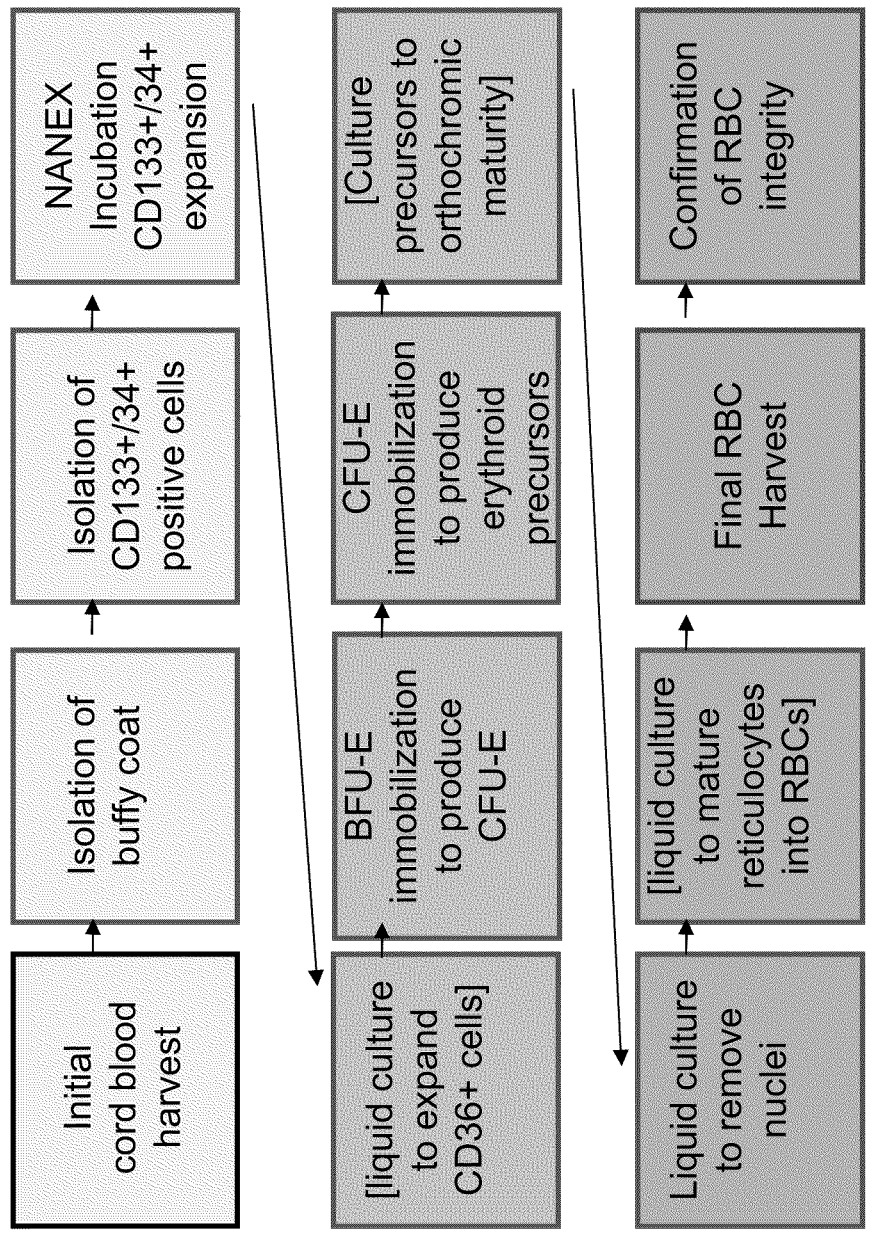
FIG. 21. Process Flow Chart for NANEX RBC Production.

To test the feasibility and efficiency of gene transfer using our expanded stem cells, we have transfected the pmaxGFP vector using Nucleofactor technology and a human CD34 cell nucleofactor kit (Amaxa Inc. program U-008) following the manufacturer's protocol. We have transfected these expanded cells and verified robust GFP expression 24-h post transfection using fluorescence microscopy. FIG. 10 demonstrated approximately 90% transfection efficiency using this approach. We subsequently cultured these transfected cells under endothelial-differentiation conditions for an additional 14 days. Microscopic examination showed that these cells appeared elongated in shape and endothelial-like in appearance (FIG. 11).

Example 7

Transfection of Expanded Stem Cells with VEGF and PDGF

Figure 4:
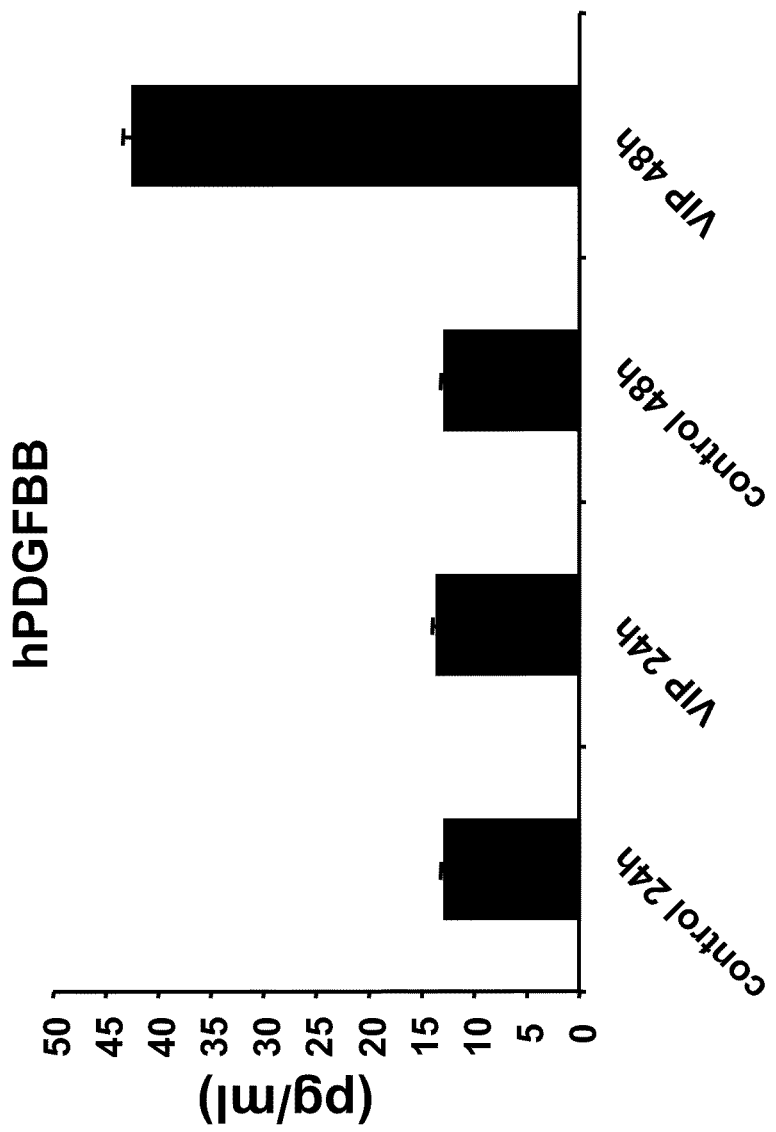
FIG. 4. Expanded cells were transfected with VIP vector (see Materials and Methods for details) and after cyto-spin cells were stained for PDGF expression using immunofluorescence technique. More than 60% cells were positive for PDGF staining. One million cells were either transfected with VIP vector or empty vector and cell culture supernatants were collected. ELISA was performed with the culture supernatants after 24 h and 48 h of transfection for PDGF secretion. After 48 h of transfection almost 4-fold induction of PDGF secretion was observed compare to the basal empty vector transfected cells.

Following a protocol similar to that previously described, we have transfected our expanded stem cells with a single coupled vector ("VIP") containing VEGF and PDGF (obtained from Dr. Blau, Stanford University, CA) and evaluated their transfection efficiency by assessing over expressed protein production (immunohistochemistry and ELISA for secreted PDGF). Using immuno-histochemical staining for PDGF, more than 60 percent transfection efficiency was demonstrated. To evaluate whether transfection resulted in PDGF secretion by these expanded stem cells, ELISA was performed from the culture supernatants both 24 h and 48 h post-transfection. After 48 h of transfection, we observed 4-fold induction of PDGF secretion compared to control-vector transfected cells (FIG. 4). These results demonstrate that we can successfully transfect expanded stem cells with the coupled VEGF/PDGF-containing vector. Moreover, these transfected stem cells are functional and can synthesize/secrete the protein of interest.

Example 8

Figure 28:
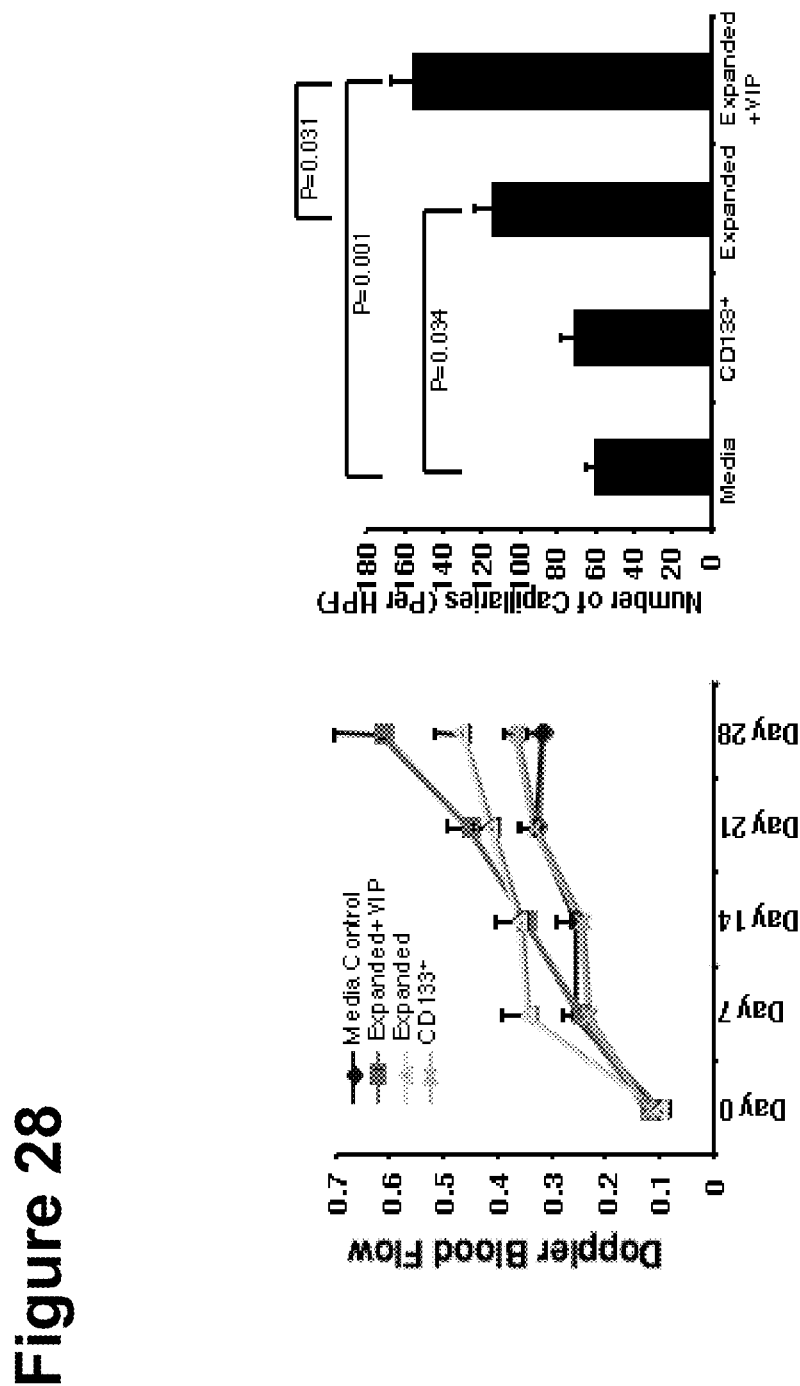
FIG. 28. Genetic modification on stem cells induces neovascularization. Blood flow and capillary number were examined in control, CD133+ cells, expanded cells and VIP transfected expanded cells.

Evaluation of Biological Effects In Vivo Using Genetically Modified Stem Cell Therapy We next sought to evaluate whether these expanded and transfected stem cells have reparative capacity in an animal host. We used a hind limb ischemic model in which we ligated the femoral artery of immunodeficient NOD/SCID mice. We analyzed four groups of animals (6-9 animals per group). Each group of animals were treated with stem cell therapy ($5\times10^5$ cells/animal, intraventricular delivery) Groups were: (1) expanded-untransfected, (40) expanded-transfected with coupled VEGF and PDGF vector (3) freshly isolated UCB-CD133+ cells or (4) media only (no cells). On post-infusion days 7, 14, 21 and 28, Doppler imaging studies were performed for the evaluation of blood flow in the hind limbs (both ligated and non-ligated). Data was analyzed using a ratio of flow between the ischemic limb and the contra lateral normal limb (FIG. 28). Results from this Doppler study indicate that blood flow was much higher in mice treated with expanded cells compared to those treated with media alone. However, in mice treated with expanded cells transfected with coupled VEGF/PDGF, blood flow was even further augmented. Capillary counts were performed as an anatomical marker of induced angiogenesis. Indeed, neovascularization was much more prominent and significantly increased in the expanded cells compare to media-alone groups and most prominent in genetically modified expanded cells verified either by immunostaining or total capillary counts. Taken together these data demonstrate that genetically modified cells with angiogenic factors were significantly potent than that of unmodified cells.

Example 9

Detection of Injected Stem Cells in the Ischemic Region in Our Hind Limb Ischemic Mouse Model We next sought to verify that our nanofiber-expanded stem cells could physically migrate and respond to ischemic signals to facilitate local therapeutic benefit, we transfected a GFP containing vector (as described in the previous section). $5 \times 10^5$ GFP vector or empty vector transfected cells were injected into hind limb ischemic mice via intra-myocardial delivery. 36 h after cell delivery, mice were sacrificed and organs were harvested. Immunohistochemical analysis was performed on fixed and paraffin-embedded tissue sections using an anti-GFP Ab. Appropriate controls were also evaluated. We could detect GFP positive stem cells in the lung, spleen and bone marrow. Interestingly, we could also detect GFP positive cells into the ischemic tissue area indicating the homing of these stem cells. We could not detect GFP positive cells into kidney, liver or brain tissues tested (data not shown).

In summary, we demonstrated that nanofibers can serve as an effective substrate to promote the expansion of functional HSCs that retain properties of their freshly-derived counterparts. Expanded cells are more potent in mediating neovascularization in a hind limb ischemic model compare to freshly isolated CD133+ cells. Furthermore, expanded cells genetically modified with proangiogenic VIP vector showed dramatic improvement in neovascularization. We have also demonstrated that our expanded cells maintain the potential to differentiate into endothelial or smooth muscle lineages and can migrate to distant ischemic zones to provide local beneficial effects.

Example 10

Optimizing NANEX Nanofiber Culturing Conditions to Determine Optimal Progenitor Cell Source (CD133+ or CD34+) for Self Renewal and Differentiation Herein Applicants disclose technology that will provide a continuous manufacturing system to enable the production of fresh universal donor red blood units within an automated self-contained unit using a self-renewing starting population of progenitor cells. An effective development of manufacturing capabilities to grow universal donor "O-negative" red blood units will allow direct application in acute care settings of dramatic blood loss, without violating the FDA's concerns involving patient consent. This solution is both technologically attainable and desirable from a clinical and regulatory standpoint.

Herein Applicants describe methods to isolate and expand early hematopoietic stem and progenitor cells using a nanofiber-based culture system. This system causes erythroid differentiation and produces mature red cells using a combination of a 3D modular perfusion bioreactor and liquid culture. The resulting red cells may be stored and analyzed to validate their characteristics.

Expansion of CD133+/CD34+ Cells:

Applicants have confirmed the NANEX system's capabilities to ex-vivo expand early progenitor (CD133+ and CD34+) cells with much greater efficiency than previous models of cell culturing. The team has also confirmed at least a 4500 fold total cell expansion at 10 days, with 20% of the population expressing erythrocyte markers (prior to actively administering differentiation factors). 1,2

CD133 is generally considered a marker for more primitive cells. It is co-expressed on the majority of CD34+ cells. Our preliminary studies showed that the aminated nanofibers promoted efficient expansion of UCB derived CD133+ and CD34+ HSCs, suggesting that functionalized PES nanofibers are superior substrate for ex vivo HSC expansion.1,2 One may optimize the culture condition for CD133+/CD34+ cell expansion as follows. One may prepare a set of nanofibers as identified from our previous studies 1,2 with defined diameters and with HSC-adhesion property by conjugating amino groups and fibronectin to fiber surfaces. Following first round of expansion for 10 days cells will be harvested as described earlier 1,2 and second ex vivo expansion culture to evaluate the fold expansion, proliferation, phenotype maintenance and differentiation of CD133+/CD34+ cells, one may identify the best culture condition for efficient and robust expansion outcomes in serum-free culture, and evaluate the differentiation potential of nanofiber-expanded CD133+/CD34+ cells in vitro. Culture variables to be altered include media components, temperature, incubation time, and percentage carbon dioxide. One may also alter the preparation of the nanofibers as disclosed herein.

Experimental Methods

CD133+/CD34+ Cells Isolation, Recombinant Cytokines and Culture Medium.

Mononuclear cells may be isolated by Ficoll density gradient centrifugation as described earlier.1,2 Briefly, cells may be incubated with CD133+/CD34+ (terminally differentiated endothelial cell as a control) specific magnetic beads per manufactures instructions (AutoMACS, Miltenyi). CD133+/CD34+ cells selected from UCB may be enumerated and characterized by flow cytometry. Selected cells may be characterized by specific surface markers, including CD133, CD34, CD31, CXCR2/CXCR1 (IL-8 receptors), and KDR (VEGFR2) to determine purity and surface characteristics of cells after bead selection3. Recombinant human stem cell factor (SCF), Flt-3 ligand (FL), thrombopoietin (TPO) and interleukin-3 (IL-3) may be purchased from StemCell Technologies (Vancouver, BC, Canada). Media used for cell expansion (StemSpan SFEM Medium), colony forming cell assay (MethoCult GF+H4435) and LTC-IC assay (MyeloCult H5100) may also be purchased from StemCell Technologies.

CD133+/CD34+ Cell Culture.

Different nanofiber meshes (diameter of 12 mm) may be fixed in the wells of a 24-well tissue culture plate. Eight hundred CD133+/CD34+ cells may be seeded onto each scaffold in 0.6 mL StemSpan™ serum-free expansion medium supplemented with 40 µg/mL LDL, 100 ng/mL SCF, 100 ng/mL Flt3, 50 ng/mL TPO and 20 ng/mL IL-3. Cells may be cultured at 37° C. in an incubator for 3 to 10 days without medium change. Similar culture may also be performed on tissue culture polystyrene surface (TCPS), which serves as a positive control in this study. Cells may be harvested after 10 days of expansion. All substrates may be washed once with non-trypsin cell dissociation solution and twice with 2% FBS Hanks' buffer at 5-10 min intervals between each wash. The cell suspensions may then be concentrated through centrifugation at 500×g for 10 min. Aliquots of the concentrated cells may then be used for cell counting by a hematocytometer and flow cytometry analyses. One may modify this culture condition by changing the cell number and volume to accommodate automated culture using a bioreactor as described in this proposal. One may also assess the self renewal capability of Nanex cells by re-culturing them for at least 5 rounds on culture on new nanofiber coated plates to test the self renewal capability of ex vivo expanded cells.

Surface Phenotyping of Nanex 133+ or 34+ Cells:

The Nanex 133/34 cells may be characterized by flow cytometric analysis for change in surface phenotype. Briefly, cell surface markers may be blocked with FCR Blocking Reagent (1:5; Miltenyi Biotec) and incubated for 20 min at 4° C. with the following antibodies: anti-CD34-PE, and anti-CD133/2 FITC (all from Miltenyi Biotec). CD117 labeling may be performed using anti-CD117 antibody (clone YB5.B8; 1:100; BD Parmingen, BD Bioscience, San Diego, Calif., USA). Isotype controls may be purchased from BD Pharmingen. After incubation cells may be washed with MACS sorting buffer and analyzed using a FACS Calibur flow cytometer (Becton Dickinson, Heidelberg, Germany). Dead cells may be excluded via propidium iodide staining. Data analysis may be performed with BD CELLQuest software.

In accordance with the disclosures herein, one may standardize the best nanofiber configuration and $2 \times 10^6$ fold ex vivo expansion of CD133+/CD34+ cells. This information together with the comparison between adherent and suspension populations allows one to optimize the differentiation of expanded cells to RBC directly on functionalized nanofiber scaffolds or in a liquid suspension culture. Nanofiber-expanded UCB CD133+/CD34+ cells should maintain functional integrity.

Example 11

Ex Vivo Expansion of Cord Blood CD133+/CD34++ Cells—Arteriocyte's 4500-Fold Cell Factory The nanofiber system yields 4500 fold expansion of total cells (TC population) and 805 fold CD34+ populations of progenitor cells in a 10-day culture in preliminary studies of human UCB CD133+ and CD34+ cells cultured using the NANEX nanofiber system. The expanded CD133+ and CD34+ cells successfully reconstitute hematopoiesis in NOD/SCID mice at efficiencies higher than that of standard suspension culture on tissue culture plates.[1,2,28,40]

An important characteristic of this nanofiber-based cell expansion technology is that these functional nanofibers, mimicking part of the bone marrow stem cell niche function, offers a mechanism for HSC phenotype maintenance/self-renewal via nanofiber-mediated adhesion. Cells expanded on this nanofiber niche consist of two distinct populations of cells: those which adhere to nanofibers (adherent fraction accounting for ~46% of total expanded cells) and those that release into suspension cells (suspension population accounting for ~54% of total expanded cells). Cell phenotypic analysis showed that the adherent population expressed significantly higher percentage of progenitor markers (CD34+ CD45+, 43.8%), compared with the non-adherent cell population (21.9%, p<0.05).

In contrast, the suspension cell population expressed higher percentage of erythroid marker (46.2% of CD71 high, 35.7% of GlyA) than adherent population (14.1% of CD71 high, 12.4% of GlyA, p<0.05). The overall percentage of erythroid-committed cells was 21.5%. CFU assay also indicated significant commitment of the suspension cells towards the erythroid lineage compared to the adherent cells. These characteristics suggest that this nanofiber scaffold provides important outcomes similar to bone marrow niche. This study highlights the importance of cell-scaffold interactions as a new approach in modulating HSC maintenance and lineage commitment, in addition to cytokine modulations typically used in the literature. To Applicants' knowledge, this is the first evidence directly associating cell-substrate adhesion with HSC expansion and phenotype maintenance. By establishing weak adhesion to the substrate, HSCs can be expanded more efficiently and easily harvested. Such a nanofiber system facilitates continuation/automation of production of RBCs—cells adhered to nanofibers were maintained in self-renewal cycle; and cells that detach from nanofibers differentiate towards erythroid lineage.

Example 12

Purification, Functional Characterization and Ex Vivo Expansion of UCB Derived CD133+ or CD34+ Cells on Nanofibers Human umbilical cord blood CD133+/CD34+ sorted cells were isolated from fresh cord obtained from CWRU Hospital. Cells were cultured at 37° C. in an atmosphere containing 5% $CO_2$ for 10 days without medium change as described earlier 41. Similar cultures were also performed on tissue culture polystyrene surface (TCPS), which serve as a positive control in this study. Cells were harvested after 10 days of expansion and washed once with non-trypsin cell dissociation solution and twice with 2% FBS Hanks' buffer at 5-10 min intervals between each wash. Aliquots of the concentrated cells were then used for cell counting by a hematocytometer, flow cytometry analysis, as well as for further studies.

Example 13

Purification and Surface Phenotyping of Nanex 133+ Cells

Flow cytometric analysis was performed for the characterization of nanofiber scaffold expanded cells at day 10 using various conjugated antibodies as stated in one or two color staining as described earlier.[1,2,41] As shown above, the CD34 marker is generally expressed by primitive hematopoietic progenitor cells, while CD45 marker is expressed on all cells of hematopoietic origin with the exception of red blood cells and their immediate precursors.

TABLE 1

Characterization of nanofiber scaffold expanded cells.

|  | Before Culturing (%) | After 10 Days Nanex Culture (%) |
|---|---|---|
| Control | <0.04 | <0.04 |
| CD133+ | 97.00 | 23.3 |
| CXCR4 | <0.10 | 96.8 |

TABLE 1-continued

Characterization of nanofiber scaffold expanded cells.

| | Before Culturing (%) | After 10 Days Nanex Culture (%) |
|---|---|---|
| vWF | N/A | 46.4 |
| CD3 | <0.10 | <0.10 |

Flow cytometric analysis was performed for the characterization of nanofiber scaffold expanded cells at day 10 using various conjugated antibodies as stated in one or two color staining. The table is a representative of the three independent analyses of the expanded cells.

Confirmatory staining using DAPI and DiI-AcLDL uptake were performed on the Nanex 133+ expanded cells to show the functional integrity of expanded cells. Both fresh and Nanex CD133+ cells were transwell plated and migratory capacity was assessed in the presence or absence of stromal derived factor SDF).

Example 14

In Vitro Functional Evaluation of Nanex 133+ Expanded Cells

A statistically ($P<0.001$) significant (almost two-fold) increase in migration was observed for the nanofiber expanded cells compare to the freshly isolated cells in the presence or absence of SDF. Almost 24% and 93% of the total cells expressed CD133+ and CD34+ respectively (Table 1). Mild to moderate expression of other myeloid markers were observed such as CD14, CD86, vWF, CD31 or Mac-1. These expanded cells do not express any activation markers (CD69) or pan T cell markers (CD3) molecules on their surface, indicating that these expanded cells retain their stem cell characteristics.

Example 15

In Vivo Evaluation of Nanex 133+ Expanded Cells

We have developed in vivo biologic assessment capabilities to track the fate of Nanex 133+ cells in NOD/SCID mouse model. Cell delivery via intra-myocardial delivery or tail vein injection to assess engraftment of transplanted Nanex 133+ cells. This model is directly applicable to serial tail vein sampling for functional assessment of the Nanex expanded erythrocytes.

Example 16

Cultured RBC Properties and Function

In spite of intense research in understanding the terminal erythropoiesis and enucleation, only partially elucidation of this mechanism has been described 1-3. To Applicants' knowledge, an ex vivo experimental system capable of generating substantial expansion of progenitor cells and differentiation to fully mature human RBCs in large quantities (two million fold) has not been reported prior to this disclosure. Earlier attempts by several investigators to develop an automated erythrocyte progenitor expansion and differentiation to fully mature RBC has been hindered by the fact that the successful expansion is not accompanied by successful differentiation and functional maturation without co-culture with Mesenchymal cells or other cell type.10,11 12,13 Recently, the impact of the ex vivo microenvironment on the terminal maturation of erythroid cells as well as on hemoglobin synthesis has been reported by several investigators 6-12.

Even though in vitro generated RBCs have all the characteristics of functional, native, adult RBCs in terms of enzyme content, membrane deformability and the capacity to fix and release oxygen, the three step process that was used in achieving this success may be costly, and full automation and possible technical difficulties in co-culture used in prior studies may hinder the success of such methods of generating RBCs.

Surface Phenotyping of Differentiated Erythrocyte Progenitor Cells

The surface phenotyping of differentiated erythrocyte progenitor cells may be carried using CD34, CD13, CD15, CD19, CD38, CD45 antibodies and GlyA using flow cytometry. The Milan-Mulhouse gating method may be used for cell enumeration, where a double gating (CD34+CD45+) strategy was used to identify the primitive hematopoietic progenitor cell population in the ex vivo expansion cultures. The CD34 marker is generally expressed by primitive hematopoietic progenitor cells, while CD45 marker is expressed on all cells of hematopoietic origin with the exception of red blood cells and their immediate precursors.

The morphological characteristics of differentiated cells may be studied by May-Grünwald-Giemsa reagent staining and analyses, whereas enucleated cells may be monitored for standard hematological variables including the MCV (fl), Mean Cell Hemoglobin (MCHC) (%) and MCH (pg/cell) using an XE2100 automat (Sysmex, Roche Diagnostics).

Cells may be labeled with unconjugated or fluorescein isothiocyanate- or phycoerythrin-conjugated antibodies. Antibodies to CD71 (Dako) and to CD45, CD36 and CD34 (Immunotech) may be used for phenotyping and cells may be stained with the vital nucleic acid dye LDS-751. Analyses may be done on FACSCalibur flow cytometer (Becton Dickinson) using Cell Quest software.

Semisolid Culture Assays

BFU-E, CFU-E and CFU-GM progenitors may be assayed as previously described.12,13 to assess the differentiation stage of erythrocyte progenitor population after differentiation.

Deformability Measurements

The differentiation of expanded reticulocytes into mature RBCs may be tested by deformability. The reticulocytes obtained on day 15 of culture may be separated from nucleated cells by passage through a deleukocyting filter (Leucolab LCG2, Macopharma) and the enucleated cells may be examined by ektacytometry, a laser diffraction method. In the ektacytometer (Technicon, Bayer), cells may be suspended in 4% polyvinylpyrrolidone solution then exposed to an increasing osmotic gradient (from 60 to 450 mosM). The change in their laser diffraction pattern may be recorded. The photometric measurement produces a signal termed the deformability index (DI). Analysis of the DI curve provides a measure of the dynamic deformability of the cell membrane as a function of the osmolality at a constant applied shear stress of 170 dynes/cm.

Enzyme Activities

Digitonin (0.2%) may be added to erythrocytes obtained after leukocyte depletion and hemoglobin may be quantified by spectrophotometry using Drabkin's reagent. Glucose-6-phosphate dehydrogenase and pyruvate kinase activities may be determined by measurement of the rate of increase in NADPH absorbance at 340 nm45, using a Synchron CX4 Beckman spectrophotometer and reagents from Randox Laboratories and Roche Diagnostics, respectively. Results will be expressed in units per gram of hemoglobin.

Hemoglobin Analyses

The percentage of the various hemoglobin fractions may be measured by CE-HPLC using a Bio-Rad Variant II Hb analyzer (Bio-Rad Laboratories). Globin chain composition may be determined by RP-HPLC as previously described.

Hemoglobin Functional Properties

The Methemoglobin fraction may be determined spectrophotometrically in the near UV region (350-450 nm). Spectra may also be measured for samples equilibrated under pure CO, and after addition of potassium cyanide (final concentration of 200 mM) to the buffered solution of hemoglobin. The total heme concentration will be determined from the maximum absorption of the CO spectrum at 420 nm after addition of 200 mM potassium dithionite. Oxygen equilibrium curves may be measured by a continuous method using a double-wavelength spectrophotometer (Hemox analyzer, TCS). RBCs may be suspended in 50 mM bis-Tris buffer containing 140 mM NaCl at 37° C. and pH 7.4. The binding properties of hemoglobin may be studied by flash photolysis of solutions in 1-mm optical cuvettes. Briefly, the kinetics of the rebinding of CO to intracellular hemoglobin tetramers may be analyzed at 436 nm after photolysis with a 10-ns pulse at 532 nm as described previously.

Mixed Lymphocyte Cultures (MLR)

Our preliminary in vitro studies have shown that CB derived CD133+ cells express HLA class I and II surface molecules and elicit allogeneic T-cell proliferation by immune competent adult mononuclear cells. It is important to validate the loss of 133+/34+ expression of these cells as they differentiate. The separation process described herein should sufficiently fractionate out the immunologically active progenitor cells from the terminally differentiated universal donor erythrocytes.

Example 17

Culturing System Capability

Figure 24:
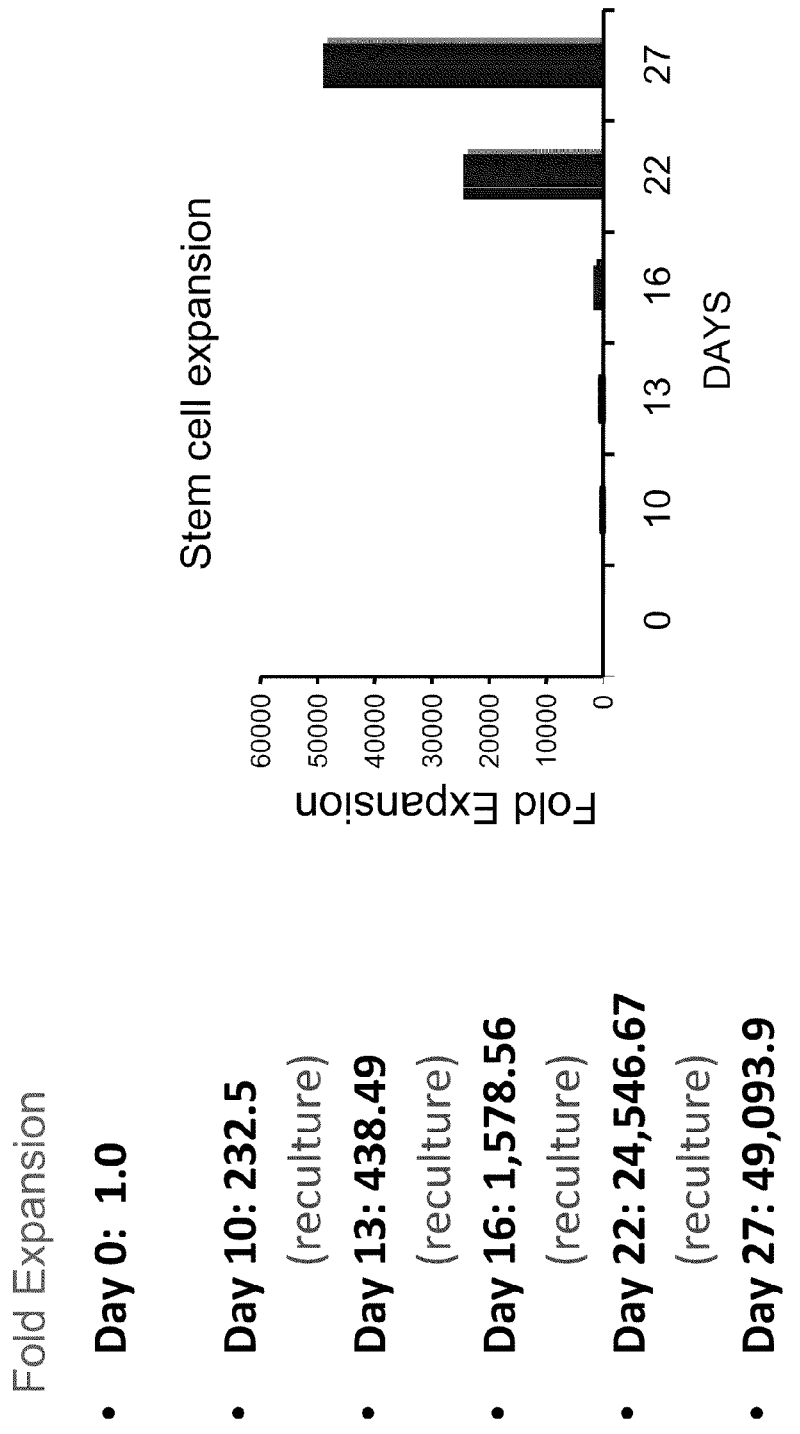
FIG. 24. Reculture of primarily nanofiber expanded CD133+ cells for further expansion. Expansion of recultured pre-expanded CD133+ cells was analyzed over 27 days.

Improved the self-renewing progenitor cell nano fiber based culturing system yielded about 5000 fold expansion in 20 days. Total cell expansion after reculture resulted in about 50,000 fold expansion in 27 days (FIG. 24). Applicants have differentiated over 80+% of nanofiber expanded cells to erythrocyte phenotype in 21/23 days span in liquid culture (FIG. 38).

Example 18

Expanded Cells Analysis

Figure 29:
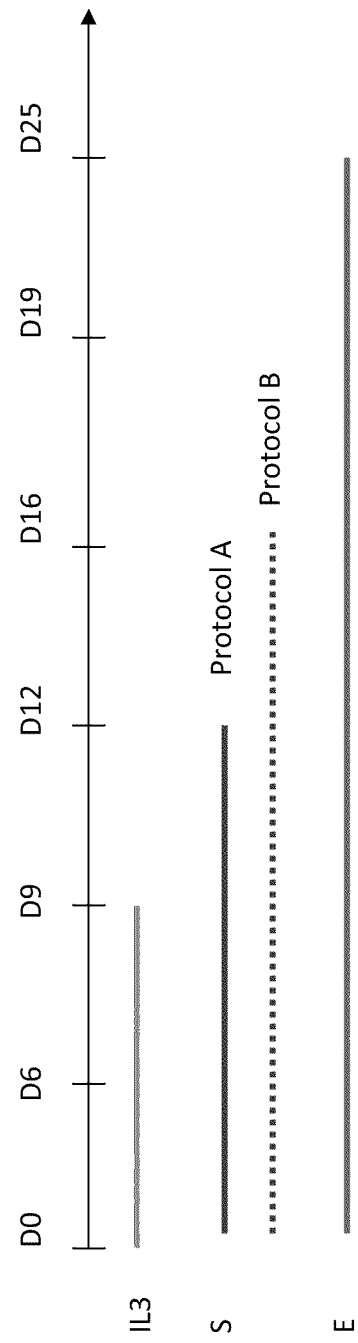
FIG. 29. Timeline and Growth Factor Requirement for NANEX RBC Production. S=Stem Cell Growth Factor 1, E=Erythropoietin, IL3=Interleukin 3.
Figure 30:
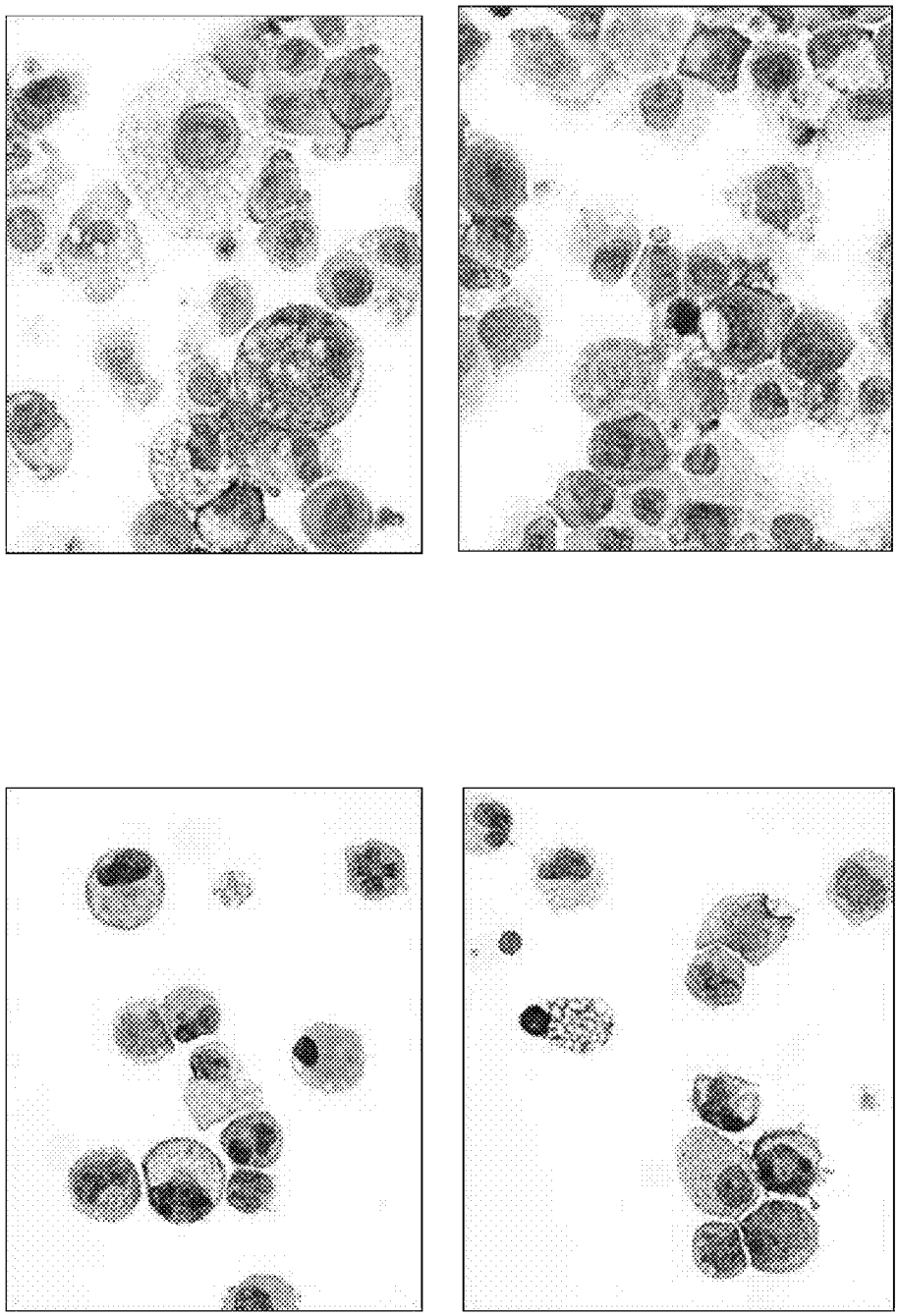
FIGS. 30-37. Cytology of expanded cells.
Figure 31:
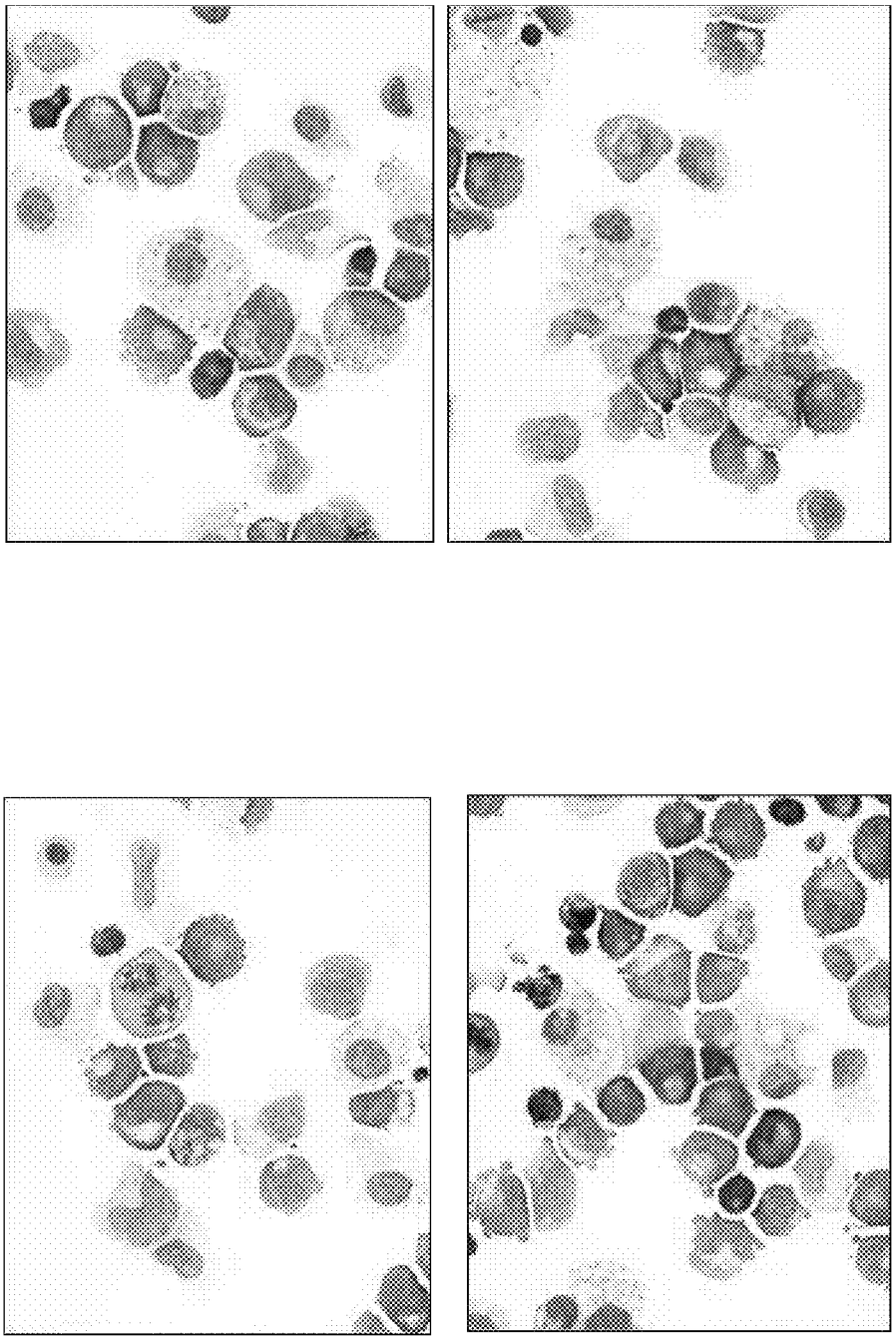
Figure 32:
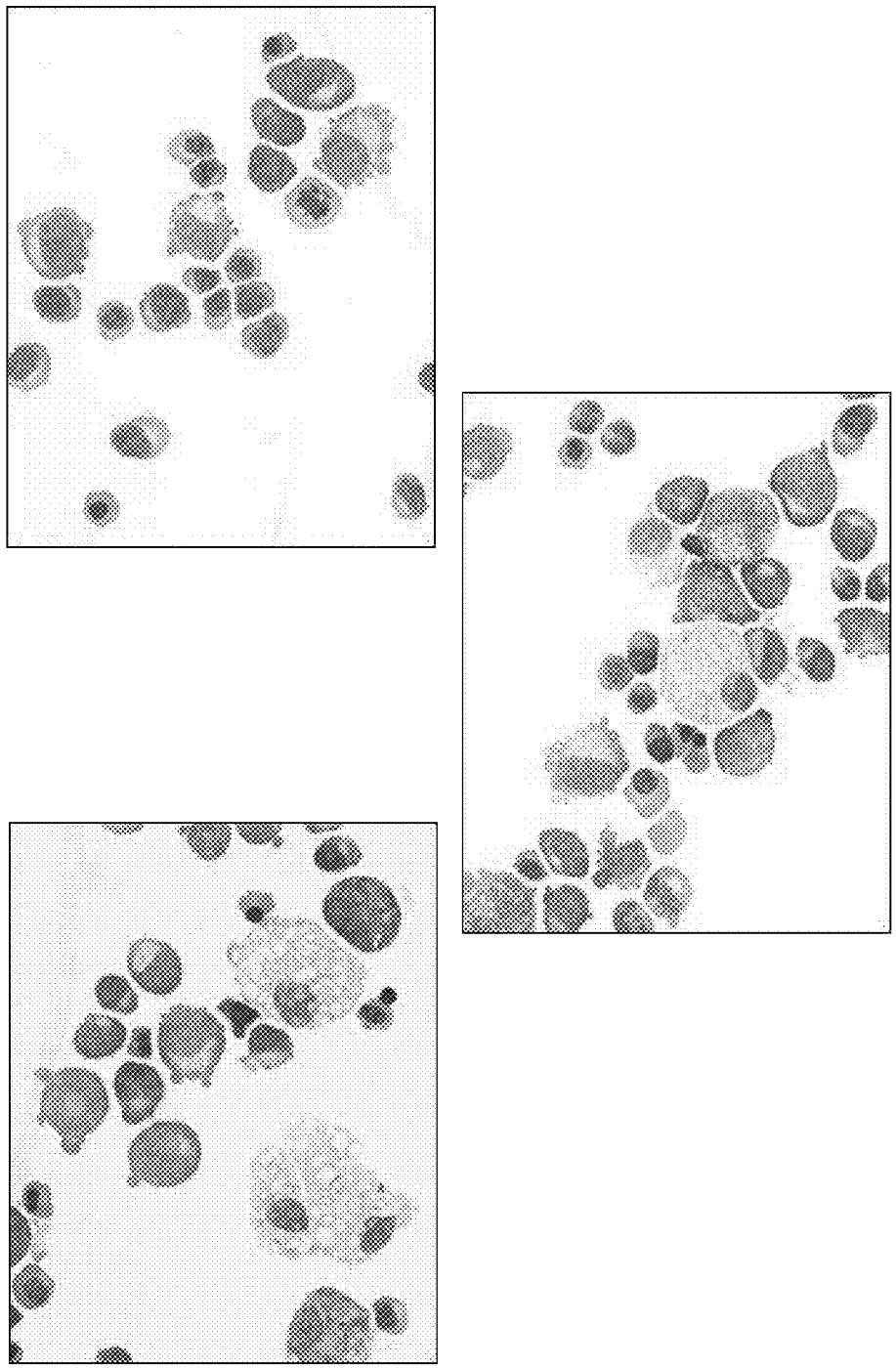
Figure 33:
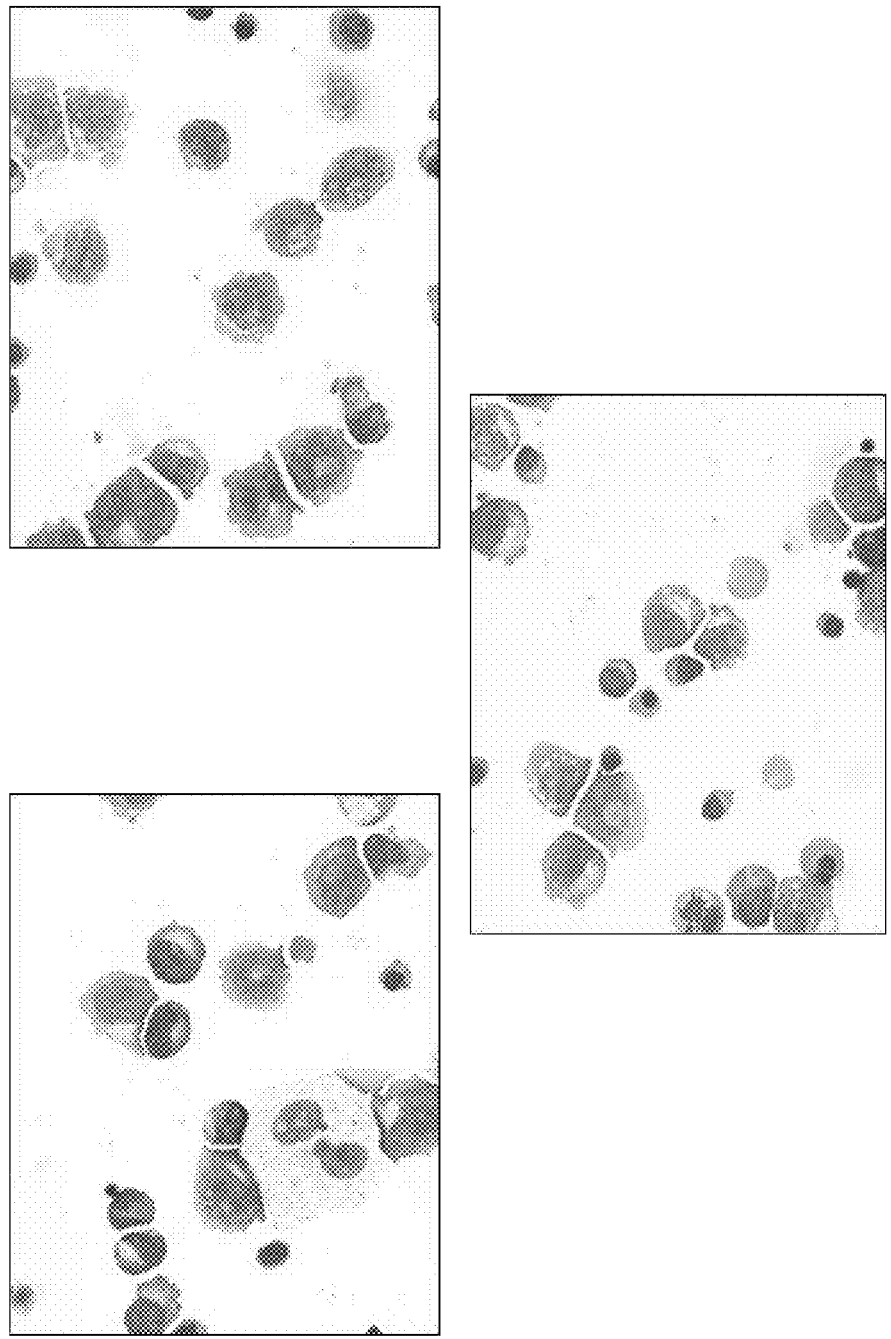
Figure 34:
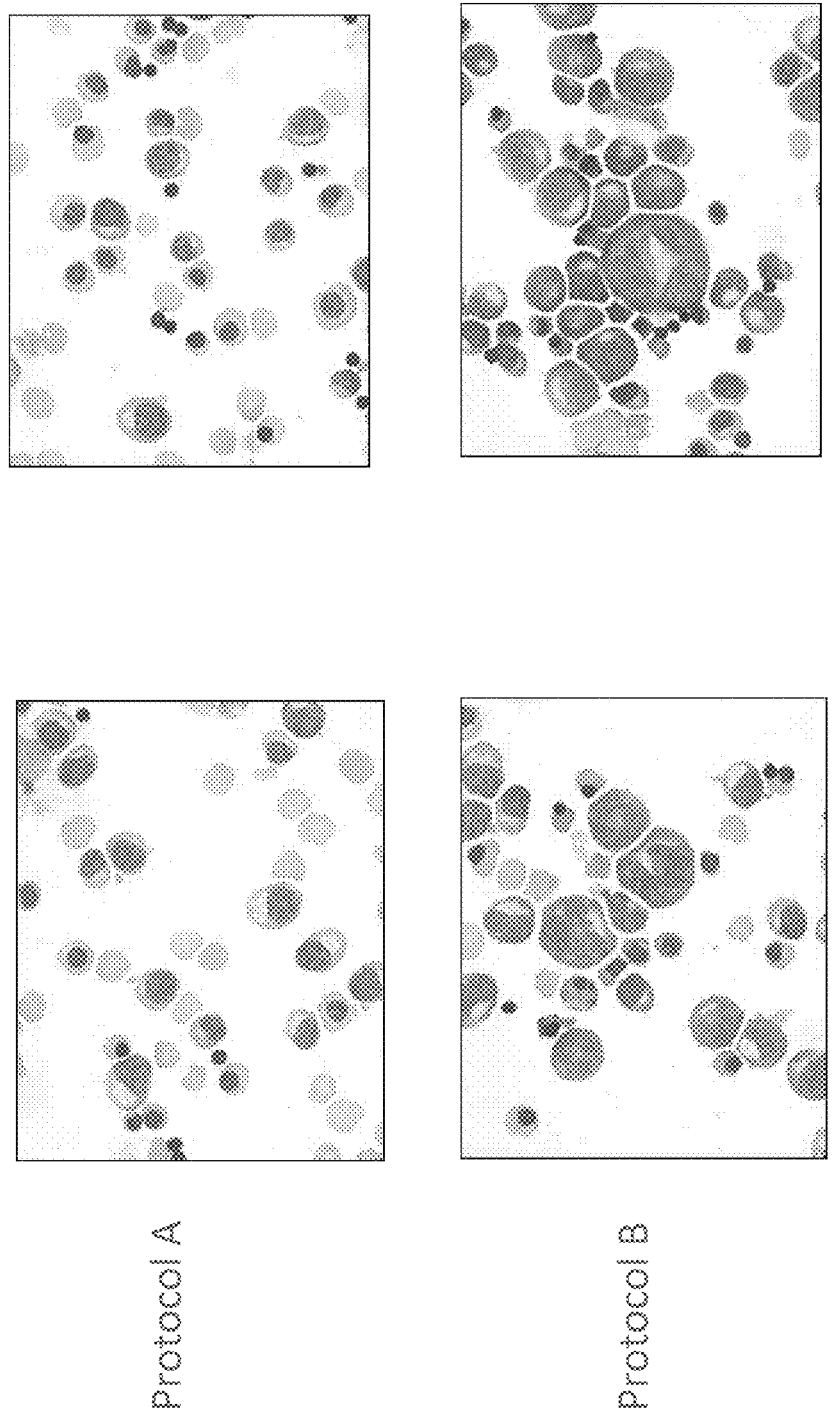
Figure 35:
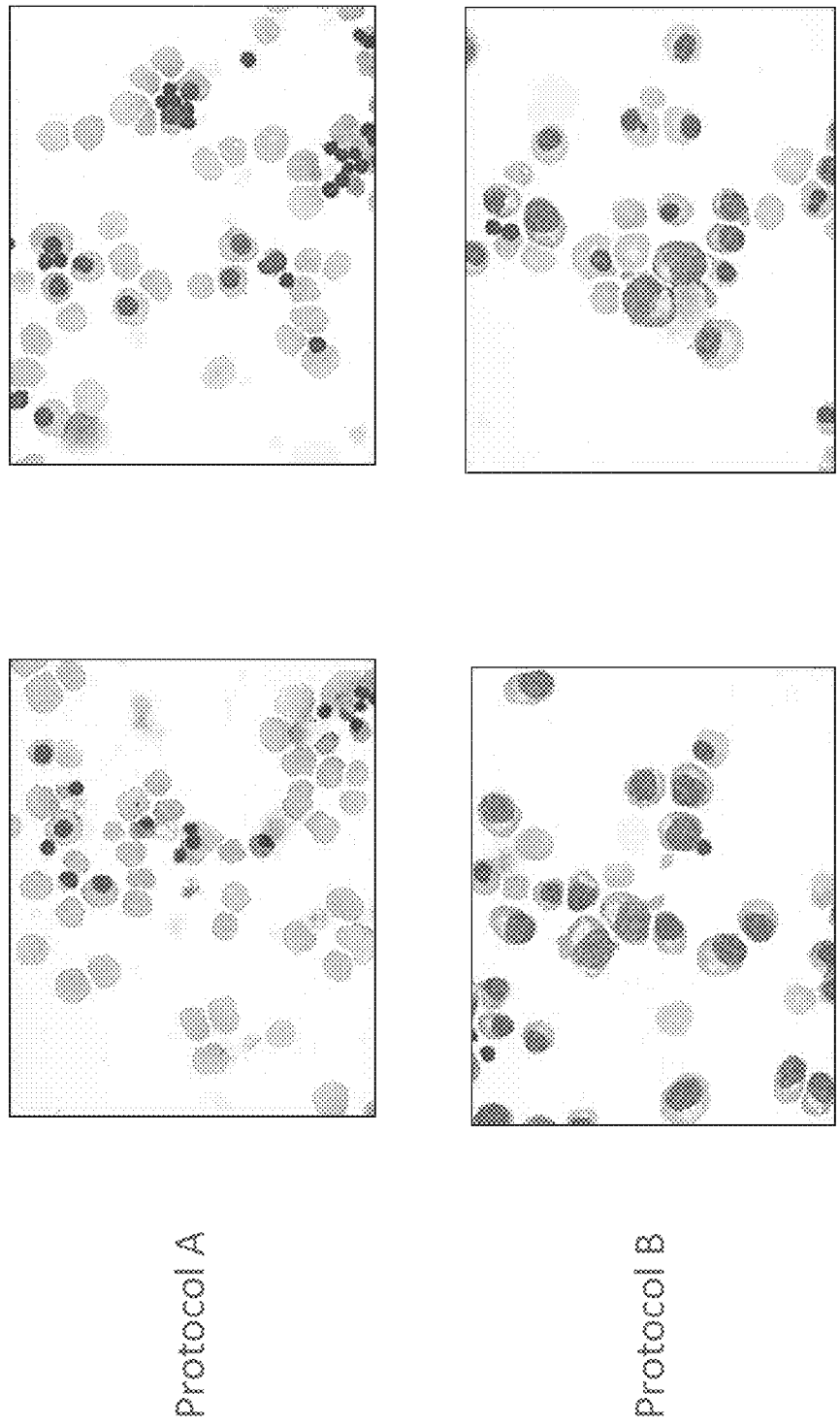
Figure 36:
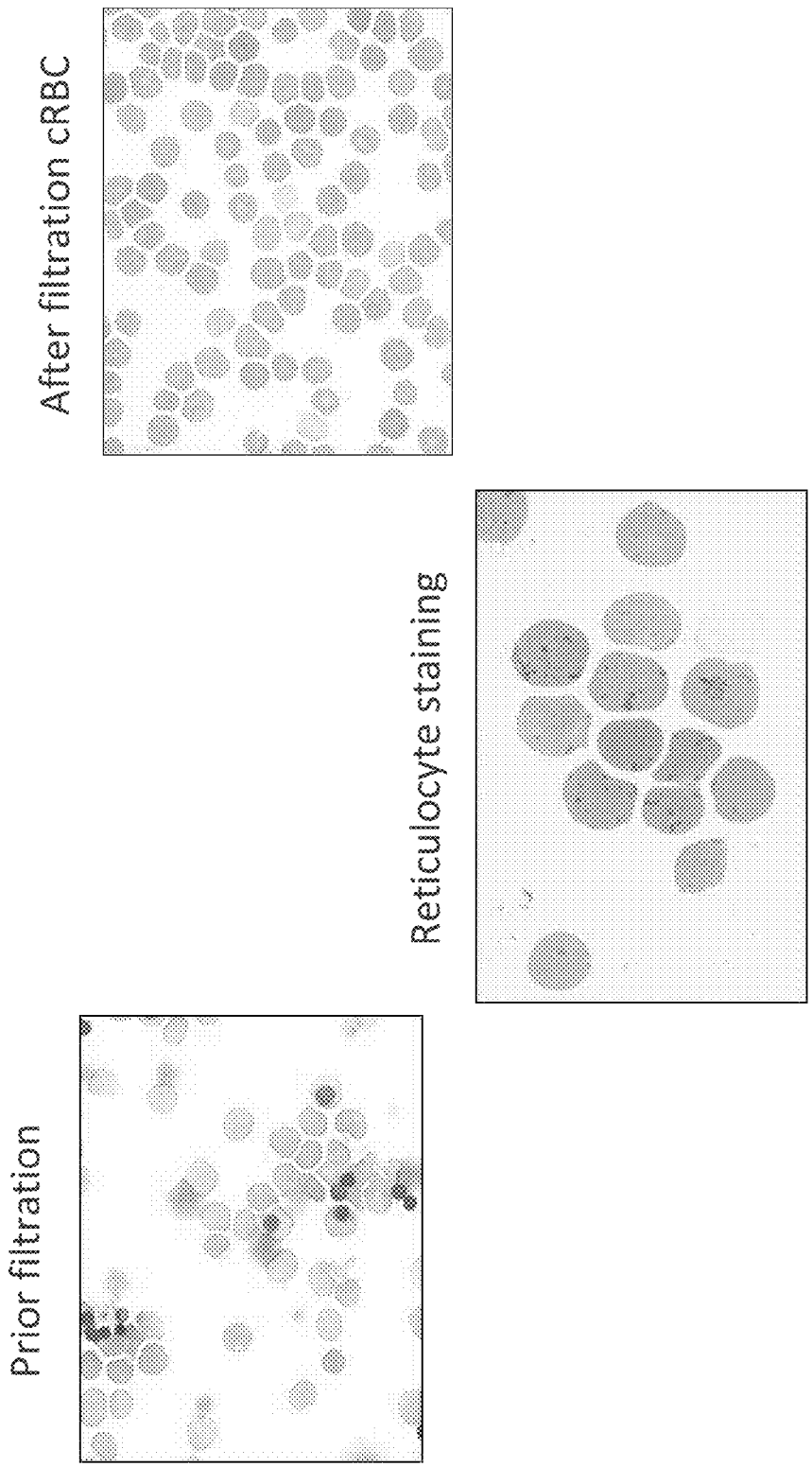
Figure 37:
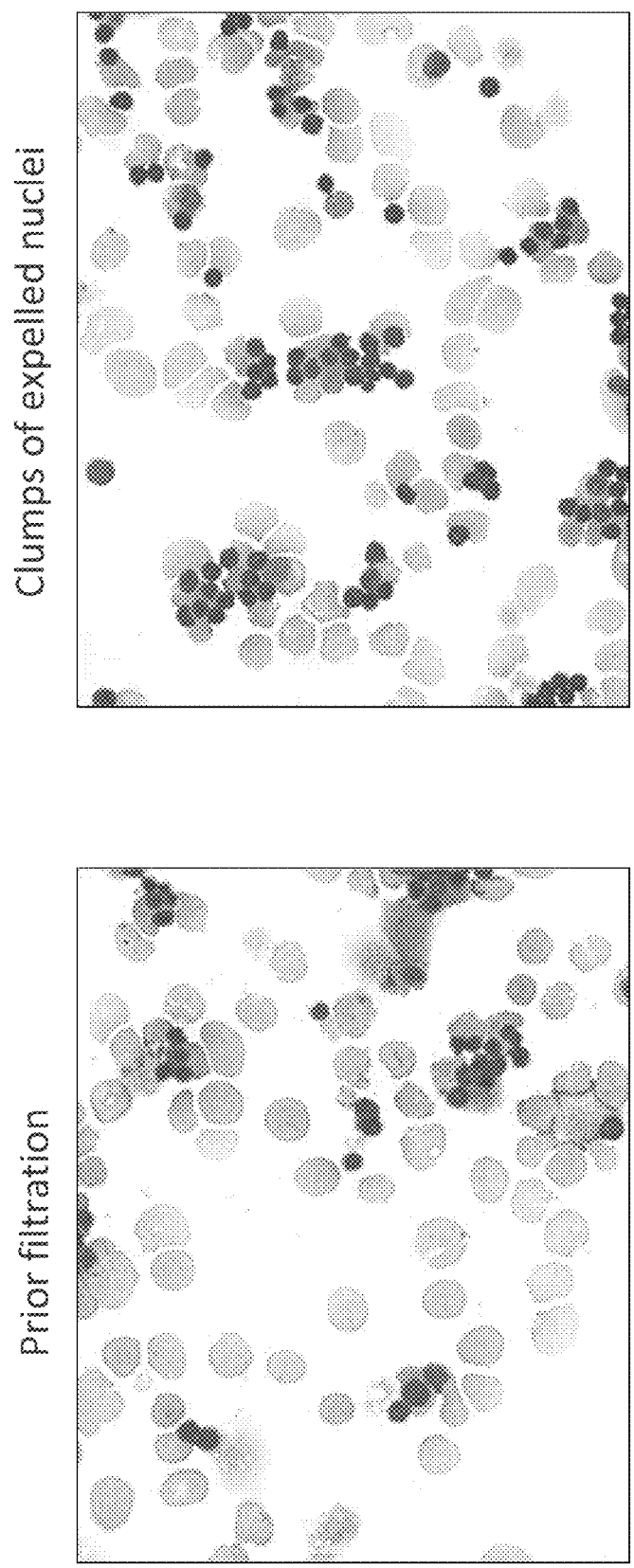

Nanofiber Expanded CD133+ cells were seeded at $5 \times 10^4$/ml at D0 and subsequently at various concentrations in defined medium for RBC production according to UPMC protocol comprising Stem Cell Growth Factor 1, Erythropoietin and Interleukin 3 for varying lengths of time. Because of a high CD117 expression SCF was maintained up to Day 16 (Protocol B) and compared to the standard protocol (Protocol A) (FIG. 29).

Protocol B resulted in greater total expansion and produced an increased number of RBCs but the percentage of RBCs of total cells was similar (FIG. 38).

Cytology was analyzed at day 0, 6, 9, 12, 16, 19, 21, and 23 (FIGS. 12 and 30-37). Further analysis of cytology, phenotype, expansion and progenitors were conducted on days 12, 16, 21 and 23 (Tables 2-6). Functional assays were performed on differentiated RBCs as described in Examples 15 and 16. Deformability, enzyme content, photodissociation, oxygen binding, erythrophagocytosis, and in vivo fate of Nanex expanded and differentiated RBCs were similar to control RBCs (FIGS. 13-17).

TABLE 2

Nanofibers Expanded Cells Characterization
Day 12

Cytology:

6% RBCs
11% acidophilic Ebl
11% polychromatophilic Ebl
32% basophilic Ebl
38% Proerythroblast
1% endo/macrophages
2% myeloid cells
Progenitors for 10e4 cells:

CFU-E:311
CFU-GM: 7
BFU-E: 125
Phenotype:

CD34 PE: 0.6%
CD133 PE: 1%
CD71 FI: 99%
CD36 FI: 94%
GlycoA: 86%
CD14 FI: 0.5%
CD43: 87%
CD31: 4.6%
CD117: 32%

TABLE 3

Nanofibers Expanded Cells
Day 16

|  | Protocol A: epo only from D12 | Protocol B: SCF + Epo from D9 |
|---|---|---|
| Cell expansion (D16 vs D0) | 1630 fold | 2878 fold |
| Total Cell expansion | 7.34 × 10e6 fold | 12.9 × 10e6 fold |
| Cytology |  |  |
| % RBC | 37% | 21% |
| % AE | 16% | 12% |
| % PE | 20% | 12% |
| % BE | 23% | 36% |
| % ProE | 4% | 19% |
| Phenotype |  |  |
| CD117 | 1% | 15% |
| CD133 | 0.7% | 1.6% |
| CD36 | 71% | 90% |
| GlycoA | 99% | 92% |
| CD71 | 97% | 99% |
| CD43 | 34% | 60% |
| CD31 | 2% | 1% |
| Progenitors for $10^e4$ cells |  |  |
| CFU-E | 2 | 182 |
| BFU-E | 0 | 49 |
| CFU-Gm | 1 | 11 |

TABLE 4

Nanofibers Expanded Cells
Day 19

|  | Protocol A | Protocol B |
|---|---|---|
| Cell expansion (D19 vs D0) | 1614 fold | 8951 fold |
| Total Cell expansion | 7.26 × 10e6 fold | 40.3 × 10e6 fold |
| Cytology |  |  |
| % RBC | 73% | 26% |
| % AE | 12% | 7% |
| % PE | 11% | 19% |

TABLE 4-continued

Nanofibers Expanded Cells
Day 19

| | Protocol A | Protocol B |
|---|---|---|
| % BE | 4% | 42% |
| % ProE | 0% | 6% |
| Phenotype | | |
| CD117 | 0% | 1.8% |
| CD133 | 0.7% | 1.7% |
| CD36 | 32% | 78% |
| GlycoA | 99% | 99% |
| CD71 | 89% | 98% |
| CD43 | 7% | 62% |
| CD31 | 0.5% | 0.7% |

TABLE 5

Nanofibers Expanded Cells
Day 21 Protocol A

| | Protocol A |
|---|---|
| Cell expansion (D + 19 vs D + 0) | 1350 fold |
| Total Cell expansion | 6.1 × 10e6 fold |
| Cytology | |
| % RBC | 81% |
| % EA | 16% |
| % PC | 3% |
| % EB | 0% |
| % ProE | 0% |
| Phenotype on filtered cells | 100% cRBC |
| GlycoA | 99% |
| CD36 | 18% |
| CD71 | 61% |
| Rh | 99% (MFI: 797) |
| Calpaine (esterase activity) | 97.5% |
| Standard hematological variables | Sysmex analyser |
| MCV | 156 fL |
| MCHM | 30.8 g/dL |
| MCH | 48 pg/cell |
| RET | 88% |
| Erthrophagocytosis | On human macrophages |
| Controls | 8.7% ± 5.5% |
| D1A filtered | 7.3% |

TABLE 6

Nanofiber Expanded Cells
Day 23 Protocol B

| | Protocol B |
|---|---|
| Cell expansion (D23 vs D0) | 9622 fold |
| Total Cell expansion | 43.3 × 10e6 fold |
| Cytology | |
| % RBC | 82% |
| % EA | 16% |
| % PC | 2% |
| % EB | 0% |
| % ProE | 0% |
| Phenotype | |
| GlycoA | 100% |
| CD36 | 28% |
| CD71 | 81% |

TABLE 6-continued

Nanofiber Expanded Cells
Day 23 Protocol B

| | Protocol B |
|---|---|
| Standard hematological variables | Sysmex analuser |
| MCV | 153 fL |
| MCHM | 32.5 g/dL |
| MCH | 40.2 pg/cell |
| RET | 80% |

Example 19

Bioreactor Process Flow

Figure 44:
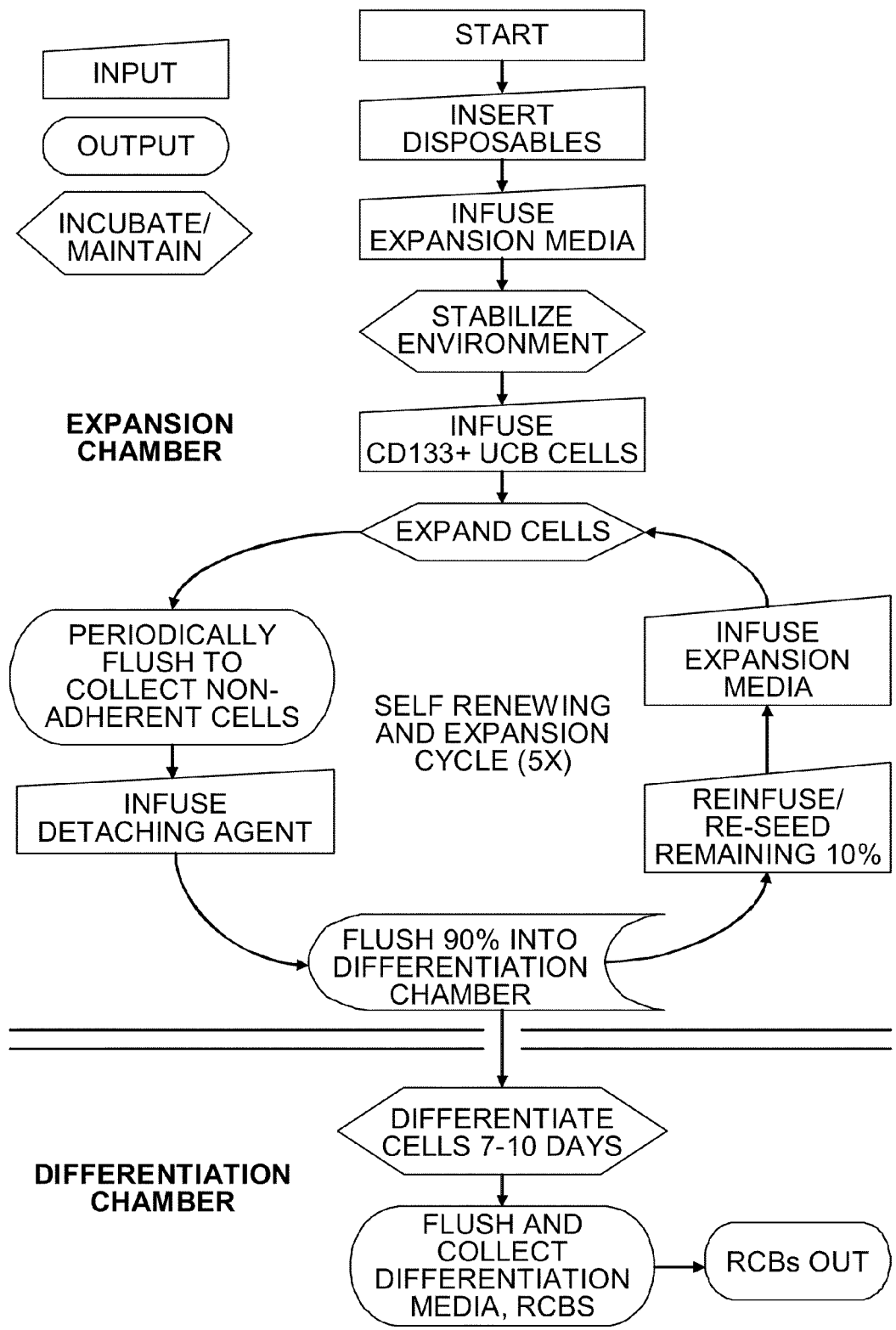
FIG. 44. Process Flow Chart for RBC Production using a Bioreactor Device.
Figure 45:
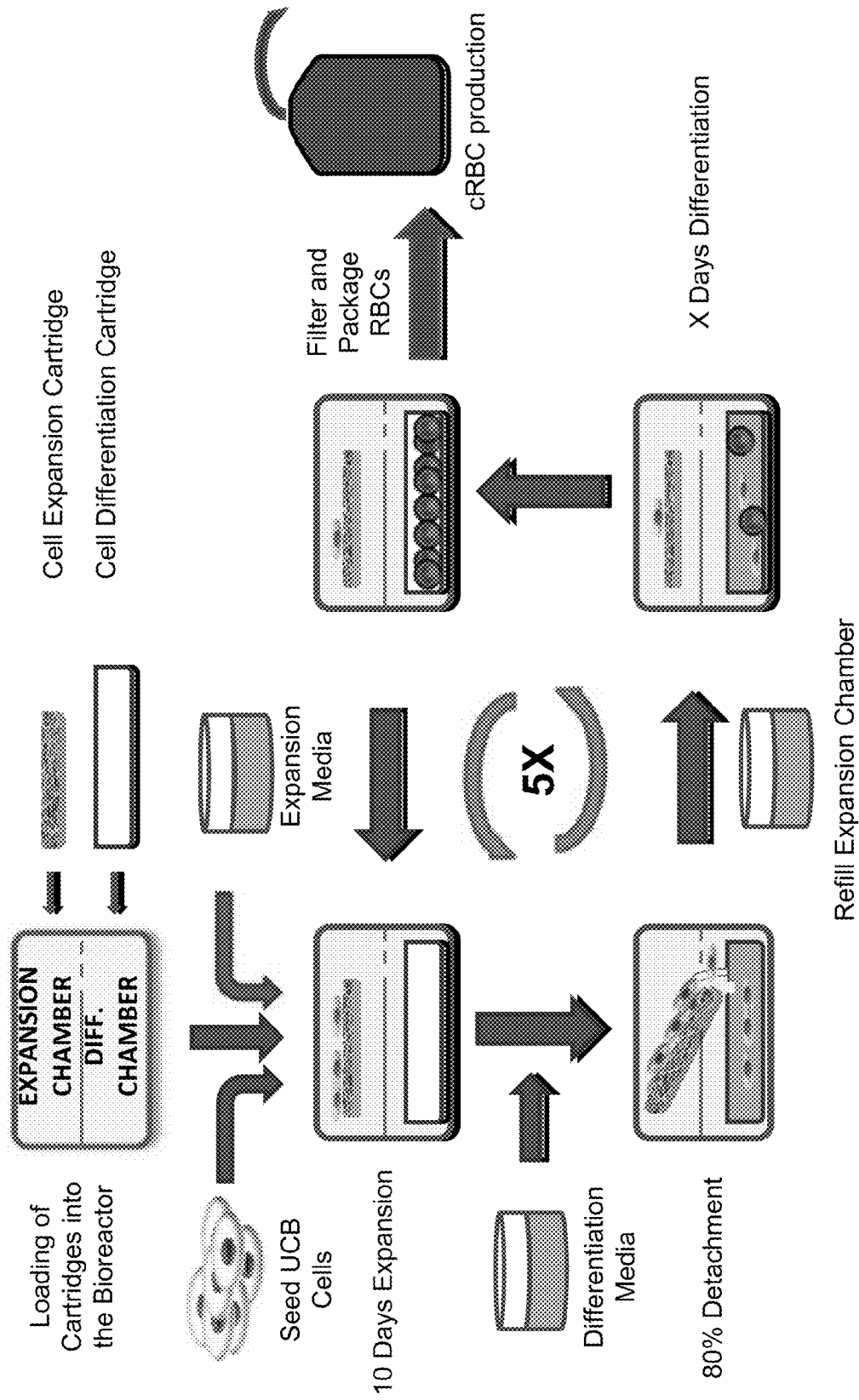
FIG. 45. A Hypothetical Bioreactor Device for NANEX RBC Production.

A hypothetical bioreactor process flow is shown below and in FIGS. 44 and 45. It is expected that a bioreactor would increase efficiency of expansion and differentiation.

Insert expansion and differentiation chamber containing nanofiber culture surface, Infuse with expansion medium, Stabilize temperature and with continuous, sterile gas exchange to the interior culture environment per optimized environmental values, Infuse with CD133+ UCB cells, Maintain environment, periodically flushing every days to collect differentiated cells, After sufficient expansion, flush expansion medium, Infuse cells with detachment treatment (enzyme solution, etc) to remove remaining cells, Flush 70-90% suspension volume into differentiation chamber, and re-suspend remaining 10% in expansion chamber with expansion medium, Suspend in differentiation medium, Maintain differentiation chamber until sufficient RBCs produced, Flush and collect media containing detached, differentiated RBCs, Repeat 5-12 indefinitely (At least 5×).

Figure 39:
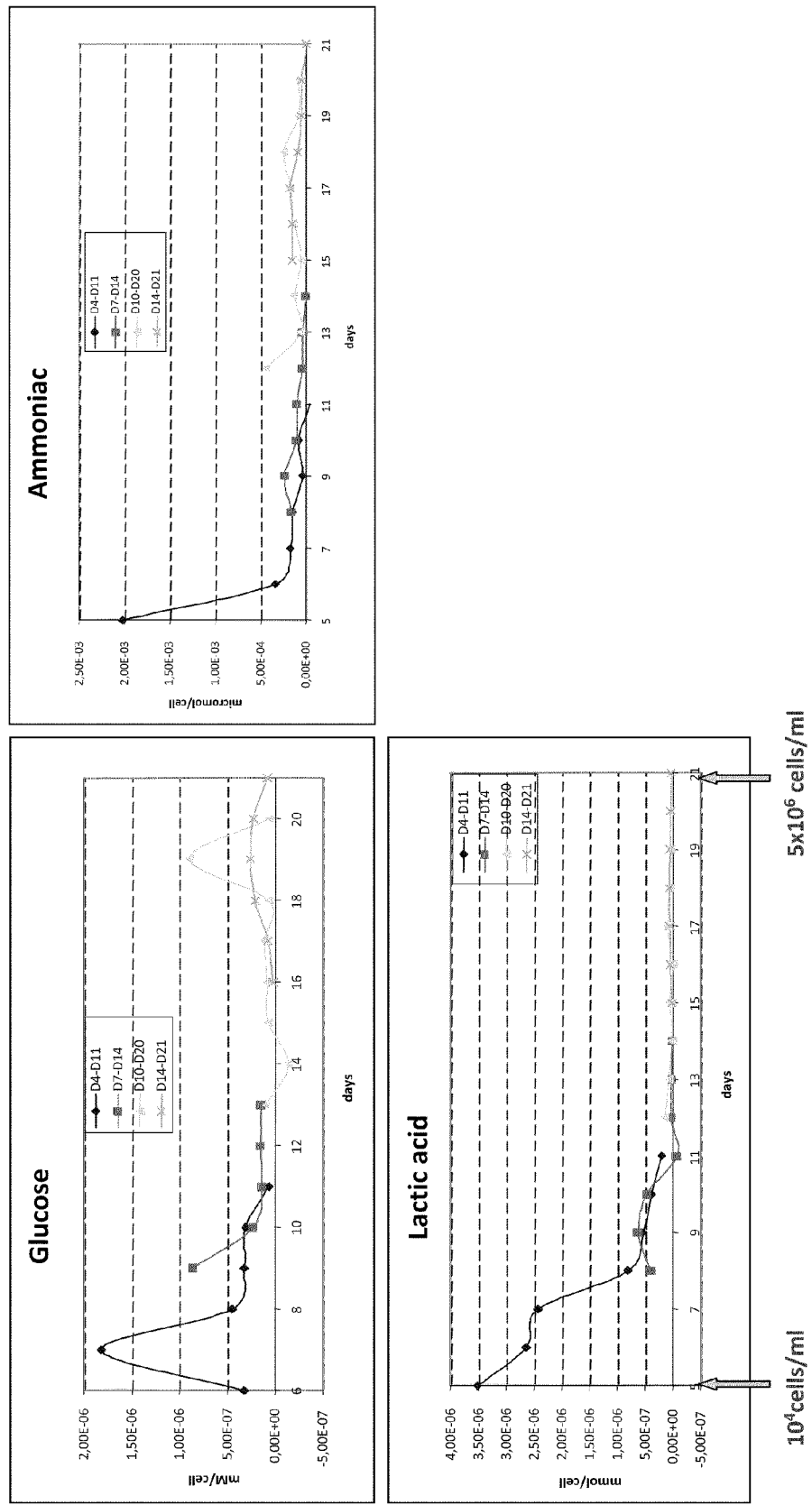
FIG. 39. Metabolites Concentration per Cell in Culture. Glucose, ammoniac and lactic acid levels were analyzed during proliferation.
Figure 41:
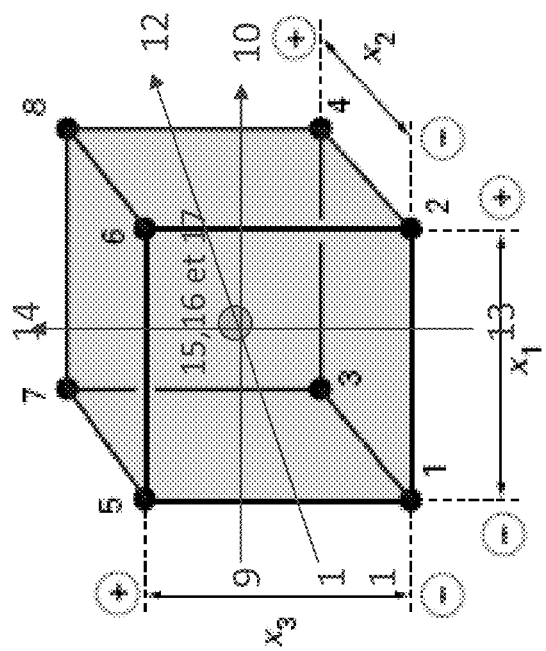
FIG. 41. Geometric Representation For Optimal Conditions Inside Bioreactor Device.
Figure 42:
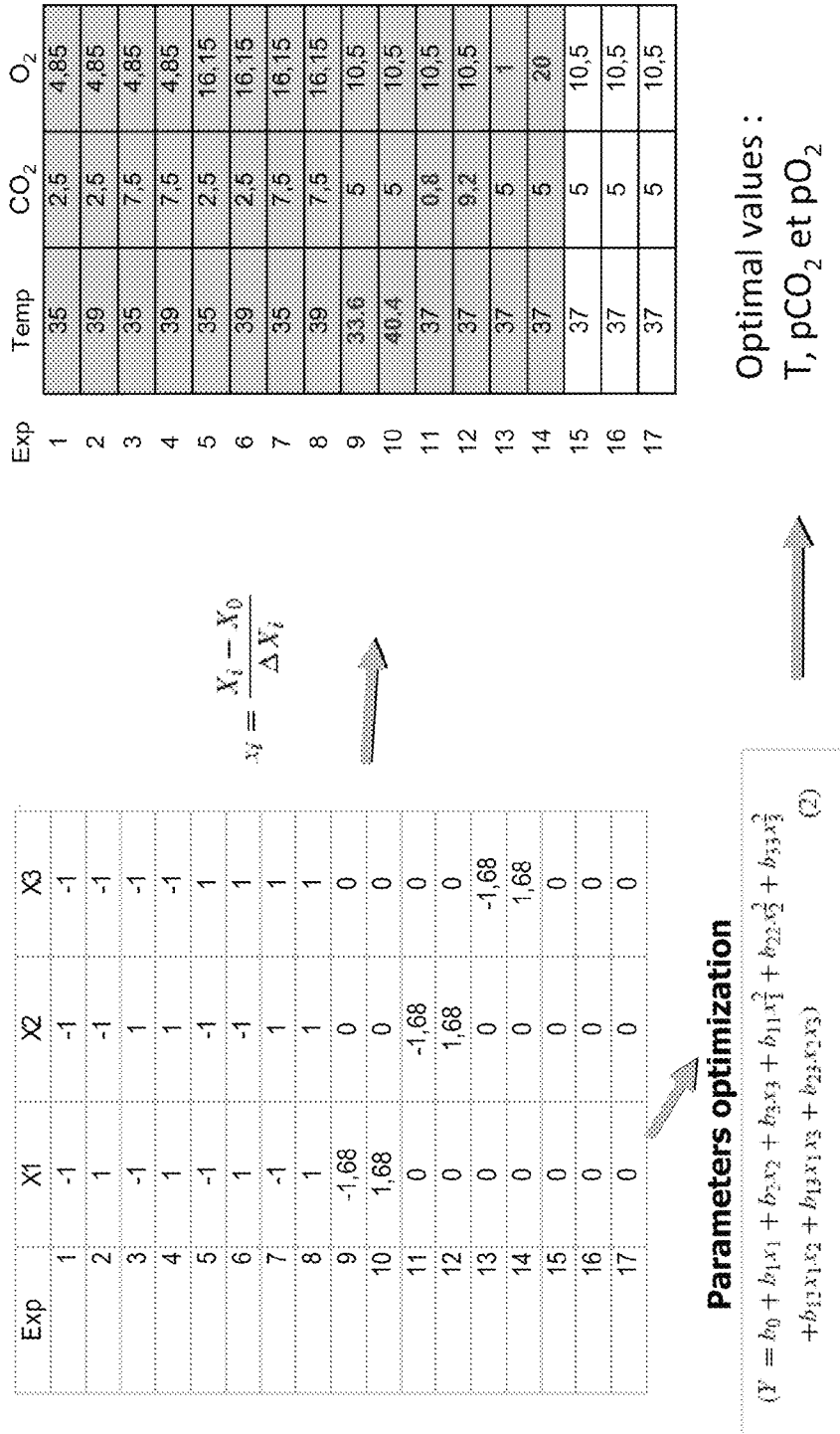
FIG. 42. 2$^3$ Factorial Central Composite Circumscribed (CCC) parameter optimization.

It is expected that optimization of such factors as glucose, ammonia, lactic acid, temperature, CO2 and O2 will result in higher efficiencies of expansion and differentiation. Some of these factors have been shown to enhance or inhibit growth (FIGS. 39-43). During proliferation phase there is a dramatic use of glucose and a dramatic production of ammonia and lactic acid. During maturation phase there is a weak use of glucose and a weak production of ammonia and lactic acid (FIG. 39).

All publications and patents mentioned herein, including those items listed below, are hereby incorporated by reference in their entirety as if each individual publication or patent was specifically and individually indicated to be incorporated by reference. In case of conflict, the present application, including any definitions herein, will control.

LITERATURE CITED

1. Chua, K. N. et al. Surface-aminated electrospun nanofibers enhance adhesion and expansion of human umbilical cord blood hematopoietic stem/progenitor cells. *Biomaterials.* 27, 6043-6051 (2006).
2. Hiranmoy Dasl, N. A., Mathew Josephl, Hai-Quan Mao2, Helen M. Blau3 and Vincent J. Pompili1*. Ex-vivo Expansion and Genetic Modification of Human Cord Blood-Derived CD133+ Stem Cells Potentiates In Vivo Functionality. *Manuscript* (2007).
3. Finney M R, G. N., Haynesworth S E, Martin J M, Hedrick D P, Swan J Z, Winter D G, Kadereit S, Joseph M E, Fu P, Pompili V J, Laughlin M J. Direct comparison of umbilical cord blood versus bone marrow derived endothelial precursor cells in mediating neovascularization in response to vascular ischemia. *Biology of Blood and Marrow Transplantation* 12, 12(5):585-93. (2006).
4. Atthoff B, H. J. Protein adsorption onto polyester surfaces: is there a need for surface activation? *J Biomed Mater Res B Appl Biomater.* 80, 121-30 (2007).
5. Miharada K, H. T., Sudo K, Nagasawa T, Nakamura Y. Efficient enucleation of erythroblasts differentiated in vitro from hematopoietic stem and progenitor cells. *Nat Biotechnol* 24, 1255-6 (2006).
6. Fibach E, M. D., Oppenheim A, Rachmilewitz E A. Proliferation and maturation of human erythroid progenitors in liquid culture. 73, 100-103 (1989).
7. Malik P, F. T., Barsky L L, Zeng L, Izadi P, Hiti A L, Weinberg K I, Coates T D, Meiselman H J, Kohn D B. An in vitro model of human red blood cell production from hematopoietic progenitor cells. *Blood* 91, 2664-71 (1998).
8. Mohandas N, P. M. Three-dimensional model of bone marrow. *Blood* 51, 633-43 (1978).
9. Hanspal M, H. J. The association of erythroblasts with macrophages promotes erythroid proliferation and maturation: a 30-kD heparin-binding protein is involved in this contact. *Blood* 84, 3494-504 (1994).
10. M A., L. The ultrastructure of the hemopoietic environment of the marrow: a review., *Exp Hematol.* 9, 391-410 (1981).
11. patients, I.v.m.p.o.h.e.c.f.t.b.o.n.d.a.o.t. In vitro mass production of human erythroid cells from the blood of normal donors and of thalassemic patients. *Blood Cells Mol. Dis.* 28, 169-180 (2002).
12. Giarratana, M. C. et al. Ex vivo generation of fully mature human red blood cells from hematopoietic stem cells. *Nat Biotechnol* 23, 69-74 (2005).
13. Giarratana, M. C. e. Cell culture bags allow a large extent of exvivoexpansion of LTC-IC and functional mature cells which can subsequently be frozen: interest for a large-scale clinical applications. *Bone Marrow Transplant.* 22, 707-715 (1998).
14. Verfaillie C, B. A., Iida J, McGlave P, McCarthy J. Adhesion of committed human hematopoietic progenitors to synthetic peptides from the C-terminal heparin-binding domain of fibronectin: cooperation between the integrin alpha 4 beta 1 and the CD44 adhesion receptor. *Blood* 84, 1802-1811 (1994).
15. Joneckis C C, A. R., Orringer E P, Wayner E A, Parise L V. Blood. 1993; 82:3548-3555. Integrin alpha 4 beta 1 and glycoprotein IV (CD36) are expressed on circulating reticulocytes in sickle cell anemia. *Blood* 82, 3548-3555 (1993).
16. Kie J H, J. Y., Woo S Y, Ryu K H, Park H Y, Chung W S, Seoh J Y Ultrastructural and phenotypic analysis of in vitro erythropoiesis from human cord blood CD34+ cells *Ann Hematol* 82, 278-83. (2003).
17. Quirici, N. et al. Differentiation and expansion of endothelial cells from human bone marrow CD133(+) cells. *Br J Haematol* 115, 186-94 (2001).
18. Ursula M. Gehling, S. E., Udo Schumacher, Christoph Wagener, Klaus Pantel, Marcus Otte, Gunter Schuch, Philippe Schafhausen, Thorsten Mende, Nerbil Kilic, Katrin Kluge, Birgit Schäfer, Dieter K. Hossfeld, and Walter Fiedler In vitro differentiation of endothelial cells from AC133-positive progenitor cells *Blood* 95, 3106-3112 (2000).
19. Miharada, K., Hiroyama, T., Sudo, K., Nagasawa, T. & Nakamura, Y. Refinement of cytokine use in the in vitro expansion of erythroid cells. *Hum Cell* 19, 30-7 (2006).
20. Miharada, K., Hiroyama, T., Sudo, K., Nagasawa, T. & Nakamura, Y. Lipocalin 2 functions as a negative regulator of red blood cell production in an autocrine fashion. *Faseb J* 19, 1881-3 (2005).
21. Winslow R M. "Current status of blood substitute research: towards a new paradigm". *J Intern Med* 253, 508-17 (2003).
22. Gregory C J, E. A. B., 1978 March; 51(3):527-37. Three stages of erythropoietic progenitor cell differentiation distinguished by a number of physical and biologic properties. *Blood* 51, 527-537 (1978).
23. Bagley, J., Rosenzweig, M., Marks, D. F. & Pykett, M. J. Extended culture of multipotent hematopoietic progenitors without cytokine augmentation in a novel three-dimensional device. *Exp. Hematol.* 27, 496-504 (1999).
24. Blair, A., Baker, C. L., Pamphilon, D. H. & Judson, P. A. Ex vivo expansion of megakaryocyte progenitor cells from normal bone marrow and peripheral blood and from patients with haematological malignancies. *Br J Haematol* 116, 912-9 (2002).
25. Brugger, W. et al. Ex vivo expansion of enriched peripheral blood CD34+ progenitor cells by stem cell factor, interleukin-1 beta (IL-1 beta), IL-6, IL-3, interferon-gamma, and erythropoietin. *Blood* 81, 2579-84 (1993).
26. Chivu, M. et al. Ex vivo differentiation of umbilical cord blood progenitor cells in the presence of placental conditioned medium. *J Cell Mol Med* 6, 609-20 (2002).
27. De Bruyn, C., Delforge, A., Martiat, P. & Bron, D. Ex vivo expansion of megakaryocyte progenitor cells: cord blood versus mobilized peripheral blood. *Stem Cells Dev* 14, 415-24 (2005).
28. Chua, K. N. et al. Functional nanofiber scaffolds with different spacers modulate adhesion and expansion of cryopreserved umbilical cord blood hematopoietic stem/progenitor cells. *Experimental Hematology* In press (2007).
29. Nelson, T.e.a. journal of American college of surgeons 202, 418-422 (2006).
30. Kelly, P., Kurtzberg, J., Vichinsky, E. & Lubin, B. Umbilical cord blood stem cells: application for the treatment of patients with hemoglobinopathies [see comments]. *J Pediatr* 130, 695-703 (1997).
31. Akiyama, M. et al. Changes of telomere length in children after hematopoietic stem cell transplantation. *Bone Marrow Transplant* 21, 167-71 (1998).
32. M Akiyama, e.a. Shortening of telomeres in recipients of both autologous and allogeneic hematopoietic stem cell transplantation. *Bone Marrow Transplantation* 25, 441-447 (2000).
33. Stacey, G. N. et al. The development of 'feeder' cells for the preparation of clinical grade hES cell lines: challenges and solutions. *J Biotechnol* 125, 583-8 (2006).
34. Douay, L. & Andreu, G. Ex vivo production of human red blood cells from hematopoietic stem cells: what is the future in transfusion? *Transfus Med Rev* 21, 91-100 (2007).
35. Douay, L. & Giarratana, M. C. [In vitro generation of mature and functional human red blood cells: a model with multidisciplinary perspectives]. *Bull Acad Natl Med* 189, 903-13; discussion 914-5 (2005).

36. Douay, L. & Giarratana, M. C. The cultured red blood cell: a study tool with therapeutic perspectives. *Cell Cycle* 4, 999-1000 (2005).
37. Giarratana, M. C. & Douay, L. [Cultured red blood cells: a new step in cell engineering]. *Med Sci (Paris)* 21, 231-2 (2005).
38. Douay, L. [Transfusional perspectives for ex vivo control of hematopoiesis]. *Transfus Clin Biol* 10, 151-5 (2003).
39. Douay, L. [From control of hematopoiesis to cellular therapy: the perspectives for transfusion]. *Ann Biol Clin (Paris)* 61, 259-67 (2003).
40. Chua, K. N. et al. Stable immobilization of rat hepatocyte spheroids on galactosylated nanofiber scaffold. *Biomaterials.* 26, 2537-2547 (2005).
41. Finney, M. R. et al. Direct comparison of umbilical cord blood versus bone marrow-derived endothelial precursor cells in mediating neovascularization in response to vascular ischemia. *Biol Blood Marrow Transplant* 12, 585-93 (2006).
42. Hartley, P. G. & Scales, P. J. Electrostatic Properties of Polyelectrolyte Modified Surfaces Studied by Direct Force Measurement. *Langmuir* 14, 6948-6955 (1998).
43. Scicchitano M S, M. D., Tierney L A, Narayanan P K, Schwartz L W. In vitro expansion of human cord blood CD36+ erythroid progenitors: temporal changes in gene and protein expression. *Exp Hematol* 31, 760-9 (2003).
44. Daniels, G. Expression of red cell surface antigens during erythropoiesis. *Vox Sang.* 78 Suppl 2, 149-53 (2000).
45. Sawada K, K. S., Dai C H, Koury S T, Horn S T, Glick A D, Civin C I. Purification of human blood burst-forming units-erythroid and demonstration of the evolution of erythropoietin receptors. *J Cell Physiol* 142, 219-30 (1990).
46. Long, M. W., Briddell, R., Walter, A. W., Bruno, E. & Hoffman, R. Human hematopoietic stem cell adherence to cytokines and matrix molecules. *J. Clin. Invest.* 90, 251-255 (1992).
47. Molla, A., Mossuz, P. & Berthier, R. Extracellular matrix receptors and the differentiation of human megakaryocytes in vitro. *Leuk Lymphoma* 33, 15-23 (1999).
48. Vuillet-Gaugler, M. H. et al. Loss of attachment to fibronectin with terminal human erythroid differentiation. *Blood* 75, 865-73 (1990).
49. Gandhi, M. J., Drachman, J. G., Reems, J. A., Thorning, D. & Lannutti, B. J. A novel strategy for generating platelet-like fragments from megakaryocytic cell lines and human progenitor cells. *Blood Cells Mol. Dis.* 35, 70-73 (2005).
50. Cabrita, G. J. M. et al. Hematopoietic stem cells: from the bone to the bioreactor. *Trends Biotechnol.* 21 233-240 (2003).
51. Mantalaris, A., Keng, P., Bourne, P., Chang, A. Y. & Wu, J. H. Engineering a human bone marrow model: a case study on ex vivo erythropoiesis. *Biotechnol Prog* 14, 126-133 (1998).
52. Meissner, P., Schröder, B., Herfurth, C. & Biselli, M. Development of a fixed bed bioreactor for the expansion of human hematopoietic progenitor cells. *Cytotechnology* 30, 227-234 (1999).
53. Plett, P. A., Abonour, R., Frankovitz, S. M. & Orschell, C. M. Impact of modeled microgravity on migration, differentiation, and cell cycle control of primitive human hematopoietic progenitor cells. *Exp Hematol* 32, 773-81 (2004).
54. Plett, P. A., Frankovitz, S. M., Abonour, R. & Orschell-Traycoff, C. M. Proliferation of human hematopoietic bone marrow cells in simulated microgravity. *In Vitro Cell Dev Biol Anim* 37, 73-8 (2001).
55. Chiu, B., Wan, J. Z., Abley, D. & Akabutu, J. Induction of vascular endothelial phenotype and cellular proliferation from human cord blood stem cells cultured in simulated microgravity. *Acta Astronaut* 56, 918-22 (2005).
56. Ehring, B. et al. Expansion of HPCs from cord blood in a novel 3D matrix. *Cytotherapy* 5, 490-9 (2003).
57. Banu, N., Rosenzweig, M., Kim, H., Bagley, J. & Pykett, M. Cytokine-augmented culture of haematopoietic progenitor cells in a novel three-dimensional cell growth matrix. *Cytokine* 13, 349-358 (2001).
58. Zhao, F. & Ma, T. Perfusion bioreactor system for human mesenchymal stem cell tissue engineering: dynamic cell seeding and construct development. *Biotechnol Bioeng* 91, 482-93 (2005).
59. Braccini, A. et al. Three-dimensional perfusion culture of human bone marrow cells and generation of osteoinductive grafts. *Stem Cells* 23, 1066-72 (2005).
60. Boiron J M, D. B., Cailliot C, Launay B, Attal M, Mazurier F, McNiece I K, Ivanovic Z, Caraux J, Marit G, Reiffers J. Large-scale expansion and transplantation of CD34(+) hematopoietic cells: in vitro and in vivo confirmation of neutropenia abrogation related to the expansion process without impairment of the long-term engraftment capacity. *Transfusion* 46, 1934-42 (2006).

This application herein incorporates by reference the entire teachings of U.S. Patent Publication Nos. 2004/0258670 and 2005/0069527

The practice of the present invention will employ, where appropriate and unless otherwise indicated, conventional techniques of cell biology, cell culture, molecular biology, transgenic biology, microbiology, virology, recombinant DNA, and immunology, which are within the skill of the art. Such techniques are described in the literature. See, for example, Molecular Cloning: A Laboratory Manual, 3rd Ed., ed. by Sambrook and Russell (Cold Spring Harbor Laboratory Press: 2001); the treatise, Methods In Enzymology (Academic Press, Inc., N.Y.); Using Antibodies, Second Edition by Harlow and Lane, Cold Spring Harbor Press, New York, 1999; Current Protocols in Cell Biology, ed. by Bonifacino, Dasso, Lippincott-Schwartz, Harford, and Yamada, John Wiley and Sons, Inc., New York, 1999.

The invention claimed is:

1. A method for producing erythrocytes comprising:
 (a) providing a purified or selected population of CD133+ cells,
 (b) culturing said CD133+ cells on polymeric nanofibers to expand the number of CD133+ cells, and
 (c) directing differentiation of the expanded CD133+ cells into erythrocytes, wherein said CD133+ cells are cultured without stromal cells, and wherein directing differentiation comprises sequentially exposing cells to media comprising:
  a) Stem Cell Growth Factor 1 (SCF), Erythropoietin (EPO) and Interleukin 3,
  b) SCF and EPO, and
  c) EPO.

2. The method of claim 1, wherein said expansion comprises increasing the number of CD133+ cells by at least 300-fold.

3. The method of claim 1, wherein the CD133+ cells are CD133+CD34− cells, CD133+CD34+ cells, or combinations thereof.

4. The method of claim 1, wherein the CD133+ cells are CD133+CD34+KDR-CXCR4-cells.

5. The method of claim 1, wherein at least 10% of the total cells are CD133+.

6. The method of claim 1, wherein said expansion occurs in about 10 days.

7. The method of claim 1, wherein said polymeric nanofibers are random nanofiber meshes or films.

8. The method of claim 1, wherein said polymeric nanofibers are aligned nanofiber meshes or films.

9. The method of claim 1, wherein said polymeric nanofibers are polyethersulfone (PES) meshes or films.

10. The method of claim 1, wherein said polymeric nanofibers are surface-conjugated with functional groups.

11. The method of claim 10, wherein said functional groups are selected from the group consisting of: hydroxyl, carboxyl, and amino groups.

12. The method of claim 1, wherein said polymeric nanofibers are surface-conjugated with fibronectin.

13. The method of claim 1, wherein said CD133+ cells are mammalian cells.

14. The method of claim 1, wherein said CD133+ cells are human cells.

15. The method of claim 1, wherein the CD133+ cells are isolated from umbilical cord blood, bone marrow or peripheral blood or combinations thereof.

16. The method of claim 1, wherein the CD133+ cells are enriched from umbilical cord blood, bone marrow or peripheral blood or combinations thereof.

17. The method of claim 16, wherein the composition comprises CD133+ enriched at least 2-fold over bone marrow mononuclear cells.

18. The method of claim 1, wherein the expanded CD133+ cells are recultured for further expansion.

19. The method of claim 1, wherein the erythrocytes are O Rh negative cells.

20. The method of claim 1, wherein the total number of differentiated cells is increased by at least 4500-fold over the starting number of CD133+ cells.

21. The method of claim 1, wherein said differentiation occurs in about 6-28 days.

22. The method of claim 1, wherein the CD133+ cells express a recombinant transgene.

23. The method of claim 22, wherein the CD133+ cells express a recombinant proangiogenic growth factor.

24. The method of claim 23, wherein the proangiogenic growth factor is VEGF164, PDGF-BB, or both.

25. The method of claim 24, wherein VEGF164 and PDGF-BB are expressed in a bicistronic co-delivery vector.

26. A method for producing erythrocytes comprising:
(a) providing a purified or selected population of CD133+ cells,
(b) culturing said CD133+ cells in a bioreactor containing polymeric nanofibers to expand the number of CD133+ cells, and
(c) directing differentiation of the expanded CD133+ cells into erythrocytes, wherein directing differentiation comprises sequentially exposing cells to media comprising:
a) Stem Cell Growth Factor 1 (SCF), Erythropoietin (EPO) and Interleukin 3,
b) SCF and EPO, and
c) EPO.

27. The method of claim 26, wherein said CD133+ cells are expanded about 300-fold.

28. The method of claim 26, wherein the total number of differentiated cells is increased by at least 4500-fold over the starting number of CD133+ cells.

29. The method of claim 26, wherein said differentiation occurs in about 6-28 days.

30. The method of claim 26, wherein said expansion and differentiation occur in about 28 days.

31. The method of claim 26, wherein cellular waste production is optimized during culturing.

32. The method of claim 31, wherein cellular waste is selected from the group consisting of ammonia and lactic acid.

33. The method of claim 26, wherein $CO_2$ levels, $O_2$ levels and temperature are optimized during culturing.

34. The method of claim 33, wherein $CO_2$ levels, $O_2$ levels and temperature are re-optimized during different phases of culturing.

* * * * *